(12) United States Patent
Tikoo et al.

(10) Patent No.: US 7,264,818 B2
(45) Date of Patent: Sep. 4, 2007

(54) BAV PACKAGING REGIONS AND E1 TRANSCRIPTIONAL CONTROL REGIONS

(75) Inventors: Suresh K. Tikoo, Saskatoon (CA); Li Xing, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 10/866,505

(22) Filed: Jun. 10, 2004

(65) Prior Publication Data

US 2005/0129713 A1 Jun. 16, 2005

Related U.S. Application Data

(60) Provisional application No. 60/477,540, filed on Jun. 10, 2003.

(51) Int. Cl.
*A61K 39/23* (2006.01)
*C12N 5/10* (2006.01)
*C12N 7/00* (2006.01)

(52) U.S. Cl. ................ 424/233.1; 435/456; 435/235.1

(58) Field of Classification Search ................ 435/471, 435/547, 235.1, 320.1; 424/199.1, 93.2, 424/233.1
See application file for complete search history.

(56) References Cited

U.S. PATENT DOCUMENTS

| | | |
|---|---|---|
| 5,820,868 A | 10/1998 | Mittal et al. |
| 6,001,591 A | 12/1999 | Mittal et al. |
| 6,086,890 A | 7/2000 | Mittal et al. |
| 6,319,716 B1 * | 11/2001 | Tikoo et al. ................ 435/471 |
| 6,458,586 B1 | 10/2002 | Tikoo et al. |
| 6,479,290 B1 * | 11/2002 | Mehtali et al. ............. 435/457 |

FOREIGN PATENT DOCUMENTS

EP 0 259 149 3/1988
WO WO-2004/108939 A2 12/2004

OTHER PUBLICATIONS

Bowie et al., "Deciphering the message in protein sequences: tolerance to amino acid substitutions," Science vol. 247:1306-1310 (1990).□□.*
Reddy et al., "Replication-Defective Bovine Adenovirus type 3 as an Expression Vector," Journal of Virology, Nov. 1999, pp. 9137-9144.*

(Continued)

*Primary Examiner*—Bruce R. Campbell
*Assistant Examiner*—M. Franco Salvoza
(74) *Attorney, Agent, or Firm*—Morrison & Foerster LLP

(57) ABSTRACT

The present invention relates to the identification of bovine adenovirus sequence(s) essential for encapsidation and E1 transcriptional control regions. The present invention provides adenovirus expression systems, host cells and compositions comprising adenovirus vectors which comprise one or more BAV sequence(s) essential for encapsidation, as well as helper virus which express BAV sequences essential for encapsidation. The present invention also provides helper vectors comprising a BAV sequence essential for encapsidation which is used in a helper virus for propagating recombinant adenovirus. The present invention also provides adenovirus expression systems, host cells and compositions comprising adenovirus vectors which comprise modifications in BAV E1 transcriptional control regions. The present invention also provides methods for making adenovirus vectors comprising BAV sequence(s) essential for encapsidation as well as modifications in BAV E1 transcriptional control regions.

42 Claims, 16 Drawing Sheets

Figure 2A:
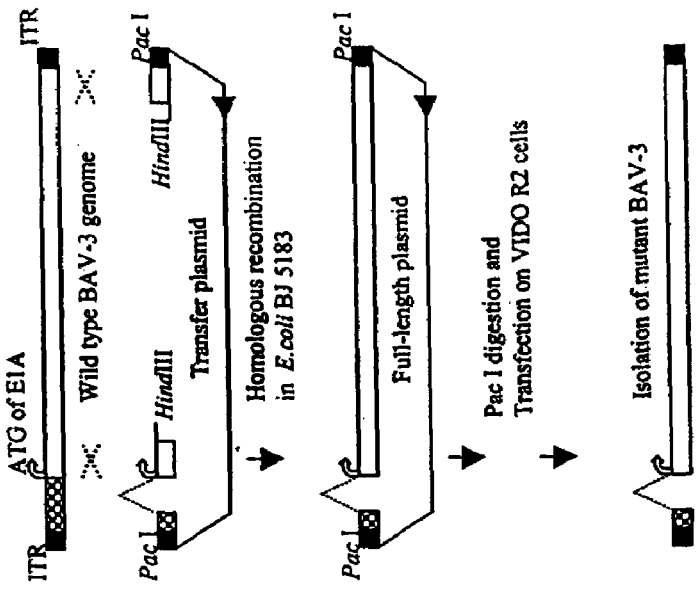

```
  1 CATCATCAAT AATCTACAGT ACACTGATGG CAGCGGTCCA ACTGCCAATC ATTTTTGCCA
 61 CGTCATTTAT GACGCAACGA CGGCGAGCGT GGCGTGCTGA CGTAACTGTG GGGCGGAGCG
121 CGTCGCGGAG GCGGCGGCGC TGGGCGGGGC TGAGGGCGGC GGGGGCGGCG CGCGGGGCGG
181 CGCGCGGGGC GGGGCGAGGG GCGGAGTTCC GCACCCGCTA CGTCATTTTC AGACATTTTT
241 TAGCAAATTT GCGCCTTTTG CAAGCATTTT TCTCACATTT CAGGTATTTA GAGGGCGGAT
301 TTTTGGTGTT CGTACTTCCG TGTCACATAG TTCACTGTCA ATCTTCATTA CGGCTTAGAC
361 AAATTTTCGG CGTCTTTTCC GGGTTTATGT CCCCGGTCAC CTTTATGACT GTGTGAAACA
421 CACCTGCCCA TTGTTTACCC TTGGTCAGTT TTTTCGTCTC CTAGGGTGGG AACATCAAGA
481 ACAAATTTGC CGAGTAATTG TGCACCTTTT TCCGCGTTAG GACTGCGTTT CACACGTAGA
541 CAGACTTTTT CTCATTTTCT CACACTCCGT CGTCCGCTTC AGAGCTCTGC GTCTTCGCTG
601 CCACCATGAA GTACCTGGTC CTCGTTCTCA ACGACGGCAT GAGTCGAATT GAAAAAGCTC
```

OTHER PUBLICATIONS

Reddy et al., "Nucleotide Sequence Genome Organization, and Transcription Map of Bovine Adenovirus Type 3," *Journal of Virology*, Feb. 1998, pp. 1394-1402.*

Russell, W.C. "Update on Adenovirus and its Vectors," *J. Gen. Virol.* 81(11):2573-2604 (2000).*

Ausubel, F.M. et al. eds. (1987). *Current Protocols in Molecular Biology*, Supp. 30, Section 7.7.18, Table 7.7.1, two pages.

Babiss, L.E. et al. (Feb. 1991). "Promoter of the Adenovirus Polypeptide IX Gene: Similarity to E1B and Inactivation by Substitution of the Simian Virus 40 TATA Element," *J. Virol.* 65(2):598-605.

Bartha, A. (1969). "Proposal For Subgrouping of Bovine Adenoviruses," *Acta. Vet. Acad. Sci. Hung* 19(3):319-321.

Baxi, M.K. et al. (1998). "Characterization of Bovine Adenovirus Type 3 Early Region 2B," *Virus Genes* 16(3):313-316.

Baxi, M.K. et al. (1999). "Transcription Map and Expression of Bovine Herpesvirus-1 Glycoprotein D in Early Region 4 of Bovine Adenovirus-3," *Virology* 261:143-152.

Berk, A.J. et al. (Aug. 1979). "Pre-Early Adenovirus 5 Gene Product Regulates Synthesis of Early Viral Messenger RNAs," *Cell* 17:935-944.

Bos, J.L. et al. (1983). "The E1b Promoter of Ad12 in Mouse L tk- Cells Is Activated by Adenovirus Region E1a," *EMBO J.* 2(1):73-76.

Braun, R.P. et al. (Sep. 15, 1988). "Immunogenic Duplex Nucleic Acids are Nuclease Resistant," *The Journal of Immunology* 141(6):2084-2089.

Brennan, S. et al. (1990). "Embryonic Transcriptional Activation of a *Xenopus* Cytoskeletal Actin Gene Does Not Require a Serum Response Element," *Roux's Arch. Dev. Biol.* 199:89-96.

Chartier, C. et al. (Jul. 1996). "Efficient Generation of Recombinant Adenovirus Vectors by Homologous Recombination in *Escherichia coli*," *J. Virol.* 70(7):4805-4810.

Chaturvedi, S. et al. (1996). "Stabilization of Triple-Stranded Oligonucleotide Complexes: Use of Probes Containing Alternating Phosphodiester and Stereo-Uniform Cationic Phosphoramidate Linkages," *Nucleic Acid Res.* 24(12):2318-2323.

Daniell, E. (Aug. 1976). "Genome Structure of Incomplete Particles of Adenovirus," *J. Virol.* 19(2):685-708.

Darbyshire, J.H. et al. (1965). "A New Adenovirus Serotype of Bovine Origin," *J. Comp. Pathol.* 75:327-330.

D'Halluin, J.C. (1995). "Virus Assembly" In *Curr. Top. Microbiol. Immunol* Springer-Verlag. 199:47-66.

D'Halluin, J-C. et al. (May 1978). "Adenovirus Type 2 Assembly Analyzed by Reversible Cross-Linking of Labile Intermediates," *J. Virol.* 26(2):357-363.

D'Halluin, J-C. et al. (May 1978). "Temperature-Sensitive Mutant of Adenovirus Type 2 Blocked in Virion Assemby: Accumulation of Light Intermediate Particles," *J. Virol.* 26(2):344-356.

D'Halluin, J-C. et al. (Jan. 1980). "Morphogenesis of Human Adenovirus Type 2 Studied with Fiber- and Fiber and Penton Base-Defective Temperature-Sensitive Mutants," *J. Virol.* 33(1):88-99.

Edvardsson, B. et al. (Aug. 1976). "Intermediates in Adenovirus Assembly," *J. Virol.* 19(2):533-547.

Edvardsson, B. et al. (Feb. 1978). "Assembly Intermediates Among Adenovirus Type 5 Temperature-Sensitive Mutants," *J. Virol.* 25(2):641-651.

Fallaux, F.J. et al. (Sep. 1, 1998). "New Helper Cells and Matched Early Region 1-Deleted Adenovirus Vectors Prevent Generation of Replication-Competent Adenoviruses," *Human Gene Therapy* 9:1909-1917.

GenBank Accession No. AF030154, created Oct. 20, 2000, located at <http://www.ncbi.nlm.nih.gov/entrez.viewer.fcgi?db=nucleotide&val=2935210> last visited on Nov. 5, 2004, 16 pages.

GenBank Accession No. AF036092, created on Feb. 17, 2004, located at <http://www.ncbi.nlm.nih.gov/entrez.viewer.fcgi?db=nucleotide&val=34223996> last visited on Nov. 5, 2004, 17 pages.

GenBank Accession No. AF252854, created on Aug. 15, 2000, located at <http://www.ncbi.nlm.nih.gov/entrez.viewer.fcgi?db=nucleotide&val=9802268> last visited on Nov. 5, 2004, 12 pages.

GenBank Accession No. J01917, created on Mar. 14, 1996, located at <http://www.ncbi.nlm.nih.gov/entrez.viewer.fcgi?db=nucleotide&val=209811> last visited on Nov. 5, 2004, 34 pages.

GenBank Accession No. M73260, created Apr. 8, 1996, located at <http://www . . . /query.fcgi?cmd=Retrieve&db=Nucleotide&list_uids=209842&dopt=GenBank . . . > last visited on Oct. 26, 2000, 12 pages.

GenBank Accession No. U77082, created Dec. 14, 1996, located at <http://www.ncbi.nlm.nih.gov/entrez.viewer.fcgi?db=nucleotide&val=1732265> last visited on Nov. 5, 2004, 16 pages.

Gräble, M. et al. (May 1990). "Adenovirus Type 5 Packaging Domain Is Composed of a Repeated Element That Is Functionally Redundant," *Journal of Virology* 64(5):2047-2056.

Gräble, M. et al. (Feb. 1992). "*cis* and *trans* Requirements for the Selective Packaging of Adenovirus Type 5 DNA," *J. Virol.* 66(2):723-731.

Graham, F.L. et al. (1977). "Characteristics of a Human Cell Line Transformed by DNA from Human Adenovirus Type 5," *J. Gen. Virol.* 36:59-74.

Grand, R.J.A. et al. (1987). "The Structure and Functions of the Adenovirus Early Region 1 Proteins," *Biochem. J.* 241:25-38.

Gustin, K.E. et al. (Oct. 1998). "Encapsidation of Viral DNA Requires the Adenovirus L1 52/55-Kilodalton Protein," *J. Virol.* 72(10):7860-7870.

Hammarskjöld, M-L. et al. (Jul. 1980). "Encapsidation of Adenovirus 16 DNA Is Directed by a Small DNA Sequence at the Left End of the Genome," *Cell* 20:787-795.

Hampsey, M. et al. (Jun. 1998). "Molecular Genetics of the RNA Polymerase II General Transcriptional Machinery," *Microbiol. Mol. Biol. Rev.* 62(2):465-503.

Hatfield, L. et al. (1991). "Redundant Elements in the Adenovirus Type 5 Inverted Terminal Repeat Promote Bidirectional Transcription in Vitro and Are Important for Virus Growth in Vivo," *Virology* 184:265-276.

Hatfield, L. et al. (Jul. 1993). "The NFIII/OCT-1 Binding Site Stimulates Adenovirus DNA Repliction In Vivo and Is Functionally Redundant with Adjacent Sequences," *J. Virol.* 67(7):3931-3939.

Hearing, P. et al. (Jul. 1983). "The Adenovirus Type 5 E1A Transcriptional Control Region Contains a Duplicated Enhancer Element," *Cell* 33:695-703.

Hearing, P. et al. (Apr. 25, 1986). "The Adenovirus Type 5 E1A Enhancer Contains Two Functionally Distinct Domains: One is Specific for E1A and the Other Modulates All Early Units in *Cis*," *Cell* 45:229-236.

Hearing, P. et al. (Aug. 1987). "Identification of a Repeated Sequence Element Required for Efficient Encapsidation of the Adenovirus Type 5 Chromosome," *J. Virol.* 61(8):2555-2558.

Hehir, K.M. et al. (Dec. 1996). "Molecular Characterization of Replication-Competent Variants of Adenovirus Vectors and Genome Modifications To Prevent Their Occurrence," *J. Virol.* 70(12):8459-8467.

Idamakanti, N. et al. (1999). "Transcription Mapping and Characterization of 284R and 121R Proteins Produced from Early Region 3 of Bovine Adenovirus Type 3," *Virology* 256:351-359.

Jones, N. et al. (Aug. 1979). "An Adenovirus Type 5 Early Gene Function Regulates Expression of Other Early Viral Genes," *Proc. Natl. Acad. Sci. USA* 76(8):3665-3669.

Kadonaga, J.T. et al. (Dec. 24, 1987). "Isolation of cDNA Encoding Transcription Factor Sp1 and Functional Analysis of the DNA Binding Domain," *Cell* 51:1079-1090.

Kunkel, T.A. et al. (1987). "Rapid and Efficient Site Mutagenesis Without Phenotypic Selection," Chapter 19 In *Methods in Enzymology* 154:367-382.

Latimer, L.J.P. et al. (1995). "Specificity of Monoclonal Antibodies Produced Against Phosphorothioate and Ribo Modified DNAs," *Molecular Immunology* 32(14/15):1057-1064.

Lee, J.B. et al. (1998). "Genetic Organization and DNA Sequence of Early Region 4 of Bovine Adenovirus Type 3," *Virus Genes* 17(1):99-100.

Maat, J. et al. (Jun. 1980). "The Nucleotide Sequence of Adenovirus Type 5 Early Region E1: The Region Between Map Positions 8.0 (*Hin*dIII site) and 11.8 (*Sma*I site)," *Gene* 10(1):27-38.

Milanesi, L. et al. (1995). "Recognition of Poly-A Signals with Hamming Clustering," *Proceedings of the Third International Symposium on Bioinformatics, Supercomputing and Complex Genome Analysis*, Lim, H.A. et al. eds. World Scientific Publishing, Singapore, pp. 461-466.

Milanesi, L. et al. (Oct. 1996). "Hamming-Clustering Method for Signals Prediction in 5' and 3' Regions of Eukaryotic Genes," *Comput. Applic. Biosci.* 12(5):399-404.

Milanesi, L. et al. (1998). "Prediction of Human Gene Structure" Chapter 10 In *Guide to Human Genome Computing* Second Edition, Bishop, M.J. ed. Academic Press, Inc.: Cambridge pp. 215-256.

Milanesi, L. et al. (1999). "GeneBuilder: Interactive *in silico* Prediction of Gene Structure," *Bioformatics* 15(7/8):612-621.

Mittereder, N. et al. (Nov. 1996). "Evaluation of the Concentration and Bioactivity of Adenovirus Vectors for Gene Therapy," *J. Virol.* 70(11):7498-7509.

Mohanty, S.B. et al. (Dec. 1971). "Comparative Study of Bovine Adenoviruses," *Am. J. Vet. Res.* 32(12):1899-1905.

Parks, R.J. et al. (Nov. 1996). "A Helper-Dependent Adenovirus Vector System: Removal of Helper Virus by Cre-Mediated Excision of the Viral Packaging Signal," 93:13565-13570.

Peyrottes, S. et al. (1996). "Oligodeoxynucleoside Phosphoramidates (P-NH$_2$): Synthesis and Thermal Stability of Duplexes with DNA and RNA Targets," *Nucleic Acids Res.* 24(10):1841-1848.

Reddy, P.S. et al. (1995). "Comparison of the Inverted Terminal Repetition Sequences From Five Porcine Adenovirus Serotypes," *Virology* 212:237-239.

Reddy, P.S. et al. (Feb. 1998). "Nucleotide Sequence, Genome Organization, and Transcription Map of Bovine Adenovirus Type 3," *Journal of Virology* 72(2):1394-1402.

Reddy, P.S. et al. (Nov. 1999). "Replication-Defective Bovine Adenovirus Type 3 as an Expression Vector," *Journal of Virology* 73(11):9137-9144.

Reddy, P.S. et al. (1999). "Characterization of Early Region 1 and pIX of Bovine Adenovirus-3," *Virology* 253:299-308.

Reese, M.G. et al. (Jan. 2-7, 1996). "Large Scale Sequencing Specific Neural Networks for Promoter and Splice Site Recognition," *Biocomputing: Proceedings of the Jan. 2-7, 1996 Pacific Symposium*, Hunter, L. et al. eds. World Scientific Publishing Co., Singapore, pp. 737-738.

Reese, M.G. et al. (Sep. 16-20, 1995). "New Neural Network Algorithms for Improved Eukaryotic Promoter Site Recognition," *The Seventh International Genome Squencing and Analysis Conference*, Hilton Head Island, SC P-45, Abstract A-26.

Robinson, C.C. et al. (Sep. 1984). "Polar Encapsidation of Adenovirus DNA: Evolutionary Variants Reveal Dispensable Sequences Near the Left Ends of Ad3 Genomes," *Virology* 137(2):276-286.

Russell, W.C. (Nov. 2000). "Update on Adenovirus and its Vectors," *J. Gen. Virol.* 81(11):2573-2604.

Schmid, S.I. et al. (May 1997). "Bipartite Structure and Functional Independence of Adenovirus Type 5 Packaging Elements," *J. Virol.* 71(5):3375-3384.

Schmid, S.I. et al. (Aug. 1998). "Cellular Components Interact with Adenovirus Type 5 Minimal DNA Packaging Domains," *J. Virol.* 72(8):6339-6347.

Schultz, R.G. et al. (1996). "Oligo-2'-fluoro-2'-deoxynucleotide N3'→ P5' Phosphoramidates: Synthesis and Properties," *Nucleic Acids Res.* 24(15):2966-2973.

Shenk, T. et al. (1991). "Transcriptional and Transforming Activities of the Adenovirus E1A Proteins," In *Advances in Cancer Research* Vande Woude, G.F. et al eds. Academic Press, Inc. 57:47-85.

Tibbetts, C. (1977). "Viral DNA Sequences From Incomplete Particles of Human Adenovirus Type 7," *Cell* 12:243-249.

Van Olphen, A.L. et al. (2002). "A 72-bp Internal Deletion in the Left Inverted Terminal Repeat of the Bovine Adenovirus Type 3 Genome Does Not Affect Virus Replication," *Intervirology* 45:188-192.

Yamamoto, M. et al. (Jan. 2003). "Transcription Initiation Activity of Adenovirus Left-End Sequence in Adenovirus Vectors with E1 Deleted," *J. Virol.* 77(2):1633-1637.

Zakhartchouk, A.N. et al. (1998). "Construction and Characterization of E3-Deleted Bovine Adenovirus Type 3 Expressing Full-Length and Truncated Form of Bovine Herpesvirus Type 1 Glycoprotein gD," *Virology* 250:220-229.

Zhang, W. et al. (Mar. 2000). "Interaction of the Adenovirus IVa2 Protein with Viral Packaging Sequences," *J. Virol.* 74(6):2687-2690.

Zhang, W. et al. (Nov. 2001). "Role for the Adenovirus IVa2 Protein in Packaging of Viral DNA," *J. Virol.* 75(21):10446-10459.

Zheng, B. et al. (1994). "The E1 Sequence of Bovine Adenovirus Type 3 and Complementation of Human Adenovirus Type 5 E1A Function in Bovine Cells," *Virus Research* 31:163-186.

Zheng, B.J. et al. (Jul. 1999). "Transcription Units of E1a, E1b, and pIX Regions of Bovine Adenovirus Type 3," *J. Gen Virol.* 80(7):1735-1742.

Zhou, Y. et al. (2001). "Bovine Adenovirus Type 3 E1B$^{small}$ Protein Is Essential for Growth in Bovine Fibroblast Cells," *Virology* 288:264-274.

Zoller, M.J. et al. (1982). "Oligonucleotide-Directed Mutagenesis Using M13-Derived Vectors: An Efficient and General Procedure for the Production of Point Mutations in any Fragment of DNA," *Nucleic Acids Res.* 10(20):6487-6500.

Invitation To Pay Additional Fees issued for PCT Application No. PCT/IB2004/002409 mailed Mar. 18, 2005, seven pages.

Soudais, C. et al. (Apr. 2001), "Characterization of *cis*-Acting Sequences Involved in Canine Adenovirus Packaging," *Molecular Therapy* 3(4):631-640.

Xing, L. et al. (2003). "Identification of *cis*-Acting Sequences Required For Selective Packaging of Bovine Adenovirus Type 3 DNA," *Journal of General Virology* 84:2947-2956.

* cited by examiner

1A

| | | | | | | |
|---|---|---|---|---|---|---|
| 1 | CATCATCAAT | AATCTACAGT | ACACTGATGG | CAGCGGTCCA | ACTGCCAATC | ATTTTTGCCA |
| 61 | CGTCATTTAT | GACGCAACGA | CGGCGAGCGT | GGCGTGCTGA | CGTAACTGTG | GGGCGGAGCG |
| 121 | CGTCGCGGAG | GCGGCGGCGC | TGAGGGGCGG | GGGGCCGGCG | CGCGGGGCGG |
| 181 | CGGCGGGGGC | GGGGCGAGGG | GCGGAGTTCC | GCACCCGCTA | CGTCATTTC | AGACATTTT |
| 241 | TAGCAAATTT | GCGCCTTTG | CAAGCATTTT | TCTCACATTT | CAGGTATTTA | GAGGGCGGAT |
| 301 | TTTTGGTGTT | CGTACTTCCG | TGTCACATAG | TTCACTGTCA | ATCTTCATTA | CGGCTTAGAC |
| 361 | AAATTTCGG | CGTCTTTTCC | GGGTTTATGT | CCCCGGTCAC | CTTTATGACT | GTGTGAAACA |
| 421 | CACCTGCCCA | TTGTTTACCC | TTGGTCAGTT | TTTCGTCTC | CTAGGGTGGG | AACATCAAGA |
| 481 | ACAAATTTGC | CGAGTAATTG | TGCACCTTTT | TCCGCGTTAG | GACTGCGTTT | CACACGTAGA |
| 541 | CAGACTTTT | CTCATTTCT | CGTCCGCTTC | CGTCCGCTTC | AGAGCTCTGC | GTCTTCGCTG |
| 601 | CCACCATGAA | GTACCTGGTC | CTCGTTCTCA | ACGACGGCAT | GAGTCGAATT | GAAAAGCTC |

1B

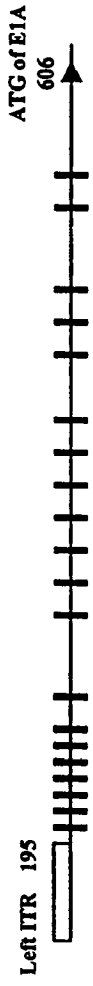

FIGURES 1A-1B

BAV PACKAGING REGIONS AND E1 TRANSCRIPTIONAL CONTROL REGIONS

CROSS REFERENCE TO RELATED APPLICATION

This application claims benefit of U.S. Provisional Patent Application Ser. No. 60/477,540, filed Jun. 10, 2003, which is incorporated by reference herein in its entirety.

FIELD OF THE INVENTION

The present invention is in the field of recombinant adenovirus vectors and relates to identification of bovine adenovirus packaging domains, E1 transcriptional control regions and E1A promoter. More particularly, it concerns recombinant adenovirus vectors which comprise a bovine adenoviral region(s) essential for viral encapsidation, and methods of making and using such adenovirus vectors. The present invention also relates to the identification of bovine adenovirus E1 transcriptional control regions and provides bovine adenovirus vectors comprising modification(s) in part or all of one or more E1 transcriptional control region(s), and methods of making and using such bovine adenovirus vectors.

BACKGROUND OF THE INVENTION

Adenovirus has been studied extensively for several decades since its initial description in the early 1950s. Adenovirus is receiving considerable attention in recent years for its potential use as a gene delivery vehicle in basic research, vaccination, and gene therapy protocols. Bovine adenoviruses (BAV) belong to the Mastadenovirus genus of the family Adenoviridae, and are involved in respiratory and enteric infections of calves (Mohanty et al., 1971, *Am. J. Vet. Res.* vol. 32:1899-1905). Bovine adenovirus type 3 (BAV-3) was first isolated by Darbyshire and coworkers in Britain from the conjunctiva of an apparently health cow (Darbyshire et al., 1965, *J. Comp. Patho.* Vol. 75:327-330). The complete DNA sequence of the BAV3 genome has been determined (Reddy et al. (1998, *J. Virol.* Vol. 72:1394-1402); Baxi et al. (1998, *Virus Genes* Vol. 16:313-316); and Lee et al., (1998, *Virus Genes*, Vol. 17:99-100)), and transcription maps of early region 1, 3 and 4 (E1, E3, E4), and late regions have been established (Reddy et al. (1999, *Virology* Vol. 253:299-308); Idamakanti et al. (1999, *Virology* Vol. 256:351-359); Baxi et al. (199 ,*Virology* Vol. 261:143-152); and Reddy et al. (1998, *J. Virol.* Vol. 72:1394-1402)). Replication-defective (Reddy et al. (1999, *J. Virol.* Vol. 73:9137-9144)) and replication-competent viral vectors (Zakhartchouk et al., 1998,*Virology* Vol. 250:220-229) have been disclosed. Bovine adenovirus systems are disclosed in U.S. Pat. Nos. 5,820,868; 6,001,591; 6,086,890; 6,458,586; and 6,319,716.

There remains a need for improved adenoviral vectors, especially adenoviral vectors for expression of transgenes in mammalian cells, and for the development of effective recombinant adenovirus vectors for use in immunization and expression systems.

All references and patent publications disclosed herein are hereby incorporated herein in their entirety by reference.

BRIEF SUMMARY OF THE INVENTION

The present invention relates to identification of bovine adenovirus packaging domains, E1 transcriptional control regions and E1A promoter. The present invention provides isolated bovine adenovirus (BAV) sequences essential for encapsidation comprising a sequence corresponding to the sequence located between nucleotides about 224 and about 540 relative to the left terminus of BAV-3, or a portion thereof capable of encapsidating an adenovirus genome. In some examples, the BAV sequence essential for encapsidation is located between nucleotides about 224 and about 540 relative to the left terminus of BAV-3, or a portion thereof capable of encapsidating an adenovirus genome. The present invention also provides recombinant vectors, such as adenovirus vectors, comprising one or more isolated bovine adenovirus sequence(s) essential for encapsidation. A recombinant vector may further comprise a modification of a part of or all of one or more bovine adenovirus E1 transcriptional control regions. In some examples, the adenovirus vector is a bovine adenovirus vector. In other examples, the adenovirus vector comprises a bovine adenovirus sequence(s) essential for encapsidation, wherein the bovine adenovirus sequence(s) essential for encapsidation is heterologous to said adenovirus vector. In yet further examples, said adenovirus vector (or adenovirus) comprises human adenovirus sequences, porcine adenovirus sequences, or canine adenoviral sequences. In further examples, an adenovirus or adenovirus vector comprises nucleic acid sequence encoding a heterologous protein, such as an antigen of a pathogen, and may additionally comprise an adenovirus inverted terminal repeat (ITR) sequence.

In further examples, an adenovirus vector comprises a bovine adenovirus sequence(s) essential for encapsidation and nucleic acid encoding a heterologous protein, wherein said adenovirus vector is deleted in part or all of one or more nucleic acid sequences encoding adenovirus proteins necessary for replication and/or part or all of one or more nucleic acid sequences encoding non-essential adenovirus proteins. In further examples, an adenovirus vector comprises human adenovirus sequences, bovine adenovirus sequences, porcine adenovirus sequences, and/or canine adenovirus sequences. In yet other examples, said heterologous protein encodes an immunogenic polypeptide, such as an antigen of a pathogen, such as for example an antigen of a human, bovine, porcine, canine or feline pathogen.

The present invention also provide recombinant bovine adenovirus vectors comprising a modification of a part of or all of one or more bovine adenovirus E1 transcriptional control region(s). In some examples, the modification is a deletion of part or all of one or more bovine adenovirus E1 transcriptional control region(s), and in other examples, is an addition of part or all of one or more bovine adenovirus E1 transcriptional control region(s). In further examples, the E1 transcriptional control region comprises from nucleotide about 224 to about 382 relative to the left terminus of BAV-3 genome. In other examples, the E1 transcriptional control region comprises from about nucleotide 537 to about nucleotide 560 relative to the left terminus of BAV-3 genome.

The present invention also provides expression systems, host cells, viral particles, compositions and vaccine compositions comprising adenovirus vectors comprising an isolated bovine adenovirus (BAV) sequence(s)essential for encapsidation comprising a sequence corresponding to the sequence located between nucleotides about 224 and about 540 relative to the left terminus of BAV-3, or a portion thereof capable of encapsidating an adenovirus genome, and/or a modification in a BAV E1 transcriptional control region (such as a deletion or addition of a BAV E1 transcriptional control region).

The present invention also provides compositions capable of inducing an immune response in a mammalian subject, said compositions comprising an adenovirus vector comprising an isolated bovine adenovirus (BAV) sequence(s) essential for encapsidation comprising a sequence corresponding to the sequence located between nucleotides about 224 and about 540 relative to the left terminus of BAV-3, or a portion thereof capable of encapsidating an adenovirus genome, and/or a modification in a BAV E1 transcriptional control region, and a pharmaceutically acceptable excipient. The present invention also provides methods for eliciting an immune response in a mammalian subject comprising administering a immunogenic composition encompassed within the present invention to the mammalian subject.

The present invention also provides methods of preparing adenovirus vectors and adenovirus comprising an isolated bovine adenovirus (BAV) sequence(s)essential for encapsidation comprising a sequence corresponding to the sequence located between nucleotides about 224 and about 540 relative to the left terminus of BAV-3, or a portion thereof capable of encapsidating an adenovirus genome, and/or a modification in a BAV E1 transcriptional control region.

BRIEF DESCRIPTION OF THE SEVERAL VIEWS OF THE DRAWING(S)

FIGS. 1A-1B. Nucleotide sequence (SEQ ID NO:1) and schematic diagram of BAV-3 left terminus. (A). Nucleotide sequence of BAV-3 left terminus. Inverted terminal repeat (ITR) nucleotide sequence is shown in italic. The ATG codon for E1A gene is shown in italic bold case (nt 606). AT-rich motifs are underlined. (B)Schematic diagram of BAV-3 left terminus. The ITR is shown by open box. AT-rich motifs are shown by filled box. The ATG codon of E1A gene is indicated with an arrow. The arrow also indicates the direction of transcription. Numbers indicate the nucleotide position relative to the left terminus of BAV-3 genome.

Figure 2B:
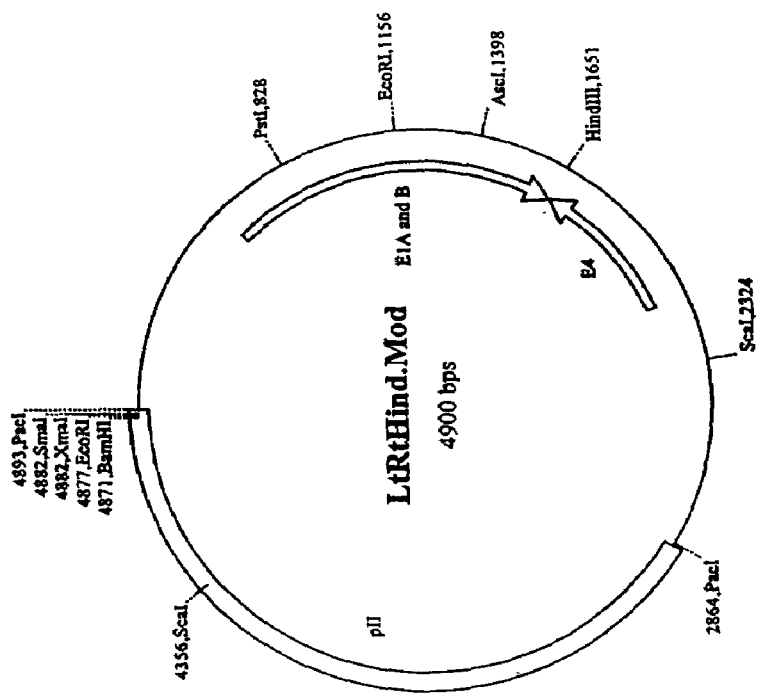
Figures 3A, 3B, 3C, 3D:
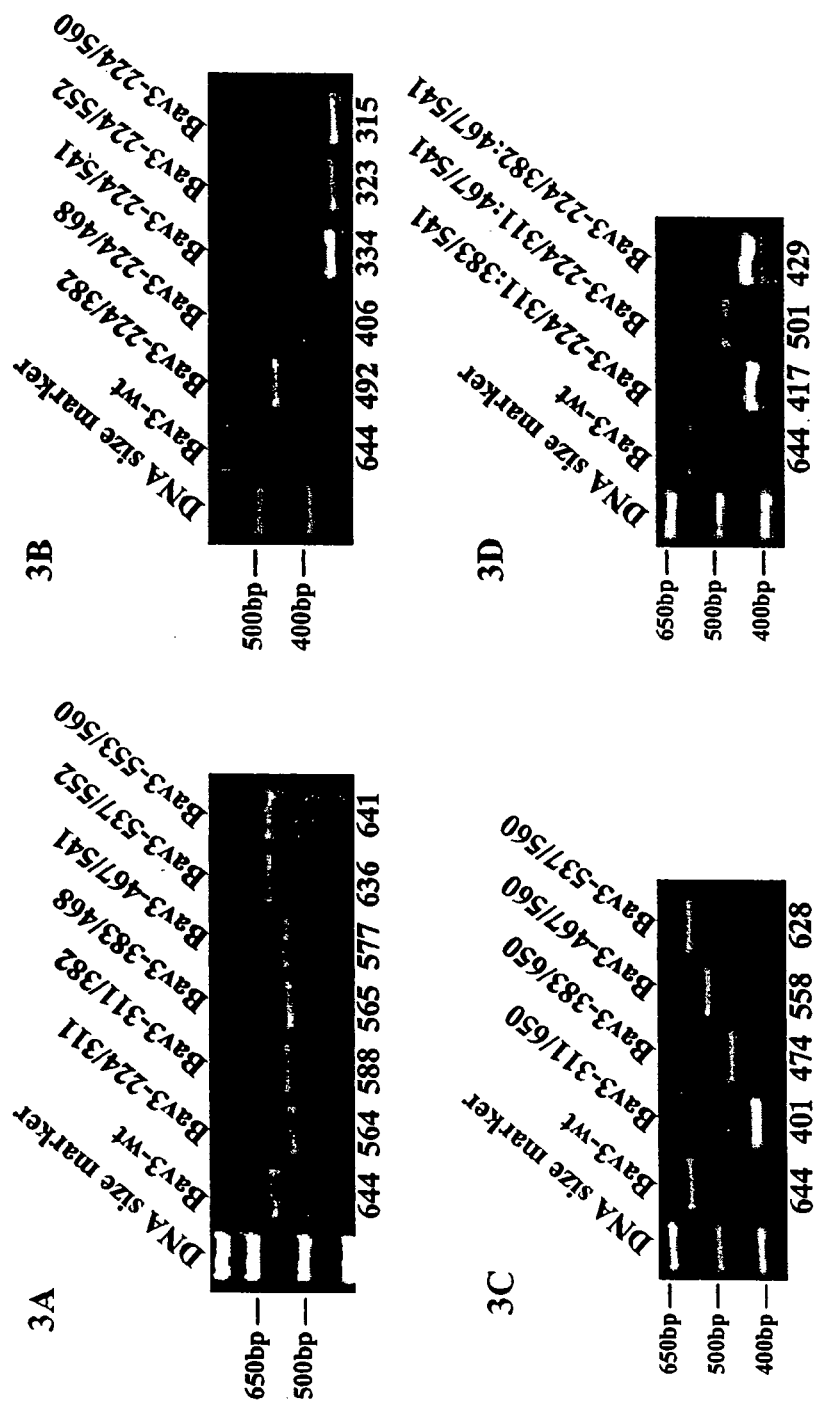

FIGS. 2A-2B. (A). Diagram of plasmid pLtRtHind.Mod used for generating deletion mutations. BAV-3 sequences are from the extreme left and right ends of the viral genome. The E1A and E4 mRNAs, and their directions of transcription are shown with open arrows. Plasmid backbone is designated with open box. (B). Schematic representation of the strategy used for the full-length plasmid and mutant virus construction. Thin line indicates the plasmid DNA. BAV-3 genomic DNA is indicated with boxes. ITR is shown by filled box. Hatched boxes represent region in which deletions were introduced.

FIGS. 3A-3D. PCR analysis of viral mutants. PCR products generated from mutant viruses are shown in comparison to that from wild-type BAV-3 by using primer pair PLB5 and LZP41. The expected sizes of PCR products are shown at the bottom. Molecular size markers are indicated on the left.

Figure 4A:
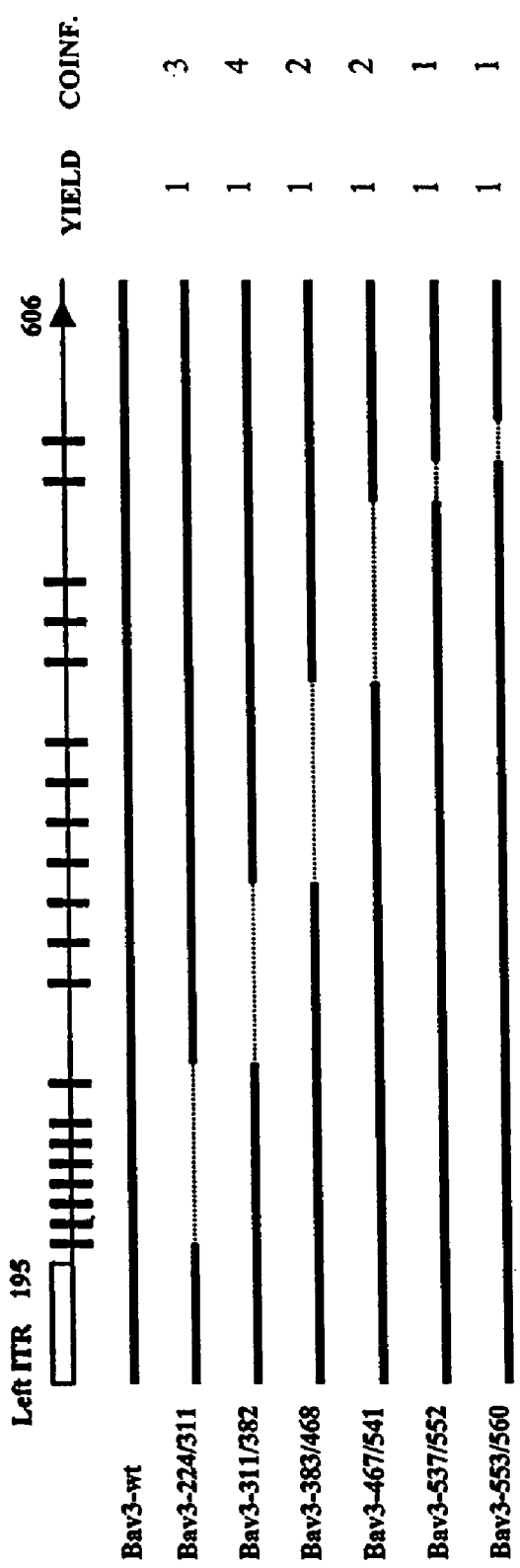
Figure 4B:
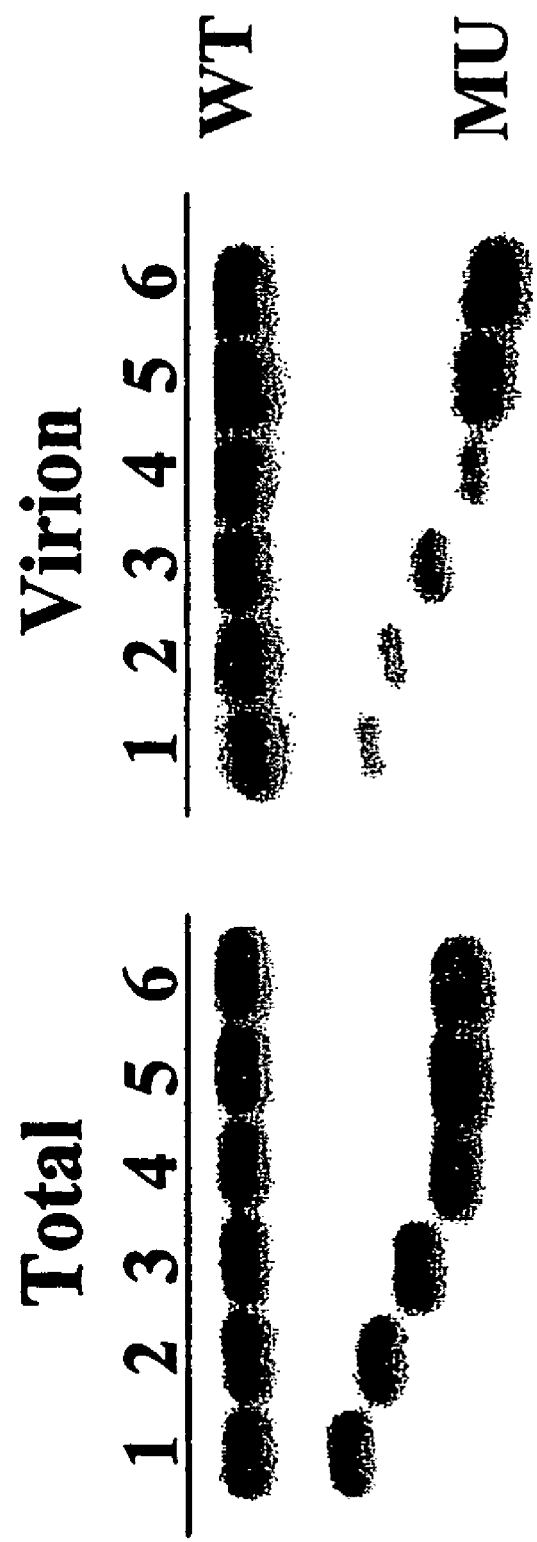

FIGS. 4A-4B. Analysis of viral mutants carrying individual deletions. (A) Schematic view of viral mutants. The top of the figure shows the position of AT rich motifs (filled box), E1A ATG (arrow head), and structure of the left terminus of BAV-3 genome. The individual deletion mutant names are given on the left. The nucleotide numbers correspond to the first nucleotides present on either side of the deletion. The deleted sequences are indicated by dotted line. Mutant virus yields (Yield) are expressed as the fold reduction in yield relative to that of wild-type virus. Mutant virus packaging efficiency (COINF) is expressed as the fold reduction in packaged mutant DNA relative to the packaged coinfecting wild-type DNA. The data were normalized to the amount of each viral DNA (mutant and wild-type) present in total nuclear DNA. (B) Southern hybridization analysis of total nuclear DNA and virion DNA isolated from VIDO R2 cells coinfected with wild-type and the mutant viruses. Total nuclear DNA and virion DNA were digested with XhoI and PstI, and subsequently subjected to Southern hybridization analysis using BAV-3 left end fragment between nt 560 and 839 as a $^{32}$P-labeled probe. The corresponding wild-type (WT) and mutant (MU) left end DNA fragments are indicated. The mutant viruses tested were Bav3-224/311(lane 1), Bav3-311/382(lane 2), Bav3-383/468 (lane 3), Bav3-467/541(lane 4), Bav3-537/552(lane 5), Bav3-553/560(lane 6).

Figure 5A:
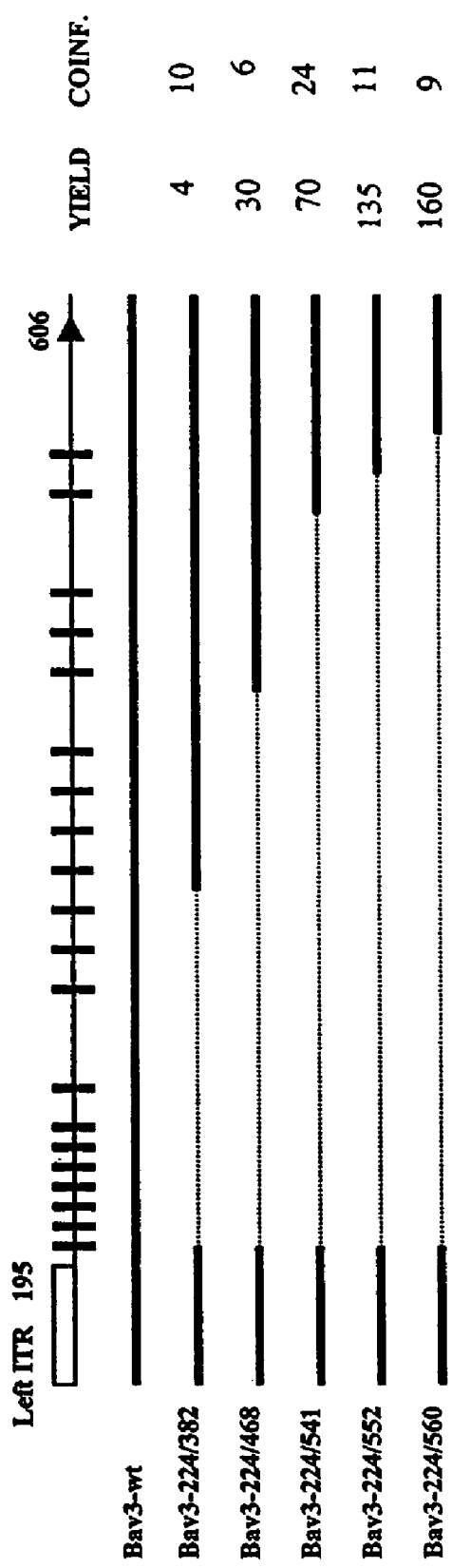
Figure 5:
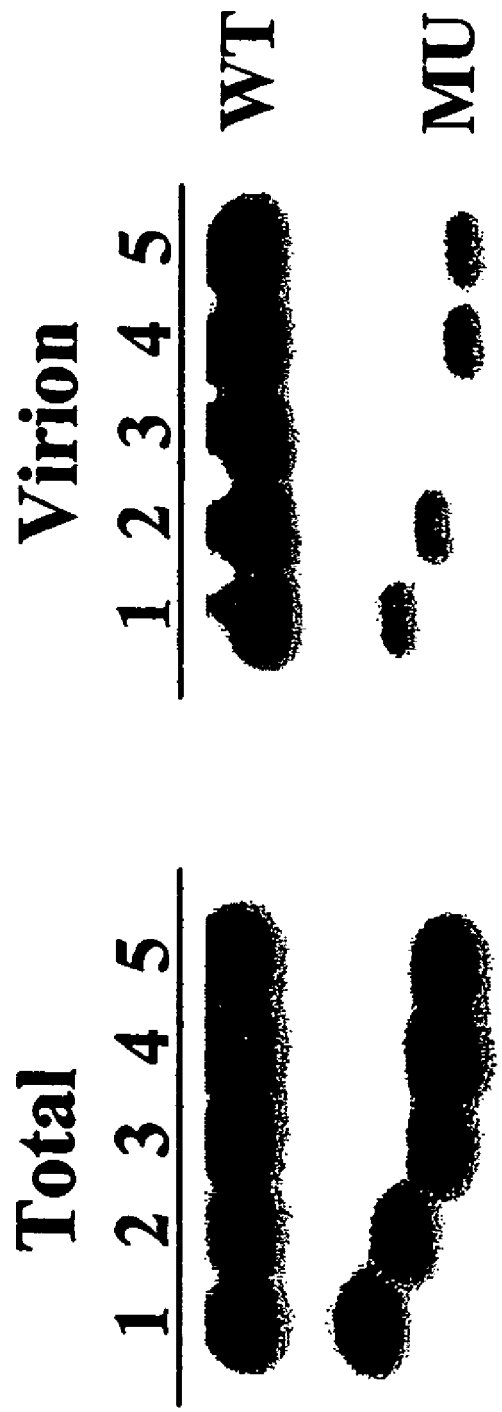

FIGS. 5A-5B. Analysis of viral mutants carrying progressive deletions with a common start site at nt 224. (A) The schematic view, mutant names, endpoints of the deletion, and in vivo packaging analysis are as described in the legend to FIG. 4A. (B) Southern hybridization analysis of nuclear and virion DNA isolated from VIDO R2 cells coinfected with wild-type and individual mutant viruses. Southern hybridization analysis was performed as described in the legend to FIG. 4B. The mutant viruses tested were Bav3-224/382(lane 1), Bav3-224/468(lane 2), Bav3-224/541(lane 3), Bav3-224/552(lane 4), Bav3-224/560(lane 5).

Figure 6A:
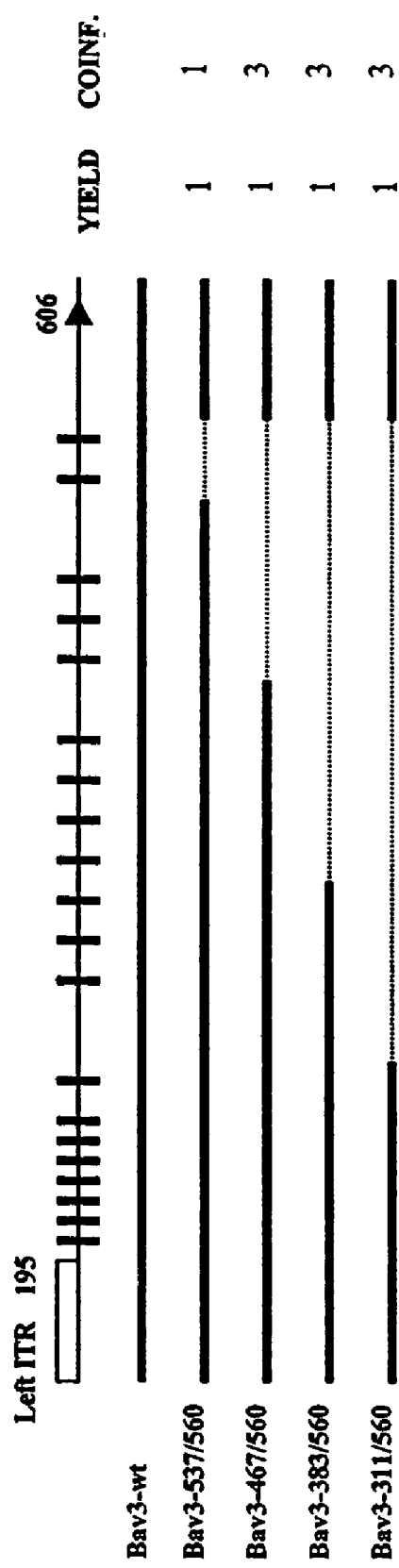
Figure 6B:
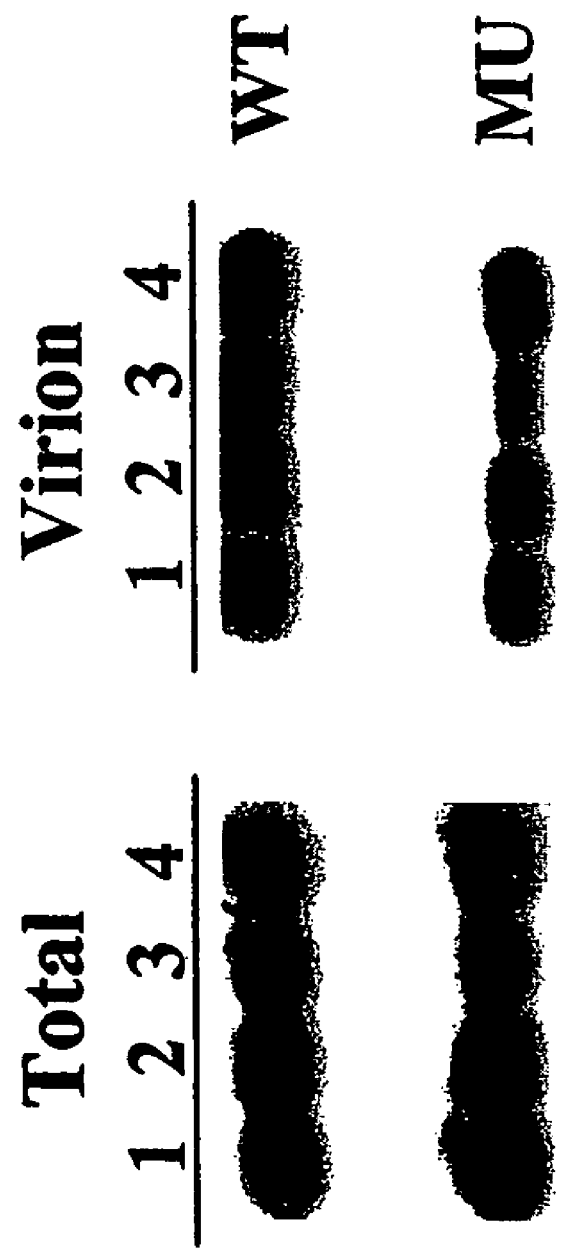

FIGS. 6A-6B. Analysis of viral mutants carrying progressive deletions with a common start site at nt 560. (A) The schematic view, mutant names, endpoints of the deletion, and in vivo packaging analysis are as described in the legend to FIG. 4A. (B) Southern hybridization analysis of nuclear and virion DNA isolated from VIDO R2 cells coinfected with wild-type and individual mutant viruses. Southern hybridization analysis was performed as described in the legend to FIG. 4B. The tested viruses were Bav3-537/560 (lane 1), Bav3-467/560 (lane 2), Bav3-383/560 (lane 3), Bav3-311/560 (lane 4).

Figure 7A:
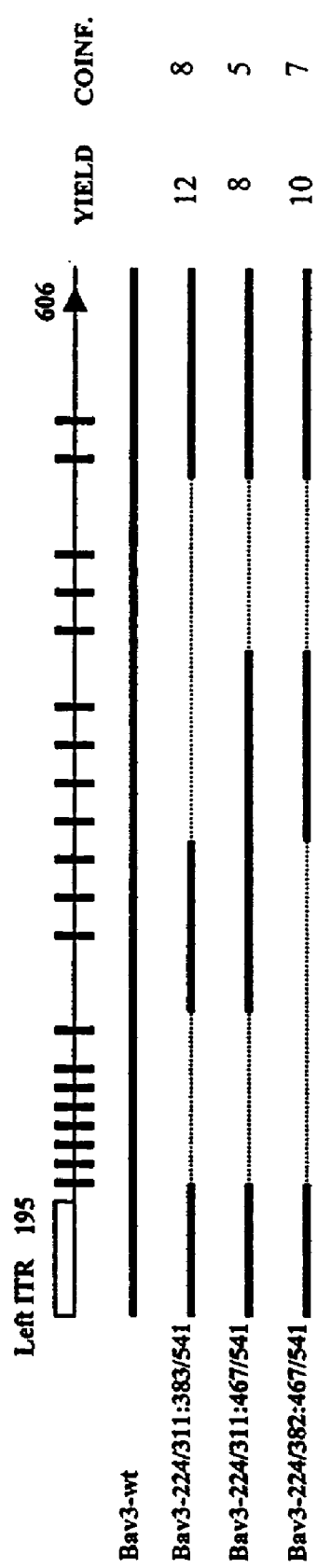
Figure 7B:
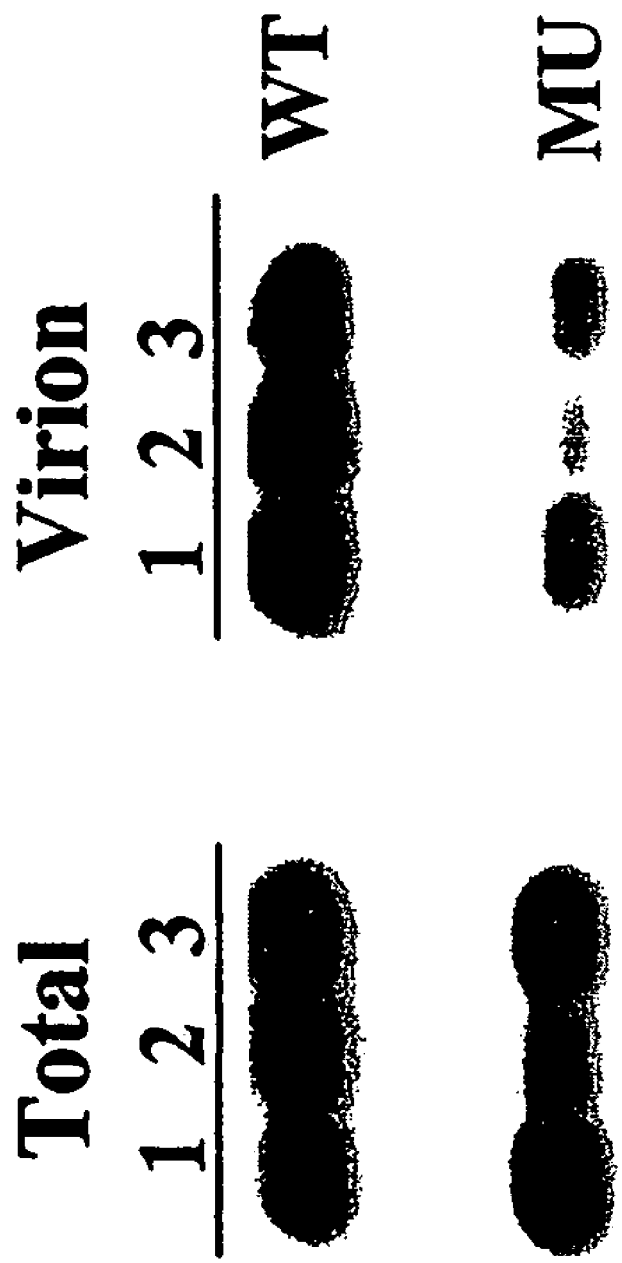

FIGS. 7A-7B. Analysis of viral mutants carrying double deletions. (A) The schematic view, mutant names, endpoints of the deletion, and in vivo packaging analysis are as described in the legend to FIG. 4A. (B) Southern hybridization analysis of nuclear and virion DNA isolated from VIDO R2 cells coinfected with wild-type and individual mutant viruses. Southern hybridization analysis was performed as described in the legend to FIG. 4B. The mutant viruses tested were Bav3-224/311:383/541 (lane 1), Bav3-224/311:467/541 (lane 2), Bav3-224/382:467/541 (lane 3).

Figure 8:
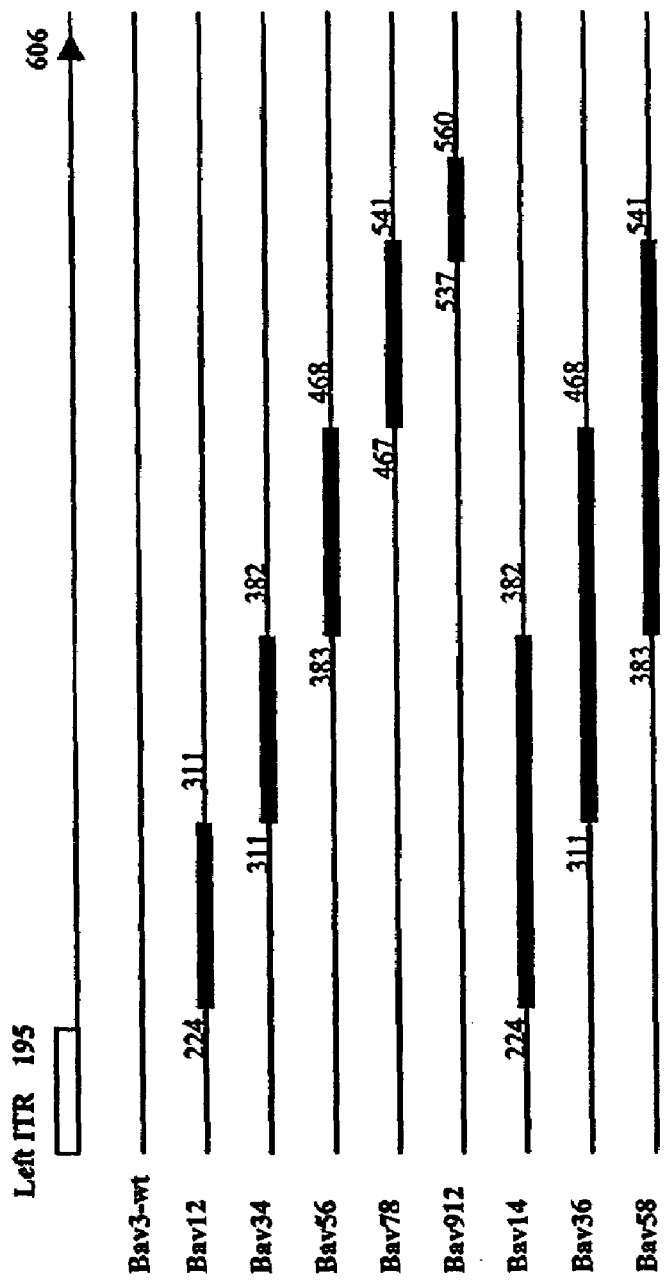

FIG. 8. Schematic diagram of mutant viruses. The individual deletion mutant names are given on the left. The deleted sequences are indicated with the bold lines. Nucleotide numbers relative to the left terminus of the BAV-3 genome designate the last base pair present on either side of deletions.

FIGS. 9A-9F. Northern blot analysis of E1A(A), E1B(B), E2A(C), E3(D), and E4(E) mRNAs produced in virus-infected MDBK cells at 7 h after infection. MDBK cells were infected with wild-type or mutant BAV-3 at a MOI of 40 PFU per cell, and maintained in MEM containing 125 µg/ml AraC. The RNA was isolated 7 h late and then subjected to Northern blot analysis using $^{32}$P-labeled probes corresponding to nt 560-1156 (A), nt 1398-1651 (B), nt 21283-22576 (C), nt 27273-27959 (D), and nt 33232-33905 (E). As a control (F), the RNAs stained with ethidium bromide in denaturing formaldehyde agarose gel were photographed. 18s and 28s rRNAs were indicated.

Figures 10A, 10B:
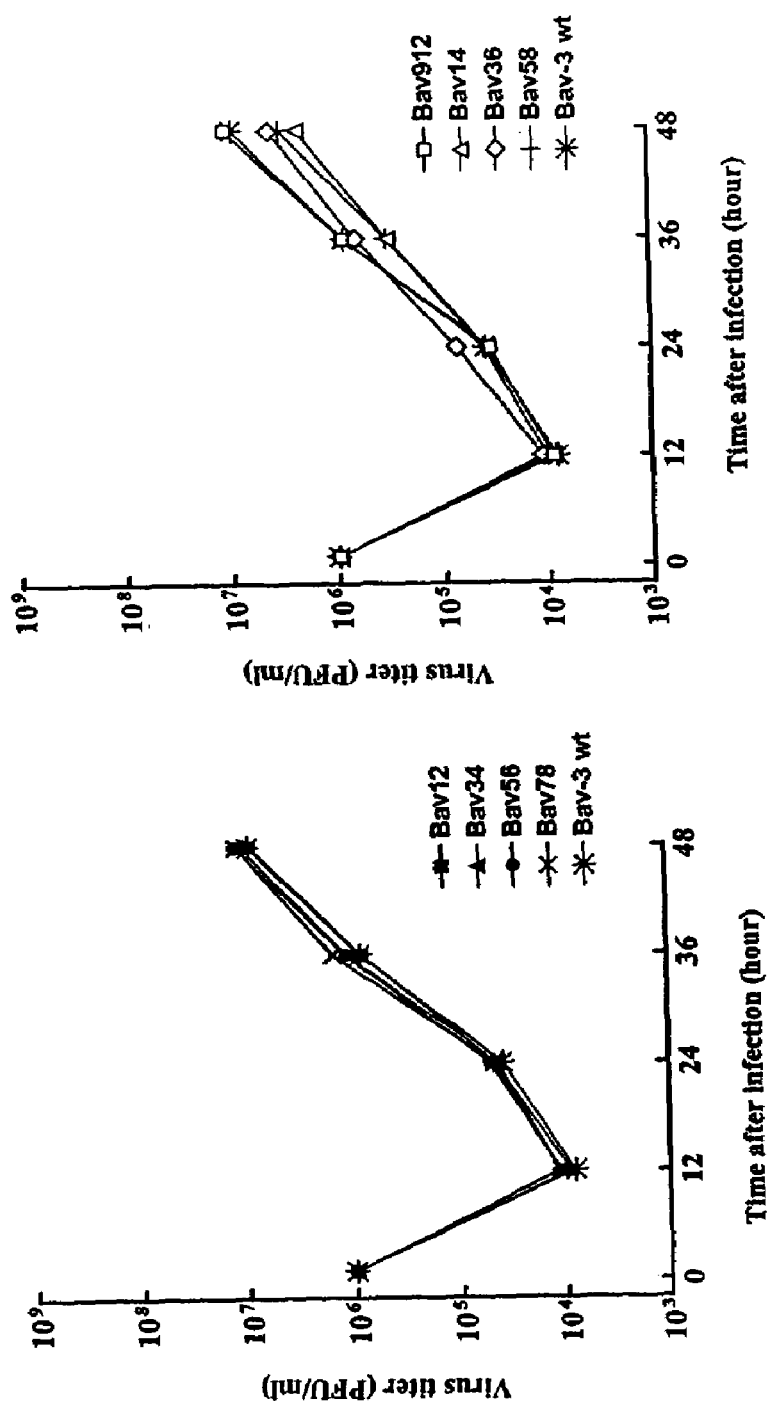

FIGS. 10A-10B. Growth kinetics of mutant viruses on VIDO R2 (A) and MDBK (B) cells. The cells were infected with the indicated viruses at a MOI of 5 PFU per cell. Lysates were harvested at 12, 24, 36, and 48 h after infection. The PFU titers were determined by plaque assay on VIDO R2 cells, and the averaged values plus Standard Deviation (SD) are plotted and represented as PFU/ml. The growth curves are distinguished by symbols indicated on the right.

Figure 11B:
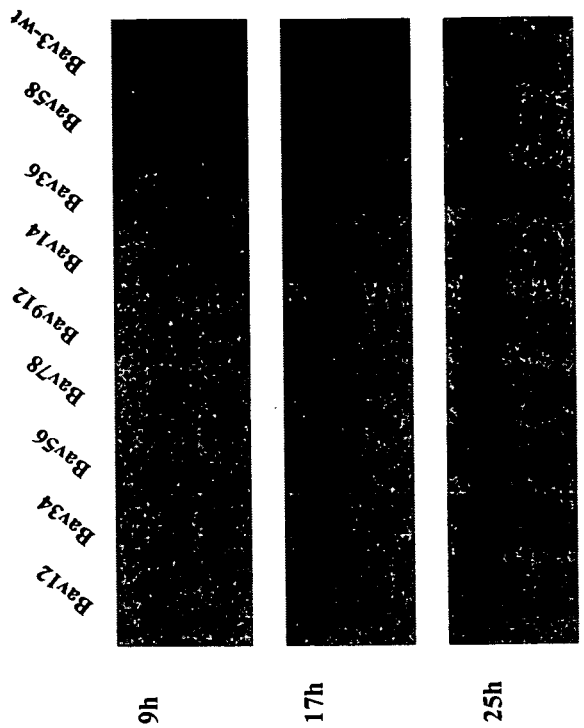
Figure 11A:
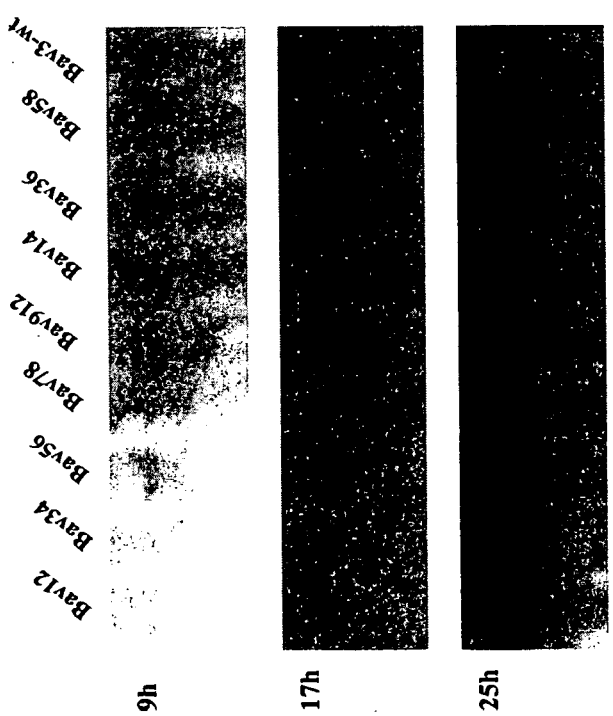

FIGS. 11A-11B. Viral DNA accumulation in VIDO R2 (A) and MDBK (B) cells. The cells were infected with the indicated viruses at a MOI of 5 PFU per ml. DNAs were prepared at 9, 17, and 25 h after infection. After digestion with EcoRI, the agarose gel fractionated DNAs were subjected to Southern blot analysis using $^{32}$P-labeled probes corresponding to the sequences between nt 828-1651 of BAV-3 genome.

Figure 12:
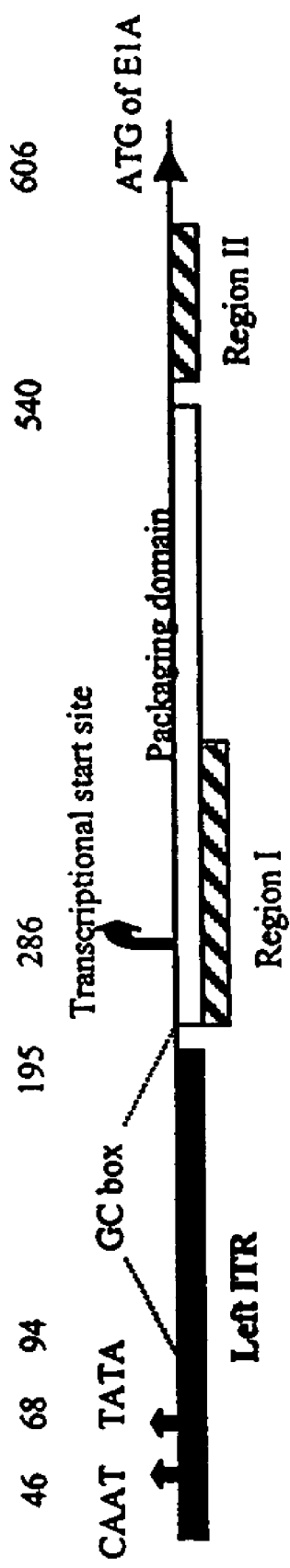

FIG. 12. Prediction of E1A promoter and proposed structure of the BAV-3 left end genome. The left ITR is shown by filled box. The 5'-flanking sequences of BAV-3 E1A ORF are shown by thin line. Cis-acting packaging domain and transcriptional regulation regions (I and II) are shown by open box and hatched boxes, respectively. Major transcriptional start site and start ATG codon of E1A, GC-rich sequences, and predicted core elements (CAAT box and TATA box) of E1A promoter are indicated. The numbers designate the nucleotide positions relative to the left terminus of BAV-3 genome.

DETAILED DESCRIPTION OF THE INVENTION

The present invention relates to identification of bovine adenovirus packaging domains, E1 transcriptional control regions and E1A promoter. The assembly of adenovirus particles is a multiple step process in which the viral genomic DNA is selected and subsequently inserted into preformed, empty capsids. The selective encapsidation of adenovirus genome is directed by cis-acting packaging domains which are termed "A repeats" due to their AT-rich character in DNA sequences, and are usually located at the left end of viral genome. Based on analysis of genomic DNA sequences of bovine adenovirus type 3 (BAV-3), twenty AT-rich units were found in the interval between the left Inverted Terminal Repeat (ITR) and start ATG codon of open reading frame (ORF) of early region 1A (E1A) gene. Data disclosed herein demonstrate that the main cis-acting packaging domains of BAV-3 are localized between nucleotide (nt) position about 224 and about 540 relative to the left end of viral genome (shown in FIGS. 1A-1B.) Based on the construction of BAV3 deletion mutants described herein, the identified packaging domains displayed a functional redundancy and followed a hierarchy of importance.

Accordingly, the present invention relates to the identification of bovine adenovirus (BAV) regions essential for encapsidation and to recombinant adenoviral vectors and virus particles, which comprise one or more isolated BAV sequence(s) essential for encapsidation. The present invention also relates to vectors, expression systems, host cells and compositions, including vaccine compositions, comprising adenovirus vectors which comprise one or more isolated BAV sequence(s) essential for encapsidation. An adenovirus vector comprising an isolated BAV sequence essential for encapsidation is used in a helper virus for propagating recombinant adenovirus. An adenovirus vector comprising an isolated BAV sequence essential for encapsidation is used in a recombinant adenovirus vector for propagation purposes. In some examples, an adenovirus vector comprising one or more isolated BAV sequence(s) essential for encapsidation is used to propagate a virus and/or produce a heterologous protein, such as an antigen of a pathogen. In other examples, an adenovirus vector comprising one or more isolated BAV sequence(s) essential for encapsidation is used to elicit an immune response in an individual. In other examples, an adenovirus vector comprising one or more isolated BAV region(s) essential for encapsidation is used to deliver a heterologous protein to an individual.

The present invention also relates to the identification of bovine adenovirus E1 transcriptional control regions. As described herein, two functionally separate bovine adenovirus E1 transcriptional control regions are identified. Bovine adenovirus E1 transcriptional control region I is located between nucleotide position about 224 and about 382 relative to the left terminus of BAV-3 genome and overlaps the cis-acting packaging domains. Bovine adenovirus E1 transcriptional control region II is located between nucleotide position about 537 and about 560 relative to the left terminus of BAV-3 genome.

Accordingly, the present invention relates to the identification of bovine adenovirus (BAV) E1 transcriptional regions and to recombinant adenoviral vectors which comprise a modification of part or all of one or more E1 transcriptional region(s). The present invention also relates to vectors, expression systems, host cells and compositions, including vaccine compositions, comprising adenovirus vectors which comprise a modification of part or all of one or more E1 transcriptional region (s). An adenovirus vector, such as a BAV, comprising a modification of a bovine adenovirus E1 transcriptional control region is used in a helper virus for propagating recombinant adenovirus, such as a BAV. Such an adenovirus is used to propagate a virus and produce a heterologous protein, such as an antigen of a pathogen. In other examples, an adenovirus vector, such as a BAV, comprising a modification in one or more bovine adenovirus E1 transcriptional control region(s) is used to elicit an immune response in an individual (such as a mammal) or to deliver a heterologous protein to an individual (such as a mammal).

The present invention also relates to the identification of the E1A promoter as disclosed herein.

The practice of the present invention will employ, unless otherwise indicated, conventional microbiology, immunology, virology, molecular biology, and recombinant DNA techniques which are within the skill of the art. These techniques are fully explained in the literature. See, e.g., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984). Samnbrook et al., Molecular Cloning: A Laboratory Manual (2 nd Edition); vols. I, II & III (1989).

For general information related to mammalian adenovirus see "Fundamental Virology", second edition, 1991, ed. B. N. Fields, Raven Press, New York, pages 771-813; and "Fields Virology", third edition, 1995, ed. B. N. Fields, vol. 2, pages 2111-2172.

As used herein, "region(s) essential for encapsidation", an "encapsidation region", "sequence(s) essential for encapsidation", an "encapsidation sequence" and a "packaging domain" or "packaging motif" (used interchangeably herein) refer to the sequence(s) of an adenovirus genome that is/are necessary for inserting the adenovirus genome (DNA) into adenovirus capsids. In some examples, an encapsidation sequence is cis-acting. A "bovine adenovirus" sequence essential for encapsidation encompasses any bovine adenovirus sequence essential for encapsidation as long as the sequence is capable of inserting the adenovirus genome (DNA) into adenovirus capsids. In some examples, a bovine adenovirus sequence essential for encapsidation is a BAV-3 sequence. Illustrative examples of BAV-3 encapsidation sequences are disclosed herein. As used herein, the phrase, "bovine adenovirus sequence(s) essential for encapsidation that is heterologous to the adenovirus vector", means that the adenovirus vector sequence is a non-bovine adenovirus sequence or the adenovirus vector sequence is a bovine adenovirus sequence of a different serotype than the bovine adenovirus sequence essential for encapsidation. In some examples, the non-bovine adenovirus sequences are mammalian including but not limited to human, porcine, ovine, canine or feline sequences. Human, porcine, ovine, canine and feline adenovirus sequences are known to those of skill in the art. The heterologous adenovirus vector sequences are not limited and can be any adenovirus sequence as long as the bovine adenovirus sequence(s) essential for encapsidation can function to insert the adenovirus genome (DNA) into an adenovirus capsid. In some examples, an isolated bovine adenoviral sequence(s) essential for encapsidation is used in an adenovirus vector that comprises bovine adenovirus sequences (for example, of the same serotype). An adenovirus vector may be constructed to comprise multiple isolated bovine adenovirus sequences essential for encapsidation, for example, multiple identical sequences or multiple different sequences, or the isolated bovine adenovirus vector encapsidation sequence may be heterologous, i.e. of a different serotype, to the adenovirus vector comprising bovine adenovirus sequences. The present invention encompasses an adenovirus vector comprising one or more BAV3 encapsidation sequence(s) and one or more human adenovirus sequence(s). An adenovirus vector may comprise one or more isolated bovine adenovirus sequence(s) essential for encapsidation. In examples where the adenovirus comprises more than one isolated bovine adenovirus sequence(s) essential for encapsidation, the sequences can be the same or different. All BAV3 nucleotide numbering is with respect to the left end of the adenovirus and the BAV3 reference sequence is provided in GenBank accession number AF030154. A bovine adenovirus sequence corresponding to the BAV-3 encapsidation sequence located between about nucleotides 224 and about 540 relative to the left terminus of BAV-3, refers to a nucleic acid sequence that has at least 80%, at least 85%, at least 90%, at least 95%, at least 97%, at least 98% or at least 99% identity to at least 5, at least 10, at least 15, at least 20, at least 25, at least 30, at least 35, 40, at least 45, at least 50, at least 55, at least 60, at least 65, at least 70, at least 75, least 85, at least 90, at least 95, at least 100, at least 150 or at least 200 consecutive nucleic acids of the BAV-3 encapsidation sequence located between about nt 224 and about nt 540 relative to the left terminus of BAV-3 (as disclosed herein), and is capable of encapsidating a mammalian adenovirus and/or is located at the left end of an adenovirus and comprises AT-rich sequences and is capable of encapsidating a mammalian adenovirus. Assays for determining encapsidation of an adenovirus genome are disclosed herein. The present invention encompasses vectors, such as viral vectors, comprising portions or fragments of the BAV-3 encapsidation sequence located between about nt 224 and about nt 540 relative to the left terminus of BAV-3 (as disclosed herein), as long as the portion or fragment is capable of encapsidating a mammalian adenovirus. A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18, Table 7.7.1. One alignment program for measuring identity is ALIGN Plus (Scientific and Educational Software, Pennsylvania), using default parameters, which are as follows: mismatch=2; open gap=0; extend gap=2.

Under "transcriptional control" is a term well understood in the art and indicates that transcription of a polynucleotide sequence, usually a DNA sequence, can in some examples depend on its being operably (operatively) linked to an element which contributes to the initiation of, or promotes, transcription and in other examples, can act from a distance away, such as the case with enhancers. The adenovirus E1 transcriptional control regions described herein appear to act as enhancers and do not need to be operably linked to a promoter (or other control element) and can work, that is, operate, at a distance from the promoter (or other control element) of the gene of interest. "Operably linked" refers to a juxtaposition wherein the elements are in an arrangement allowing them to function. The present invention provides isolated BAV E1 transcriptional control regions including nucleotides from between about 224 to about 382 relative to the left terminus of BAV-3 genome, which overlap the cis-acting packaging domains (referred to herein as "transcriptional control region I" or "Region I") and nucleotides from about 537 to about 560 relative to the left terminus of BAV-3 genome (Region II). All BAV-3 nucleotides are with respect to the reference sequence GenBank accession number AF030154. The left terminus of BAV3 is shown in Figs 1A-1B (SEQ ID NO:1). Additional bovine adenovirus (BAV) E1 transcriptional control regions can be identified based on the sequence similarity with, i.e. sequence identity to (measured as disclosed herein), and/or location of BAV3 E1 transcriptional control regions disclosed herein. The present invention encompasses BAV and BAV vectors comprising a modification of one or more E1 transcriptional control regions, wherein the modification can be a deletion of and/or addition of part or all of one or more E1 transcriptional control regions, such as the BAV-3 E1 transcriptional control regions identified herein. The present invention encompasses BAV and BAV vectors comprising part of or all of one or more additional isolated bovine adenovirus E1 transcriptional control regions (in addition to any naturally occurring E1 transcriptional control regions present in the vector) wherein the additional sequence (region) can be the same E1 transcriptional control region or a different E1 transcriptional control region(s) than the E1 transcriptional control region naturally occurring in the vector. A bovine adenovirus E1 transcriptional control sequence corresponding to the BAV-3 E1 transcriptional control regions as used herein refers to a nucleic acid sequence that has at least 80%, at least 85%, at least 90%, at least 95%, at least 97%, at least 98% or at least 99% identity to a BAV-3 E1 transcriptional control region (that is Region I and Region II) disclosed herein and retains at least one activity (such as, for example, the ability to modulate transcription of E1) of the BAV3 E1 transcriptional control region.

An "adenovirus vector" or "adenoviral vector" (used interchangeably) comprises a polynucleotide construct of the invention. A polynucleotide construct of this invention may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a nonviral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A "gene" refers to a coding region of a polynucleotide. A "gene" may or may not include non-coding sequences and/or regulatory elements.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) *Nucleic Acids Res*. 24: 1841-8; Chaturvedi et al. (1996) *Nucleic Acids Res*. 24: 2318-23; Schultz et al. (1996) *Nucleic Acids Res*. 24: 2966-73. A phosphorothioate linkage can be used in place of a phosphodiester linkage. Braun et al. (1988) *J. Immunol*. 141: 2084-9; Latimer et al. (1995) *Molec. Immunol*. 32: 1057-1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence also includes the complement sequence.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

In the context of adenovirus, a "heterologous polynucleotide" or "heterologous gene" or "transgene" is any polynucleotide or gene or transgene that is not present in wild-type adenovirus. Preferably, the transgene will also not be expressed or present in the target cell prior to introduction by the adenovirus vector. Examples of preferred transgenes are provided herein.

In the context of adenovirus, a "heterologous" promoter is one which is not associated with or derived from an adenovirus gene.

In the context of an adenoviral vector, "inactivating" a viral function or a vector "lacking" a viral function means that there is a mutation of nucleic acid encoding the viral protein (e.g. for example, a point mutation, a deletion in part or all of the nucleic acid encoding the viral protein, an insertion within the nucleic acid encoding the viral protein), which reduces, disables or inactivates the viral protein function.

A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

An "individual" or "mammalian subject" is a vertebrate, such as a mammal, including, but are not limited to, farm animals, such as bovine, porcine, ovine; sport animals, such as equine; rodents; primates such as humans; and pets such as feline and canine.

An "effective amount" is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

By "live virus" is meant, in contradistinction to "killed" virus, a virus which is capable of producing identical progeny in tissue culture and inoculated animals.

A "helper-free virus vector" is a vector that does not require a second virus or a cell line to supply something defective in the vector.

"Bovine host" refers to cattle of any breed, adult or infant.

The term "protein" is used herein to designate a polypeptide or glycosylated polypeptide, respectively, unless otherwise noted. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

The term "isolated" as used herein means that the nucleic acid or amino acid sequence is removed from at least one component with which it is naturally associated.

An "antigen" refers to a molecule containing one or more epitopes that will stimulate a host's immune system to make a humoral and/or cellular antigen-specific response. The term is also used interchangeably with "immunogen."

The term "epitope" refers to the site on an antigen (or hapten) to which a specific antibody molecule binds or is recognized by T cells. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The terms "immunogenic polypeptide" or "immunogenic amino acid sequence" or "immunogenic composition" refer to a polypeptide or amino acid sequence or composition, respectively, which elicit antibodies that neutralize viral infectivity, and/or mediate antibody-complement or antibody dependent cell cytotoxicity to provide protection of an immunized host. An "immunogenic polypeptide" as used herein, includes the full length (or near full length) sequence of the desired protein or an immunogenic fragment thereof.

By "infectious" is meant having the capacity to deliver the viral genome into cells.

"Expression" includes transcription and/or translation.

As used herein, the term "comprising" and its cognates are used in their inclusive sense; that is, equivalent to the term "including" and its corresponding cognates.

"A," "an" and "the" include plural references unless the context clearly dictates otherwise.

Bovine Adenovirus Encapsidation Sequences.

The assembly of human adenovirus virions has been studied by using a large number of temperature-sensitive virus mutants blocked at different stages of assembly at the restrictive temperature and pulse-chase kinetics analysis (D'Halluin et al. (1978, *J. Virol.* Vol. 26:357-363); D'Halluin et al. (1978, *J. Virol.* Vol. 26:344-356); D'Halluin et al. (1980, *J. Virol.*Vol. 33:88-99); Edvardsson et al. (1976, *J. Virol.* Vol. 19:533-547); and Edvardsson et al. (1978, *J. Virol.* Vol. 25:641-651)). This is a multistep process and starts with polymerization of the hexon proteins to form the capsomes, which join with other structural proteins, including the penton base and fiber proteins, to form empty capsids. Without being bound by theory, it is believed that the viral genome, which is a linear double-stranded DNA molecule with preterminal protein attached to both ends, is inserted into the capsids along with other core proteins, followed by a final maturation step mediated by the viral protease (D'Halluin et al., 1995, *Curr. Top. Microbiol. Immunol.* Vol. 199:47-66). It has been established that the selective packaging of adenovirus genome into preformed empty capsids late in the infectious viral life cycle involves the specific recognition of cis-acting viral DNA sequences named the packaging domain(s) (Grable et al. (1990, *J. Virol.* Vol. 64:2047-2056); Daniell et al. (1976, *J. Virol.* Vol. 19:685-708); Hammarskjoeld et al. (1980, *Cell* Vol. 20:787-795); Hearing et al. (1987, *J. Virol.* Vol. 61:2555-2558); Robinson et al. (1984, *Virology* Vol. 137:276-286); Tibbetts et al. (1977, *Cell* Vol. 12:243-249)).

Human adenovirus genomes are known in the art. The complete genome sequence of human adenovirus 5 is disclosed in GenBank accession number M73260 and the complete genome sequence of human adenovirus 2 is disclosed in GenBank accession number J01917, the sequences of which are incorporated herein by reference. The cis-acting packaging domain of human adenovirus (HAV) has been characterized. (Hearing et al. (1987, supra); Grable et al. (1990, supra); Grable et al. (1992, *J. Virol.* Vol. 66:723-731); Schmid et al. (1997, *J. Virol.* Vol. 71:3375-3384)). It is usually located at the left end of viral genome between approximately nucleotide position (nt) about 194 and about 380 (Daniell et al. (1976, supra); Hammarskjoeld et al. (1980, supra); Hearing et al. (1987, supra); Robinson et al. (1984, supra); Tibbetts et al. (1977, supra)). This region contains at least seven functionally redundant elements termed A repeat I through VII (AI, AII, AIII, AIV, AV, AVI, and AVII) due to their AT-rich character with AI, AII, AV, and AVI being the most dominant. AI, AII, AV, and AVI exhibit a bipartite concensus motif 5'-TTTGN$_8$CG-3', which is conserved across a number of adenovirus serotypes, and can function independently (Schmid et al. (1997, *J. Virol.* Vol. 71:3375-3384)). In addition, the spacing constraints were observed between the two conserved parts (TTTG and CG) of this bipartite concensus motif rather than between different A repeats. In addition to cis-acting sequences, a number of viral and/or cellular proteins are thought to be involved in adenovirus DNA packaging. Schmid and Hearing (1998, *J. Virol.* 72:6339-6347) have detected some cellular proteins binding to the packaging sequences. Among viral proteins, the 52/55-kDa and IVa2 proteins have been shown to be required for viral DNA packaging (Zhang et al. (2000, *J. Virol.* 74:2687-2690); Gustin, et al. (1998, *J. Virol.* 72:7860-7870)). Interaction of IVa2 with the different components of the DNA packaging machinery has been shown to be serotype specific (Zhang et al. (2001, *J. Virol.* 75:10446-10459)).

The complete DNA sequence of the BAV-3 genome is disclosed in Reddy et al. (1998, *J. Virol.* Vol. 72:1394-1402); Baxi et al. (1998, *Virus Genes* Vol. 16:313-316); and Lee et al. (1998, *Virus Genes* Vol. 17:99-100). Transcriptional maps of early region 1, 3 and 4 (E1, E3 and E4) and late regions are disclosed in (Reddy et al. (1999, *Virology* Vol. 253:299-308); Idamakanti et al. (1999, *Virology* Vol. 256: 351-359); Baxi et al. (1999, *Virology* Vol. 261:143-152); and Reddy et al. (1998, *J. Virol.* Vol. 72:1394-1402)). BAV expression and vaccine systems are disclosed in U.S. Pat. Nos. 5,820,868; 6,001,591; 6,086,890; 6,458,586; and 6,319,716. The canine adenovirus genome has been published as GenBank accession number U77082.

Due to the similarity of genome organization between HAV-5 and BAV-3, to search the packaging domain of BAV-3, the left end region of BAV-3 genome was reviewed, especially between left ITR and the start ATG codon of E1 A open reading frame (ORF), shown in (FIGS. 1A-1B). According to the consensus bipartite structure of the dominant cis-acting packaging elements, 5'-TTTGN$_8$CG-3'(SEQ ID NO:2), and/or AT-rich character described for HAV-5, 20 AT-rich units were found between nucleotides (nt) about 224 and about 560. However, none of them show a perfect homology with 5'-TTTGN$_8$CG-3'(SEQ ID NO:2) sequences. Deletion mutations were introduced into this region on the BAV-3 viral genome, and then the virus mutants were analyzed for packaging efficiency. The present invention relates to the characterization of the BAV regions essential for encapsidation, also referred to herein as "packaging domains" and provides isolated BAV packaging domains as well as adenovirus vectors comprising such packaging domains. Data shown herein in the Examples demonstrate that the main cis-acting packaging domains of BAV-3 are localized between about nucleotide 224 and about nucleotide 540 relative to the left end of the adenovirus genome. Additional bovine adenovirus packaging domains can be identified based on sequence similarity with and/or location of the BAV3 encapsidation sequences disclosed herein. Potential bovine adenovirus encapsidation sequences can be assayed by constructing deletion mutations in and around the identified sequences and analyzing for packaging efficiency by methods known in the art and disclosed herein, for example by determining the viral titer of the expression of a reporter gene.

The present invention encompasses isolated BAV regions essential for encapsidation, such as the BAV-3 encapsidation sequence(s) disclosed herein located between about nt 224 and about nt 540 as shown herein in FIGS. 1A-1B (SEQ IID NO:1); vectors, such as, adenovirus vectors, and viral particles, comprising one or more isolated bovine adenovirus sequence essential for encapsidation, as well as bovine adenovirus vectors comprising isolated bovine encapsidation sequences, in addition to naturally occurring bovine encapsidation sequences, which may be of the same or different serotypes. In some examples, a bovine adenovirus sequence(s) essential for encapsidation is heterologous to the adenovirus vector, i.e., is a non-bovine adenovirus vector or is of a different bovine adenovirus serotype. In some examples, the non-bovine adenovirus vector sequences are mammalian including but not limited to human, porcine, ovine, canine, feline or equine adenovirus sequences. In some examples, an isolated bovine adenovirus sequence(s) essential for encapsidation may be used in an adenovirus vector that comprises human adenovirus capsid protein encoding sequences or an isolated bovine adenovirus sequence(s) essential for encapsidation may be used in a bovine adenovirus vector that is modified to exhibit tropism for human cells. In another example, an isolated bovine adenovirus sequence(s) essential for encapsidation may be used in an adenovirus vector that comprises porcine adenovirus sequences, such as, for example, porcine capsid protein encoding sequences or other porcine sequence, including porcine adenoviral sequences essential for replication or encapsidation. In some examples, an isolated bovine adenoviral sequence(s) essential for encapsidation is used in an adenovirus vector that comprises bovine adenovirus sequences, wherein the bovine adenovirus sequence may be the same or different serotype than the isolated bovine adenovirus sequence essential for encapsidation. The heterologous adenovirus vector sequences are not limited and can be any mammalian adenovirus sequence as long as the bovine adenovirus sequence(s) essential for encapsidation can function to insert the adenovirus DNA into an adenovirus capsid. An adenovirus vector may be constructed to comprise multiple isolated bovine adenovirus sequences essential for encapsidation, for example, multiple identical BAV encapsidation sequences or multiple different BAV encapsidation sequences, or the bovine adenovirus vector sequence may be heterologous, i.e. of a different serotype, to the isolated bovine adenovirus sequence essential for encapsidation. In some examples, the BAV encapsidation sequence is the BAV-3 encapsidation sequence located between about nt 224 and about nt 540, as disclosed herein in FIGS. 1A-1B. In other examples, an adenovirus vector of the invention further comprises a transgene or heterologous nucleic acid.

In other examples of the present invention, a mammalian adenovirus vector comprises one or more isolated bovine adenoviral sequences essential for encapsidation, wherein the mammalian adenovirus vector may be a bovine adenovirus vector or a non-bovine adenovirus vector, and the adenovirus vector lacks at least one adenoviral nucleic acid sequence encoding a viral protein function necessary for replication or has a mutation in at least one adenoviral nucleic acid sequence encoding a viral protein function necessary for replication. An adenovirus vector may have a deletion or part or all of an early gene, such as for example E1, such as E1A, E2, E3 or E4 or may have a deletion or part or all of late gene such as L1-L5. An adenovirus vector may have a deletion of multiple adenoviral sequences, including sequences essential for replication as long as sequences essential for replication and encapsidation are present on the adenovirus vector or provided by helper cells. An adenovirus vector comprising one or more isolated bovine adenovirus sequence essential for encapsidation may be replication-defective or replication competent.

The present invention also provides vectors, compositions including vaccine compositions, and host cells comprising isolated BAV sequences essential for encapsidation.

BAV E1 Transcriptional Control Regions

The present invention identifies BAV E1 transcriptional control regions. Accordingly, the present invention provides isolated BAV E1 transcriptional control regions as well as adenovirus and adenovirus vectors, including BAV and BAV vectors, comprising modifications in a part of or all of one or more E1 transcriptional control region(s). In some examples, the modification is a deletion of a part of or all of one or more E1 transcriptional control region(s) and in other examples a modification is an addition of a part of or all of one or more of the same or different E1 transcriptional control region(s).

As demonstrated herein, Northern blot analysis of a series of bovine adenovirus mutants containing deletions in the BAV-3 E1A 5'-flanking sequences between the left ITR and the start ATG codon of E1A defines two functionally separate transcriptional control regions for viral early genes, transcriptional control region I and transcriptional control region 2. Transcriptional control region I is located between BAV-3 nucleotides about 224 and about 382 with respect to the left terminus. Transcriptional control region II is located between BAV-3 nucleotides about 537 and about 560 relative to the left terminus of the BAV-3 genome. As described herein, deletion of the transcriptional control region I reduced the steady-state level of E1A mRNAs in bovine adenovirus infected cells. The deletion of region I also resulted in the reduced rate of transcription of other early genes including E1B, E2A, E3 and E4. Deletion of region II had no effects on the transcription of E1A, but caused increased levels of E1B, E2A, E3 and E4 mRNAs in bovine adenovirus infected cells. Deletion of this region dramatically decreased the transcription of all tested early genes including E1A, E1B, E2A, E3, and E4. However, the deletion of half this region (as in the constructs Bav12 and Bav34 as described in the Examples and Figures), did not lead to reduction in E1A transcription. The slight reduction in E1A gene transcription in Bav36 (as described in the Examples and Figures), which contains deletion of sequences between nucleotide about 311 and about 468, overlapping with the deleted sequences (between nucleotide about 311 and about 382, as in the construct Bav34, described in the Examples and Figures), demonstrated that sequences between nucleotide about 382 and about 468 are also necessary for E1A gene transcription.

On the basis of experimental results, to further define the structure of E1A transcriptional control region, the left end genomic sequences of BAV-3 was analyzed with two software programs. The program I (Neural network promoter prediction, fruitfly.org/seq tools/promoter (Reese, et al. (1995, The Seventh International Sequencing and Analysis Conference, Hilton Head Island, South Carolina); Reese, et al. (1996, Biocomputing: Proceedings of the 1996 Pacific Symposium, edited by Lawrence Hunter and Tern E. Klein, World Scientific Publishing Co., Singapore, 1996, Jan. 2-7)) was used to search for potential eukaryotic promoter. The program II (Hctata: Hamming-Clustering method for TATA signal prediction in eukaryotic genes. In: Tools for prediction and analysis of protein-coding gene structure. 125.itba.mi.cnr.it/~webgene/wwwHC tata (Milanesi et al. (1995, Proceedings of the Third International Symposium on Bioinformatics, World Scientific Publishing, Singapore, 461-466); Milanesi et al. (1996, Comput. Applic. Biosci. Vol. 12:399-404); Milanesi et al. (1998, Guide to Human Genome Computing (2nd Edition, ed. M.J. Bishop) Academic Press, Cambridge, 215-256); Milanesi et al. (1999, Bioformatics Vol. 15:612-621) was used to predict the potential TATA box, the core component of TATA box-containing eukaryotic promoter (Hampsey et al. (1998, Microbiol. Mci. Biol. Rev. Vol. 62:465-503)). The results are diagrammed in the Figures. Results from program 1 suggests the E1A gene is under the control of a TATA-less promoter that is probably located in the ITR between about nt 94 and about nt 211. The region between about nt 94 and about nt 211 contains GC-rich sequences, which may be SP1 binding sites (Hatfield et al. (1993, J. Virol. Vol. 67:3931-3939); Kadonaga et al. (1987, Cell. Vol. 51:1079-1090)). It has been reported that the deletion of 72 bp sequences between about nt 89 and about nt 162, overlapping most sequences of potential promoter predicted by program I, did not seem to have any effect on the kinetics of viral replication compared to wild-type BAV-3 (van Olphen, (2002a, Intervirology Vol. 45:188-192)). Without being bound by theory, the results indirectly suggest that GC-rich sequences between about nt 94 and about nt 211 could not be the major promoter region of E1A. The program II also suggests that the E1A gene promoter is located in an ITR, but it could contain a TATA box with the sequences 'TATGA' between about nt 68 and about nt 72. Additionally, the CAAT element of eukaryotic protein-coding gene promoter was found between about nt 46 and about nt 49, upstream of potential TATA box (Reddy et al. (1998, J Virol. Vol. 72:1394-1402); Reddy et al. (1999, Virology Vol. 253:299-308)). Based on the experimental results and promoter prediction, Region I, that is BAV-3 nucleotides between about 224 and about 382, is identified as the regulatory control region, rather than the core promoter region.

The deletion of Region I reduced the transcription of all tested early genes including E1B, E2A, E3, and E4. In HAV, E1A transcriptional control region contains an enhancer element II which enhances in cis all of the early gene transcription on the viral genome (Hearing et al. (1983, Cell. Vol. 33:695); (1986, Cell. Vol. 45:229-236)). In addition, the E1 gene products are required for activation of other early gene promoters (Berk et al. (1979, Cell. Vol. 17:935-944); Jones et al. (1979, Proc. Natl. Acad. Sci. USA Vol. 76:3665-3669); Grand et al. (1987, Biochem. Vol. 241:25-38)). However, in the case of BAV-3, the decreased transcription of E1B, E2A, E3, and E4 may be due to the cis-acting effects of Region I deletion, or may be due to the trans-acting effects of decreased E1A transcription.

The second transcriptional control region (Region II) defined herein is located between about nt 537 and about nt 560 relative to the left terminus of BAV-3 genome. Deletion of Region II as in the construct (Bav912, described in the Examples and Figures) has no effects on the accumulation of E1A mRNAs early after infection (7 h), but directly increased the E1B mRNA level. In addition, the enhancement of transcription of E2A, E3, and E4 was evident with mutant Bav912. The enhanced transcription of E2A, E3, and E4 may be a cis-acting or trans-acting effect.

In the left 11% of the HAV genome, there are three transcription units, E1A, E1B, and pIX. Each unit has its own promoter and poly (A) signal and poly(A) site (Babiss et al. (1991, J. Virol. Vol. 65:598-605); Bos et al. (1983, EMBO J. Vol. 2:73-76); and Maat et al. (1980, Gene Vol. 10:27-38)). In BAV-3, the transcripts of E1A, E1B, and pIX are 3'-coterminal (Reddy et al. (1998, J Virol. Vol. 72:1394-1402); Reddy et al. (1999, Virology Vol. 253:299-308); and Zheng et al. (1999, J. Gen. Virol. Vol. 80:1735-1742)). The transcriptional unit of pIX is transcribed from an independent promoter and encodes a structural component of the adenoviral capsid (Reddy et al. (1999b, Virology Vol. 253: 299-308)). Without being bound by theory, the result that the deletion of Region I in Bav14 (as described in the Examples and Figures) reduced simultaneously the steady-state levels of E1A and E1B raises a possibility that E1A and E1B maybe share some common sequences as the transcriptional control elements.

Accordingly, as described herein, the present invention provides vectors, such as, adenovirus vectors and adenovirus comprising a modification, that is a deletion and/or addition of part or all of one or more E1 transcriptional control regions described herein. The present invention encompasses BAV vectors and BAV having a modification in one or more E1 transcriptional control regions. In some examples where it is desirable to produce a BAV capable of growing for a period of time (such as for vaccine purposes or gene delivery purposes), a BAV E1 transcriptional control region corresponding to the BAV3 region from about nucleotide 224 to about 382, or a part thereof, is deleted and/or a BAV E1 transcriptional control region corresponding to the BAV3 region from about nucleotide about 537 to about 560, or a part thereof, is added. In some examples, for production of a lytic BAV (such as for use in methods for treating or ameliorating the symptoms of cancer, such as in reducing tumor growth or targeted killing of cancer cells) increasing expression of E1A (and/or decreasing expression of E1B which has anti-apoptotic activity) is desirable. For production of a lytic BAV, one or more BAV E1 transcription control region(s) corresponding to the BAV3 region from nucleotide about 537 to about 560, or a part thereof, is deleted and/or a BAV E1 transcriptional control region corresponding to the BAV3 region from about nucleotide 224 to about 382, or a part thereof, is added. Such deletions and/or additions of BAV E1 transcriptional control regions should not inhibit encapsidation of the BAV.

The present invention also provides identification of BAV-3 E1A promoter. Although ITR of HAdV-5 displays promoter activity (Hartfield and Hearing, 1991, Virology 184, 265; Yamamoto 2003, J. Virol. 77, 1633), HAd-5 E1A uses its own promoter (located between the left ITR and the ATG codon of E1A) to transcribe E1A (Hearing and Shenk, 1983, Cell, 33:695; 1986, cell, 45, 229-236). The TATA box of HAdV-5 E1A promoter and two enhancer elements are located between nt 472 and 475 and between nt 195 and 358 respectively, relative to the left end of HAdV-5 genome (Hatfield and Hearing, 1991, supra). However, unlike HAdV-5 the conserved motifs of eukaryotic gene promoter such as TATA box and CAAT box sequences between left ITR and the ATG of E1A of BAdV-3 could not be found suggesting that the left ITR of BAdV-3 may contain E1A promoter elements. Several lines of evidence support this prediction. First, DNA sequence analysis of the left ITR showed the presence of a CCAAT box (nt 45-49), TATA-like box (nt 68-72), and most of GC boxes (nt 108-209) based on FIG. 1A-1B. Second, in the absence of sequences between nt 224 and 560 (Bav12), the promoter activity of ITR is sufficient to express E1A which supports the Bav112 growth in MDBK cells. Third, transcriptional analysis of E1 region identified E1A transcriptional start sites near left ITR (Reddy et al., 1998, J. Virol. 72, 1394-1402 and 1999, Virology, 253, 299-308). Based on these observations, it is predicted that left ITR of BAdV-3 contains core elements of the E1A promoter. The present invention encompasses the use of replication-competent bovine adenovirus. The present invention encompasses replication competent bovine adenovirus comprising the E1A promoter. In some examples, the replication-competent adenovirus comprises a deletion of non-essential gene regions (that is, regions of the genome that are non-essential for replication, such as part or all of E3 region) and comprises (retains) the essential E1 gene region along with the E1A promoter as described herein.

The present invention encompasses adenoviral vectors comprising transgenes. Among transgenes of interest which are useful in the context of the present invention, there may be mentioned genes coding for cytokines such as interferons and interleukins; genes encoding lymphokines; genes coding for membrane receptors such as the receptors recognized by pathogenic organisms (viruses, bacteria or parasites), including the HIV virus (human immunodeficiency virus); genes coding for coagulation factors such as factor VIII and factor IX; genes coding for dystrophins; genes coding for insulin; genes coding for proteins participating directly or indirectly in cellular ion channels, such as the CFTR (cystic fibrosis transmembrane conductance regulator) protein; genes coding for antisense RNAs, or proteins capable of inhibiting the activity of a protein produced by a pathogenic gene which is present in the genome of a pathogenic organism, or proteins (or genes encoding them) capable of inhibiting the activity of a cellular gene whose expression is deregulated, for example an oncogene; genes coding for a protein inhibiting an enzyme activity, such as $\alpha_1$-antitrypsin or a viral protease inhibitor, for example; genes coding for variants of pathogenic proteins which have been mutated so as to impair their biological function, such as, for example, trans-dominant variants of the tat protein of the HIV virus which are capable of competing with the natural protein for binding to the target sequence, thereby preventing the activation of HIV; genes coding for antigenic epitopes in order to increase the host cell's immunity; genes coding for major histocompatibility complex classes I and II proteins, as well as the genes coding for the proteins which are inducers of these genes; genes coding for antibodies; genes coding for immunotoxins; genes encoding toxins; genes encoding growth factors or growth hormones; genes encoding cell receptors and their ligands; genes encoding tumor suppressors; genes coding for cellular enzymes or those produced by pathogenic organisms; and suicide genes. The HSV-1 thymidine kinase (TK) suicide gene is mentioned as an example. This viral TK enzyme displays markedly greater affinity compared to the cellular TK enzyme for certain nucleoside analogues (such as acyclovir or gancyclovir). TK enzyme converts the analogues to monophosphorylated molecules, which can themselves be converted by cellular enzymes to nucleotide precursors, which are toxic. These nucleotide analogues can be incorporated into replicating DNA molecules, hence incorporation occurs chiefly in the DNA of dividing cells. This incorporation can result in specific destruction of dividing cells such as cancer cells.

This list is not restrictive, and any other transgene of interest can be used in the context of the present invention. In some cases the gene for a particular antigen can contain a large number of introns or can be from an RNA virus, in these cases a complementary DNA copy (cDNA) can be used. It is also possible that only fragments of nucleotide sequences encoding proteins can be used (where these are sufficient to generate a protective immune response or a specific biological effect) rather than the complete sequence as found in the wild-type organism. Where available, synthetic genes or fragments thereof can also be used. However, the present invention can be used with a wide variety of genes, fragments and the like, and is not limited to those set out above. Adenovirus vectors can be used to express antigens for provision of, for example, subunit vaccines. Antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). Antigenic polypeptides to be expressed by the virus systems of the present invention may contain full-length (or near full-length) sequences encoding antigens or, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. The peptide can encode a "protective epitope" that is capable of raising in the host a "protective immune response;" i.e., a humoral (i.e. antibody-mediated), cell-mediated, and/or mucosal immune response that protects an immunized host from infection.

A gene of interest can be placed under the control of regulatory sequences suitable for its expression in a host cell. Suitable regulatory sequences are understood to mean the set of elements needed for transcription of a gene into RNA (ribozyme, antisense RNA or mRNA), for processing of RNA, and for the translation of an mRNA into protein. Among the elements needed for transcription, the promoter assumes special importance. It can be a constitutive promoter or a regulatable promoter, and can be isolated from any gene of eukaryotic, prokaryotic or viral origin, and even adenoviral origin. Alternatively, it can be the natural promoter of the gene of interest. Generally speaking, a promoter used in the present invention can be chosen to contain cell-specific regulatory sequences, or modified to contain such sequences. For example, a gene of interest for use in the present invention is placed under the control of an immunoglobulin gene promoter when it is desired to target its expression to lymphocytic host cells. There may also be mentioned the HSV-1 TK (herpesvirus type 1 thymidine kinase) gene promoter, the adenoviral MLP (major late promoter), in particular of human adenovirus type 2, the RSV (Rous Sarcoma Virus) LTR (long terminal repeat), the CMV (Cytomegalovirus) early promoter, and the PGK (phosphoglycerate kinase) gene promoter, for example, permitting expression in a large number of cell types.

Alternatively, targeting of a recombinant BAV vector to a particular cell type can be achieved by constructing recombinant hexon and/or fiber genes. The protein products of these genes are involved in host cell recognition; therefore, the genes can be modified to contain peptide sequences that will allow the virus to recognize alternative host cells. U.S. patent Publication Ser. No. 2002-0034519-A1 discloses bovine adenovirus having altered tropism.

For propagation of an adenovirus vector that lacks sequences encoding viral protein function necessary for replication, helper cell lines can be used to provide the missing or defective adenoviral function. For example, 293 cells provide E1 function, therefore, a human adenovirus having a deletion in E1 function can be propagated. in 293 cells. Other helper cells are disclosed in U.S. Pat. No. 6,458,586.

Parks et al., supra, describes a use of the Cre/lox system in adenovirus systems. In the present invention, a helper virus can be produced with loxP sites flanking portions of the helper virus genome that are to be deleted, such as a packaging domain of a helper adenovirus or other sequences, and a helper cell line is produced that expresses Cre recombinase. The Cre recombinase recognizes the loxP sites and deletes the portion of the helper virus flanked by the loxP sites.

The sequences for the bovine adenovirus regions essential for encapsidation and E1 transcriptional control regions may be isolated from a viral genome by conventional means (digestion with a restriction enzyme, PCR and the like) or may be produced by chemical synthesis. Optionally, in the context of the present invention, they may comprise mutations (deletion, substitution and/or addition of one or more nucleotides) compared with the native sequences as long as the mutation maintains function, that is, for example, the ability to encapsidate the virus, or function as a E1 transcriptional control region. To determine if a mutation in a bovine adenovirus region essential for encapsidation maintains the ability to encapsidate virus, one of skill in the art would insert the sequence into an appropriate vector and determine the encapsidation properties in an appropriate cell line, for example, by determining the viral titer of the expression of a reporter gene. It is also possible to include other exogenous sequences (restriction sites and the like) along with the region essential for encapsidation. They may be inserted into the adenoviral vector according to the invention in addition to other sequences or as a replacement thereof. The insertion of bovine adenovirus regions essential for encapsidation into an adenovirus vector may take place in 5' or in 3' to adenovirus sequence, in a region of the adenovirus where an encapsidation site would be located or at a different site, as long as the adenovirus maintains the ability to encapsidate virus.

The present invention also encompasses kits containing the adenovirus vector(s) of this invention. These kits can be used for example for producing proteins for screening, assays and biological uses, such as for production of antigens for mammalian vaccine purposes. Procedures using these kits can be performed by clinical laboratories, experimental laboratories, medical practitioners, or private individuals.

The kits of the invention comprise an adenovirus vector described herein in suitable packaging. The kit may optionally provide additional components that are useful in the procedure, including, but not limited to, buffers, developing reagents, labels, reacting surfaces, means for detection, control samples, instructions, and interpretive information. The kit may include instructions for use of an adenovirus vector.

Construction of Recombinant Adenovirus Vectors

In some examples disclosed herein, a recombinant adenovirus vector comprising an isolated bovine adenovirus sequence essential for encapsidation and/or a bovine E1 transcriptional control region is produced by recombinant DNA techniques. The present invention provides vectors such as adenovirus vectors comprising polynucleotides for bovine adenovirus sequence essential for encapsidation and/or a bovine E1 transcriptional control region and/or a transgene. Molecular cloning and viral construction are generally known in the art. In some examples, an adenovirus vector comprising nucleic acid for a bovine adenovirus sequence essential for encapsidation and/or a bovine E1 transcriptional control region and/or a transgene is produced by ligation in vitro to an adenovirus vector (linearized) and subsequently introduced into a host cell by means known in the art.

In one embodiment of the invention, a recombinant adenovirus vector comprising an isolated bovine adenovirus sequence essential for encapsidation and/or a bovine E1 transcriptional control region and/or a transgene is constructed by in vivo recombination between a plasmid and an adenoviral genome. Generally, transgenes are inserted into a plasmid vector containing a portion of the desired adenovirus genome, and in some examples, the adenovirus genome is heterologous to bovine adenovirus, wherein the adenovirus genome may possess a mutation of, for example, a deletion of one or more adenoviral sequences encoding viral proteins. In some examples, adenovirus sequences encoding protein function essential for viral replication, such as the E1 region, are mutated, such as for example, deleted in part or all of the sequence. The transgene is inserted into the adenovirus insert portion of the plasmid vector, such that the transgene is flanked by adenovirus sequences that are adjacent on the adenovirus genome. The adenovirus sequences serve as "guide sequences," to direct insertion of the transgene to a particular site in the adenovirus genome; the insertion site being defined by the genomic location of the guide sequences. Bovine adenovirus packaging sequences can be added into an adenovirus vector by means known to those of skill in the art.

The vector is generally a bacterial plasmid, allowing multiple copies of the cloned sequence to be produced. In one embodiment, the plasmid is co-transfected, into an appropriate host cell, with an adenovirus genome, or portion thereof. The adenovirus genome can be isolated from virions, or can comprise a genome that has been inserted into a plasmid, using standard techniques of molecular biology and biotechnology. In some examples, adenovirus vector sequences can be deleted in regions such as, for example, E1, E3, E4 and/or the region between E4 and the right end of the genome and/or late regions such as L1-L5. Adenovirus genomes can be deleted in essential regions, such as E1, if the essential function are supplied by a helper cell line. In some examples, the adenovirus vector is deleted in multiple nucleic acid sequences encoding viral proteins as long as any sequences essential for replication are provided by a helper virus.

Insertion of the cloned transgene into a viral genome occurs by in vivo recombination between a plasmid vector (containing transgene sequences flanked by adenovirus guide sequences) and an adenovirus genome following co-transfection into a suitable host cell. The adenovirus genome contains inverted terminal repeat (ITR) sequences required for initiation of viral DNA replication (Reddy et al. (1995), *Virology* 212:237-239). Incorporation of the cloned transgene into the adenovirus genome thus places the transgene sequences into a DNA molecule containing adenoviral sequences.

Incorporation of the cloned transgene into an adenovirus genome places these sequences into a DNA molecule that can be replicated and packaged in an appropriate helper cell line. Multiple copies of a single transgene sequence can be inserted to improve yield of the gene product, or multiple transgene sequences can be inserted so that the recombinant virus is capable of expressing more than one heterologous gene product. The transgene sequences can contain additions, deletions and/or substitutions to enhance the expression and/or immunological effect of the expressed gene product(s).

Attachment of guide sequences to a heterologous sequence can also be accomplished by ligation in vitro. In this case, a nucleic acid comprising a transgene sequence flanked by an adenovirus guide sequences can be co-introduced into a host cell along with the adenovirus genome, and recombination can occur to generate a recombinant adenovirus vector. Introduction of nucleic acids into cells can be achieved by any method known in the art, including, but not limited to, microinjection, transfection, electroporation, $CaPO_4$ precipitation, DEAE-dextran, liposomes, particle bombardment, etc.

In one embodiment of the invention, a recombinant adenovirus expression cassette can be obtained by cleaving a wild-type adenovirus genome with an appropriate restriction enzyme to produce an adenovirus restriction fragment representing a portion of the genome. The restriction fragment can be inserted into a cloning vehicle, such as a plasmid, and thereafter at least one transgene sequence (which may or may not encode a foreign protein) can be inserted into the adenovirus region with or without an operatively-linked eukaryotic transcriptional regulatory sequence. The recombinant expression cassette is contacted with the adenovirus genome and, through homologous recombination or other conventional genetic engineering methods, the desired recombinant is obtained. These DNA constructs can then undergo recombination in vitro or in vivo, with an adenovirus genome either before or after transformation or transfection of an appropriate host cell.

Deletion of adenovirus sequences, to provide a site for insertion of heterologous sequences or to provide additional capacity for insertion at a different site, or addition of sequences, such as an adenovirus E1 transcriptional control region or BAV packaging domains, can be accomplished by methods well-known to those of skill in the art. For example, for adenovirus sequences cloned in a plasmid, digestion with one or more restriction enzymes (with at least one recognition sequence in the adenovirus insert) followed by ligation will, in some cases, result in deletion of sequences between the restriction enzyme recognition sites. Alternatively, digestion at a single restriction enzyme recognition site within the adenovirus insert, followed by exonuclease treatment, followed by ligation will result in deletion of adenovirus sequences adjacent to the restriction site. A plasmid containing one or more portions of the adenovirus genome with one or more deletions, constructed as described above, can be co-transfected into a bacterial cell along with a plasmid containing a full-length adenovirus genome to generate, by homologous recombination, a plasmid containing a adenovirus genome with a deletion at a specific site. Adenovirus virions containing the deletion (or addition) can then be obtained by transfection of appropriate mammalian cells, such as for example, mammalian cells comprising complementing adenovirus nucleotide sequences deleted from the adenovirus vector, with the plasmid containing an adenovirus genome with a deletion at a specific site. Accordingly, the present invention provides a method of preparing an adenovirus comprising the steps of, introducing into a cell a) a recombinant adenovirus vector which comprises one or more isolated bovine adenovirus sequence(s) essential for encapsidation and/or a modification in an E1 transcriptional control region, wherein said adenovirus vector is optionally deleted in part or all of one or more adenoviral proteins necessary for replication and b) any necessary helper virus that comprise nucleic acid encoding one or more adenovirus proteins necessary for replication of said adenovirus; and culturing the cell under conditions suitable for production of adenovirus; and optionally recovering said adenovirus.

Expression of an inserted sequence in a recombinant adenovirus vector will depend on the insertion site. Accordingly, insertion sites may be adjacent to and downstream (in the transcriptional sense) of adenovirus promoters. Locations of restriction enzyme recognition sequences downstream of adenovirus promoters, for use as insertion sites, can be easily determined by one of skill in the art from the adenovirus nucleotide sequences known in the art Alternatively, various in vitro techniques can be used for insertion of a restriction enzyme recognition sequence at a particular site, or for insertion of heterologous sequences at a site that does not contain a restriction enzyme recognition sequence. Such methods include, but are not limited to, oligonucleotide-mediated heteroduplex formation for insertion of one or more restriction enzyme recognition sequences (see, for example, Zoller et al. (1982) *Nucleic Acids Res.* 10:6487-6500; Brennan et al. (1990) *Roux's Arch. Dev. Biol.* 199: 89-96; and Kunkel et al. (1987) *Meth. Enzymology* 154:367-382) and PCR-mediated methods for insertion of longer sequences. See, for example, Zheng et al. (1994) *Virus Research* 31:163-186.

It is also possible to obtain expression of a transgene or heterologous nucleic acid sequence inserted at a site that is not downstream from an adenovirus promoter, if the heterologous sequence additionally comprises transcriptional regulatory sequences that are active in eukaryotic cells. Such transcriptional regulatory sequences can include cellular promoters such as, for example, the bovine hsp70 promoter and viral promoters such as, for example, herpesvirus, adenovirus and papovavirus promoters and DNA copies of retroviral long terminal repeat (LTR) sequences.

In another embodiment, homologous recombination in a procaryotic cell can be used to generate a cloned adenovirus genome; and the cloned adenovirus genome can be propagated as a plasmid. Infectious virus can be obtained by transfection of mammalian cells with the cloned adenovirus genome rescued from plasmid-containing cells.

Suitable host cells include any cell that will support recombination between an adenovirus genome and a plasmid containing adenovirus sequences, or between two or more plasmids, each containing adenovirus sequences. Recombination is generally performed in procaryotic cells, such as *E. coli*, while transfection of a plasmid containing a viral genome, to generate virus particles, is conducted in eukaryotic cells, preferably mammalian cells, most preferably bovine cell cultures. The growth of bacterial cell cultures, as well as culture and maintenance of eukaryotic cells and mammalian cell lines are procedures which are well-known to those of skill in the art. Accordingly, the present invention provides host cells comprising adenovirus vectors of the present invention.

In one example of the invention, a replication-defective recombinant adenovirus vector comprising one or more bovine adenovirus sequence(s) essential for encapsidation and/or modification in an E1 transcriptional control region is used for expression of a transgene, such as for example, an antigen of a pathogen. In some examples, the replication-defective adenovirus vector lacks nucleic acid encoding E1 region function (that is, E1 functional protein) and a helper virus provides E1 function, that is, expresses E1 functional protein). In other examples, the adenovirus vector lacks nucleic acid encoding multiple adenoviral genes. Transgene sequences can be inserted so as to replace deleted adenovirus region(s), and/or can be inserted at other sites in the genome. Replication-defective vectors with deletions in essential regions (regions essential for replication), are grown in helper cell lines, which provide the function of the deleted essential region.

Accordingly, the present invention provides recombinant helper cell lines, produced according to the present invention by constructing an expression cassette comprising an adenoviral region(s) necessary for complementation of adenovirus regions deleted in the adenovirus vector and transforming host cells therewith to provide complementing cell lines or cultures providing deleted functions. In some examples, the adenovirus vector lacks E1 regions essential for replication and the host cell is transformed with the adenovirus E1 region. The terms "complementing cell," "complementing cell line," "helper cell" and "helper cell line" are used interchangeably herein to denote a cell line that provides a viral function that is deficient in a deleted adenovirus vector. These recombinant complementing cell lines are capable of allowing a defective recombinant adenovirus to replicate and express one or more transgenes or fragments thereof. U.S. Pat. No. 6,458,586 discloses a bovine helper cell line comprising nucleic acid encoding human E1 function. In other examples, a BAV packaging domain is provided by a helper cell.

More generally, replication-defective recombinant adenovirus vectors, lacking one or more essential functions encoded by the adenovirus genome, can be propagated in appropriate complementing cell lines, wherein a particular complementing cell line provides a function or functions that is (are) lacking in a particular defective recombinant adenovirus vector. Complementing cell lines can provide viral functions through, for example, co-infection with a helper virus, or by integrating or otherwise maintaining in stable form a fragment of a viral genome encoding a particular viral function. In another embodiment of the invention, adenovirus function can be supplied (to provide a complementing cell line) by co-infection of cells with a virus which expresses the function that the vector lacks.

Uses of Adenovirus Vectors of the Present Invention

The use of adenoviral vectors in therapeutic and prophylactic methods is well documented. There are limitations to the use of adenovirus vectors, including for example limited insertion capacity of adenovirus vectors. Also, one problem that has arisen in the use of adenovirus vectors intended for immunization and gene delivery in mammals, such as humans, is the development of an immunological response (or in some cases, a pre-existing immunity) to the adenovirus, including to human adenovirus (HAVs). The expression of viral gene products from adenovirus vectors may contribute to the induction of a host immune response against transduced cells. Also, the presence of low levels of helper-independent vectors in the batches of helper-dependent human adenoviruses that are grown in complementing human cell lines has been reported. Fallaux et al. (1998) *Human Gene Therapy* 9:1909. This occurs as a result of recombination events between the viral DNA and the integrated adenoviral sequences present in the complementing cell line. Hehir et al. (1996) J. Virol. 70:8459-8467. This type of contamination constitutes a safety risk, which could result in the replication and spread of the virus.

The present invention provides adenovirus vector constructs that provide for increased insertion capacity. The present invention encompasses adenovirus vectors comprising one or more bovine adenovirus sequence(s) essential for encapsidation and deleted in one or more or multiple adenovirus nucleic acid sequences encoding viral proteins, thereby allowing for increased insertion capacity. The present invention encompasses adenovirus vectors comprising a modification in an E1 transcriptional control region and deleted in one or more or multiple adenovirus nucleic acid sequences encoding viral proteins, thereby allowing for increased insertion capacity. In some examples of the present invention, adenovirus vectors comprising bovine adenovirus sequences necessary for encapsidation can be used in therapeutic or prophylatic methods to decrease or minimize host immune response. For example, the present invention encompasses adenovirus vectors comprising one or more bovine adenovirus sequence(s) essential for encapsidation and non-bovine mammalian adenovirus sequences, such as for example, human adenovirus sequences, such as for example human capsid protein encoding sequences for use in treating or immunizing non-bovine mammals, such as for example, humans. In some examples, the adenovirus vector lacks nucleic acid encoding one or more or multiple non-bovine mammalian viral proteins thereby providing an opportunity to minimize host immune response to adenovirus proteins. The present invention provides adenovirus vectors and methods for elimination of helper-independent adenoviruses in the batches of helper-dependent vectors by providing for the use of bovine adenovirus packaging domains in non-bovine mammalian adenovirus vectors, such as human adenovirus vectors.

The present invention encompasses BAV having a modification in one or more E1 transcriptional control regions. In some examples where it is desirable to produce a BAV capable of growing for a period of time (such as for vaccine purposes or gene delivery purposes), a BAV E1 transcriptional control region corresponding to the BAV3 region from about nucleotide 224 to about 382, or a part thereof, is deleted and/or a BAV E1 transcriptional control region corresponding to the BAV3 region from about nucleotide about 537 to about 560, or a part thereof, is added. In some examples, for production of a lytic BAV (such as for use in methods for treating or ameliorating the symptoms of cancer, such as in reducing tumor growth or targeted killing of cancer cells) increasing expression of E1A (and/or decreasing expression of E1B which has anti-apoptotic activity) is desirable. For production of a lytic BAV, one or more BAV E1 transcription control region(s) corresponding to the BAV3 region from nucleotide about 537 to about 560, or a part thereof, is deleted and/or a BAV E1 transcriptional control region corresponding to the BAV3 region from about nucleotide 224 to about 382, or a part thereof, is added. Such deletions and/or additions of BAV E1 transcriptional control regions should not inhibit encapsidation of the BAV.

Also, the adenovirus vectors of the invention can be used for regulated expression of foreign polypeptides encoded by transgenes. Standard conditions of cell culture, such as are known by those of skill in the art, will allow for expression of recombinant polypeptides. They can be used, in addition, for regulated expression of RNAs encoded by heterologous nucleotide sequences, as in for example, antisense applications and expression of ribozymes. The adenovirus vectors of the present invention can be used for the expression of polypeptides in applications such as in vitro polypeptide production, vaccine production, nucleic acid immunization and gene delivery, for example. Polypeptides of therapeutic and/or diagnostic value include, but are not limited to, coagulation factors, growth hormones, cytokines, lymphokines, tumor-suppressing polypeptides, cell receptors, ligands for cell receptors, protease inhibitors, antibodies, toxins, immunotoxins, dystrophins, cystic fibrosis transmembrane conductance regulator (CFTR) and immunogenic polypeptides.

In some examples of the present invention adenovirus vectors will comprise heterologous sequences encoding protective determinants of various pathogens of mammals, including for example humans, cattle, swine, sheep, or other mammals, for use in subunit vaccines and nucleic acid immunization. Representative human pathogen antigens include but are not limited to HIV virus antigens and hepatitis virus antigens. Representative swine pathogen antigens include, but are not limited to, pseudorabies virus (PRV) gp50; transmissible gastroenteritis virus (TGEV) S gene; genes of porcine respiratory and reproductive syndrome virus (PRRS), in particular ORFs 3, 4 and 5; genes of porcine epidemic diarrhea virus; genes of hog cholera virus; genes of porcine parvovirus; and genes of porcine influenza virus. Representative bovine pathogen antigens include bovine herpes virus type 1; bovine diarrhea virus; and bovine coronavirus.

Various foreign genes or nucleotide sequences or coding sequences (prokaryotic, and eukaryotic) can be inserted into an adenovirus vector, in accordance with the present invention, particularly to provide protection against a wide range of diseases.

A heterologous (i.e., foreign) nucleotide sequence or transgene can consist of one or more gene(s) of interest, and may have therapeutic or diagnostic value. In the context of the present invention, a gene of interest can code either for an antisense RNA, a ribozyme or for an mRNA which will then be translated into a protein of interest. A gene of interest can be of genomic type, of complementary DNA (cDNA) type or of mixed type (minigene, in which at least one intron is deleted). It can code for a mature protein, a precursor of a mature protein, in particular a precursor intended to be secreted and accordingly comprising a signal peptide, a chimeric protein originating from the fusion of sequences of diverse origins, or a mutant of a natural protein displaying improved or modified biological properties. Such a mutant can be obtained by deletion, substitution and/or addition of one or more nucleotide(s) of the gene coding for the natural protein, or any other type of change in the sequence encoding the natural protein, such as, for example, transposition or inversion.

Among genes of interest which are useful in the context of the present invention include but are not limited to genes coding for cytokines such as interferons and interleukins; genes encoding lymphokines; genes coding for membrane receptors such as the receptors recognized by pathogenic organisms (viruses, bacteria or parasites), including the HIV virus (human immunodeficiency virus); genes coding for coagulation factors such as factor VIII and factor IX; genes coding for dystrophins; genes coding for insulin; genes coding for proteins participating directly or indirectly in cellular ion channels, such as the CFTR (cystic fibrosis transmembrane conductance regulator) protein; genes coding for antisense RNAs, or proteins capable of inhibiting the activity of a protein produced by a pathogenic gene which is present in the genome of a pathogenic organism, or proteins (or genes encoding them) capable of inhibiting the activity of a cellular gene whose expression is deregulated, for example an oncogene; genes coding for a protein inhibiting an enzyme activity, such as $\alpha_1$-antitrypsin or a viral protease inhibitor, for example; genes coding for variants of pathogenic proteins which have been mutated so as to impair their biological function, such as, for example, trans-dominant variants of the tat protein of the HIV virus which are capable of competing with the natural protein for binding to the target sequence, thereby preventing the activation of HIV; genes coding for antigenic epitopes in order to increase the host cell's immunity; genes coding for major histocompatibility complex classes I and II proteins, as well as the genes coding for the proteins which are inducers of these genes; genes coding for antibodies; genes coding for immunotoxins; genes encoding toxins; genes encoding growth factors or growth hormones; genes encoding cell receptors and their ligands; genes encoding tumor suppressors; genes coding for cellular enzymes or those produced by pathogenic organisms; and suicide genes. The HSV-1 TK suicide gene is mentioned as an example. This viral TK enzyme displays markedly greater affinity compared to the cellular TK enzyme for certain nucleoside analogues (such as acyclovir or gancyclovir). TK enzyme converts the analogues to monophosphorylated molecules, which can themselves be converted by cellular enzymes to nucleotide precursors, which are toxic. These nucleotide analogues can be incorporated into replicating DNA molecules, hence incorporation occurs chiefly in the DNA of dividing cells. This incorporation can result in specific destruction of dividing cells such as cancer cells.

In some cases the gene for a particular antigen can contain a large number of introns or can be from an RNA virus, in these cases a complementary DNA copy (cDNA) can be used. It is also possible that only fragments of nucleotide sequences of genes can be used (where these are sufficient to generate a protective immune response or a specific biological effect) rather than the complete sequence as found in the wild-type organism. Where available, synthetic genes or fragments thereof can also be used. However, the present invention can be used with a wide variety of genes, fragments and the like, and is not limited to those set out above.

Recombinant BAV vectors can be used to express antigens for provision of, for example, subunit vaccines. Antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). An antigenic polypeptide to be expressed by the virus systems of the present invention may contain full-length (or near full-length) sequences encoding antigens or shorter sequences that are antigenic (i.e., encode one or more epitopes). The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host a "protective immune response;" i.e., a humoral (i.e. antibody-mediated), cell-mediated, and/or mucosal immune response that protects an immunized host from infection.

The antigens used in the present invention, particularly when comprised of short oligopeptides, can be conjugated to a vaccine carrier or excipient. Vaccine carriers are well known in the art: for example, bovine serum albumin (BSA), human serum albumin (HSA) and keyhole limpet hemocyanin (KLH). A carrier protein, rotavirus VP6, is disclosed in EPO Pub. No. 0259149, the disclosure of which is incorporated by reference herein.

Genes for desired antigens or coding sequences thereof which can be inserted include those of organisms which cause disease in mammal.

With the recombinant adenovirus vectors of the present invention, it is possible to elicit an immune response against disease antigens and/or provide protection against a wide variety of diseases affecting swine, cattle, humans and other mammals. Any of the recombinant antigenic determinants or recombinant live viruses of the invention can be formulated and used in substantially the same manner as described for the antigenic determinant vaccines or live vaccine vectors.

The present invention also includes compositions comprising a therapeutically effective amount of a recombinant adenovirus vector of the present invention, recombinant virus of the present invention or recombinant protein, prepared according to the methods of the invention, in combination with a pharmaceutically acceptable vehicle (excipient) or carrier and/or an adjuvant. Such a composition can be prepared and dosages determined according to techniques that are well-known in the art. The pharmaceutical compositions of the invention can be administered by any known administration route including, but not limited to, systemically (for example, intravenously, intratracheally, intraperitoneally, intranasally, parenterally, enterically, intramuscularly, subcutaneously, intratumorally or intracranially) or by aerosolization or intrapulmonary instillation. Administration can take place in a single dose or in doses repeated one or more times after certain time intervals. The appropriate administration route and dosage will vary in accordance with the situation (for example, the individual being treated, the disorder to be treated or the gene or polypeptide of interest), but can be determined by one of skill in the art.

The vaccines of the invention carrying foreign genes or fragments can be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. An oral vaccine may be preferable to raise mucosal immunity (which plays an important role in protection against pathogens infecting the gastrointestinal tract) in combination with systemic immunity.

In addition, the vaccine can be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to individuals the vaccine composition(s) of the present invention are within the skill of the art in view of the present disclosure. Those skilled in the art will select a concentration of the vaccine composition in a dose effective to elicit antibody, cell-mediated and/or mucosal immune responses to the antigenic fragment. Within wide limits, the dosage is not believed to be critical.

Typically, the vaccine composition is administered in a manner which will deliver between about 1 to about 1,000 micrograms of the subunit antigen in a convenient volume of vehicle, e.g., about 1-10 ml. Preferably, the dosage in a single immunization will deliver from about 1 to about 500 micrograms of subunit antigen, more preferably about 5-10 to about 100-200 micrograms (e.g., 5-200 micrograms).

The timing of administration may also be important. For example, a primary inoculation may be followed by subsequent booster inoculations, for example, several weeks to several months after the initial immunization, if needed. To insure sustained high levels of protection against disease, it may be helpful to re-administer booster immunizations at regular intervals, for example once every several years. Alternatively, an initial dose may be administered orally followed by later inoculations, or vice versa. Preferred vaccination protocols can be established through routine vaccination protocol experiments.

The dosage for all routes of administration of in vivo recombinant virus vaccine depends on various factors including, the size of patient, nature of infection against which protection is needed, carrier and the like and can readily be determined by those of skill in the art. By way of non-limiting example, a dosage of between approximately $10^3$ pfu and $10^8$ pfu can be used. As with in vitro subunit vaccines, additional dosages can be given as determined by the clinical factors involved.

A problem that has beset the use of adenovirus vectors for immunization and gene delivery in humans is the rapid development of an immunological response (or indeed in some cases existing immunity) to human adenoviruses (HAVs). The recombinant adenovirus vectors of the present invention, for example, comprising BAV packaging domains, are likely to be less immunogenic in humans and, for this and other reasons, will be useful either as a substitute for HAV vectors or in combination with HAV vectors. For example, an initial immunization with a HAV vector can be followed by booster immunizations using an adenovirus vector of the present invention, for example, an adenovirus comprising BAV packaging domain; alternatively, initial immunization with a recombinant adenovirus vector of the present invention, for example, an adenovirus comprising BAV packaging domain, can be followed by booster immunizations with an HAV vector.

The invention also encompasses a method of treatment, according to which a therapeutically effective amount of an adenovirus vector, recombinant adenovirus, or host cell of the invention is administered to a mammalian subject requiring treatment.

When the heterologous sequences encode an antigenic polypeptide, adenovirus vectors comprising insertions of heterologous nucleotide sequences can be used to provide large quantities of antigen which are usefuil, in turn, for the preparation of antibodies. Methods for preparation of antibodies are well-known to those of skill in the art. Briefly, an animal (such as a rabbit) is given an initial subcutaneous injection of antigen plus Freund's complete adjuvant. One to two subsequent injections of antigen plus Freund's incomplete adjuvant are given at approximately 3 week intervals. Approximately 10 days after the final injection, serum is collected and tested for the presence of specific antibody by ELISA, Western Blot, immunoprecipitation, or any other immunological assay known to one of skill in the art.

Adenovirus E1 gene products transactivate many cellular genes; therefore, cell lines which constitutively express E1 proteins can express cellular polypeptides at a higher levels than other cell lines. The recombinant mammalian, particularly bovine, cell lines of the invention can be used to prepare and isolate polypeptides, including those such as (a) proteins associated with adenovirus E1A proteins: e.g. p300, retinoblastoma (Rb) protein, cyclins, kinases and the like; (b) proteins associated with adenovirus E1B protein: e.g. p53 and the like; growth factors, such as epidermal growth factor (EGF), transforming growth factor (TGF) and the like; (d) receptors such as epidermal growth factor receptor (EGF-R), fibroblast growth factor receptor (FGF-R), tumor necrosis factor receptor (TNF-R), insulin-like growth factor receptor (IGF-R), major histocompatibility complex class I receptor and the like; (e) proteins encoded by proto-oncogenes such as protein kinases (tyrosine-specific protein kinases and protein kinases specific for serine or threonine), p21 proteins (guanine nucleotide-binding proteins with GTPase activity) and the like; (f) other cellular proteins such as actins, collagens, fibronectins, integrins, phosphoproteins, proteoglycans, histones and the like, and (g) proteins involved in regulation of transcription such as TATA-box-binding protein (TBP), TBP-associated factors (TAFs), Sp1 binding protein and the like.

The invention also includes a method for delivering a gene to a mammal, such as a bovine, human or other mammal in need thereof, to control a gene deficiency. In one embodiment, the method comprises administering to said mammal a live recombinant adenovirus of the present invention containing a heterologous nucleotide sequence encoding a non-defective form of said gene under conditions wherein the recombinant virus vector genome is incorporated into said mammalian genome or is maintained independently and extrachromosomally to provide expression of the required gene in the target organ or tissue. These kinds of techniques are currently being used by those of skill in the art to replace a defective gene or portion thereof. Examples of foreign genes, such as transgenes, heterologous nucleotide sequences, or portions thereof that can be incorporated for use in gene delivery include, but are not limited to, cystic fibrosis transmembrane conductance regulator gene, human minidystrophin gene, alpha-1-antitrypsin gene and the like.

In particular, the practice of the present invention in regard to gene delivery in humans is intended for the prevention and/or treatment of symptoms diseases including, but not limited to, genetic diseases (for example, hemophilia, thalassemias, emphysema, Gaucher's disease, cystic fibrosis, Duchenne muscular dystrophy, Duchenne's or Becker's myopathy, etc.), cancers, viral diseases (for example, AIDS, herpesvirus infection, cytomegalovirus infection and papillomavirus infection) and the like. For the purposes of the present invention, the vectors, cells and viral particles prepared by the methods of the invention may be introduced into a subject either ex vivo, (i.e., in a cell or cells removed from the patient) or directly in vivo into the body to be treated. In some examples, the host cell is a human cell and, may be a lung, fibroblast, muscle, liver or lymphocytic cell or a cell of the hematopoietic lineage.

The present invention is not to be limited in scope by the specific embodiments described herein. Various modifications of the invention in addition to those described herein will become apparent to those skilled in the art from the foregoing description and accompanying figures. Such modifications are intended to fall within the scope of the appended claims.

EXAMPLES

Example 1

Materials and Methods for Determining Bovine Adenovirus Encapsidation Sequences

Cells and Viruses

VIDO R2 cells (Reddy et al. (1999, *J. Virol.* Vol. 73:91737-9144)) (ATCC accession number PTA-156) were grown and maintained in Eagle's minimum essential medium (MEM) supplemented with 10% fetal bovine serum (FBS). All the mutant and wild-type BAV-3 (strain WBR-1) (Darbyshire et al. (1965, *J. Comp. Patho.* Vol. 75:327-330)) were propagated and titrated on VIDO R2 cells.

Construction of Recombinant Plasmids

Plasmid. pLtRtHind.Mod (FIG. 2A) containing 1.6 Kb left end fragment (nt 1 to 1653)and 1.2 Kb right end fragment (nt 33235 to 34446) of BAV-3 genome was used as template in PCR to create deletion mutations between left inverted terminal repeat (ITR) and ATG of E1 A gene (Reddy et al. (1998,*Virol. Vol* 72:1394-1402)). Nucleotide numbers of the BAV-3 genome referred to herein are given according to GenBank Accession No. AF030154. The primers used in PCR are shown in Table I. The following conditions were used for PCR in a total volume of 50 µl: 0.5 µg of template DNA, 1×PCR buffer [10mM KCl, 10mM (NH$_4$)$_2$SO$_4$, 20mM Tris-Cl (pH 8.75), 2 mM MgSO$_4$, 0.1% Triton®X-100, 0.1 mg/ml BSA] (Stratagene), 0.4 mM dNTPs, 10 pmol of each primer, 2.0 U of cloned pfu DNA polymerase (Stratagene). The cycling conditions were: 94° C. for 2 min to denature the DNA, followed by 30 cycles consisting of 94° C. for 40 seconds (s), 37-50° C. for 40 s, 72° C. for 40 s, and finally, extention at 72° C. for 2 min. The products of PCR were separated on a 1.5% or 2% agarose gel and visualised by ethidium bromide (EtBr) staining.

TABLE I

Primers used in PCR

| Primer | Sequence[a] | BAV-3 nucleotide position[b] | Description |
|---|---|---|---|
| LZP53: | 5'-CGT CTT CAA GGA TCC GAA-3' | | sense, BamHI (SEQ ID NO:3) |
| LZP41: | 5'-ATA CTG CTG CAG CAG CGA-3' | 822-839 | antisense, PstI (SEQ ID NO:4) |
| LZP42: | 5'-CCG CTC GAG GAC GTA GCG GGT GCG GAA-3' | 207-224 | antisense, XhoI (SEQ ID NO:5) |
| LZP43: | 5'-CCG CTC GAG CGT ACT TCC GTG TCA CAT-3' | 311-328 | sense, XhoI (SEQ ID NO:6) |
| BAV-P1: | 5'-CCG GTC GAG AAC ACC AAA AAT CCG CCC-3' | 293-311 | antisense, XhoI (SEQ ID NO:7) |
| BAV-P2: | 5'-CCG CTC GAG GTT TAT GTC CCC GGT CAC-3' | 382-400 | sense, XhoI (SEQ ID NO:8) |

TABLE I-continued

Primers used in PCR

| Primer | Sequence[a] | BAV-3 nucleotide position[b] | Description |
|---|---|---|---|
| BAV-P3: | 5'-CCG CTC GAG CCC GGA AAA GAC GCC GAA-3' | 366-383 | antisense, XhoI (SEQ ID NO:9) |
| BAV-P4: | 5'-CCG CTC GAG GGA ACA TCA AGA ACA AAT-3' | 468-486 | sense, XhoI (SEQ ID NO:10) |
| BAV-P5: | 5'-CCG CTC GAG ACC CTA GGA GAC GAA AAA-3' | 450-467 | antisense, XhoI (SEQ ID NO:11) |
| BAV-P6: | 5'-CCG CTC GAG CAG ACT TTT TCT CAT TTT-3' | 541-558 | sense, XhoI (SEQ ID NO:12) |
| BAV-P7: | 5'-CCG CTC GAG ACG TGT GAA ACG CAG TCC T-3' | 519-537 | antisense, XhoI (SEQ ID NO:13) |
| BAV-P8: | 5'-CCG CTC GAG TCA TTT TCT CAC ACT CCG T-3' | 552-570 | sense, XhoI (SEQ ID NO:14) |
| BAV-P9: | 5'-CGG CTC GAG AAA AAG TCT GTC TAC GTG T-3' | 532-553 | antisense, XhoI (SEQ ID NO:15) |
| BAV-P10: | 5'-CCG CTC GAG TCA CAC TCC GTC GTC CGC T-3' | 560-578 | sense, XhoI (SEQ ID NO:16) |
| PLB5: | 5'-CCG CAA TTG AGT TCC GCA CCC GCT ACG-3' | 205-222 | sense, MfeI (SEQ ID NO:17) |

[a]The restriction endonuclease cleavage sites are underlined.
[b]Numbers indicate the nucleotide position relative to the left terminus of BAV-3 genome. BAV-3 nucleotide sequences are indicated in boldface type.

To construct recombinant transfer plasmids containing the deletions between the left ITR and ATG of E1A gene of BAV-3 (Reddy et al. (1998, J. Virol. Vol72:1394-1402)), first the DNA fragments were amplified using primer pairs LZP53-LZP42, LZP53-(BAV) P1, LZP53-P3, LZP53-P5, LZP53-P7, and LZP53-P9 were digested with BamHI and XhoI. Secondly, the DNA fragments amplified using primer pairs LZP41-LZP43, LZP41-P2, LZP41-P4, LZP41-P6, LZP41-P8, and LZP41-P10 were digested with XhoI and PstI. The appropriate BamHI-XhoI and XhoI-PstI DNA fragments were ligated to BamHI/PstI-digested pLtRtHind-.Mod in a three way ligation, thus creating the recombinant transfer plasmids containing the desired deletions between left-end ITR and ATG codon of E1A gene of BAV-3 (FIGS. 4A, 5A, 6A).

To construct the transfer plasmids containing double deletions (FIG. 7A), the second deletion mutation was introduced in the plasmids containing single deletion mutation in the same way described above.

The plasmids containing the full-length genome of BAV-3 with deletions in the putative packaging domain were generated by homologous recombination in E. coli BJ5183 (Chartier et al. (1996, J. Virol. Vol. 70:4805-4810)) between HindIII-linearized individual recombinant transfer plasmid and the genomic DNA from wild-type BAV-3 (FIG.2B). These plasmids were characterized by restriction endonuclease analysis. The endpoints of deletion mutations introduced into plasmids were determined by nucleotide sequence analysis.

Isolation of BAV-3 Mutants

VIDO R2 cell monolayers were seeded in a 35 mm dish in diameter and were transfected with 5 µg of PacI-digested individual full-length plasmid DNA using the Lipofectin methods according to the instructions of manufacturer (In-vitrogen). After 10 to 15 days of incubation at 37° C., the transfected cells were collected and freezing-thawed three times. The lysates were used to infect the freshly prepared VIDO R2 cells until cytopathic effect appeared. Finally, the recombinant viruses were characterized by PCR and restriction analysis and then expanded and titrated on VIDO R2 cells.

Determination of Virus Yields and Packaging Efficiency.

All viral infections were performed at a multiplicity of infection (MOI) of 5 plaque forming unit (PFU) per cell at 37° C. for 1 h. The cells were washed and fresh medium was added. For the determination of viral yield in single-virus infections, infected VIDO R2 cells were harvested 48 h after infection and then lysed by three cycles of freezing and thawing. The infectious virus yields in cleared lysates were determined by plaque assay on VIDO R2 cells. The data presented for virus yields from single infections represent the averages of three independent experiments.

Packaging efficiency of the mutant viruses was determined by coinfection of VIDO R2 cells with both the mutant and wild-type BAV-3, according to the method described earlier (Grable et al. (1990, J. Virol. Vol. 64:2047-2056); Grable et al. (1992, J. Virol. Vol. 66:723-731)). VIDO R2 cells were infected with 5 PFU of each of the viruses per cell as described above. Forty-eight hours postinfection, one-half of the cells were used to isolate total high-molecular-weight DNA, and the other half of the cells were used to prepare viral DNA from virions. For the isolation of total high-molecular-weight DNA, the infected cells were lysed by the addition of Nonidet P-40 to 0.4%, and then digested with proteinase K at 50° C. for at least 2 hr. The high-molecular-weight DNA was isolated as described previously (Sambrook et al. 1989, Supra). For the isolation of viral DNA from virions, infected cells were precipitated and suspended in lysis buffer (20 mM Tris-Cl[pH8.0], 0.2% deoxycholate, 10% ethanol). After incubation for 60 min at room temperature, the lysate was cleared at 10,000×g for 30 min. The supernatant was adjusted to 2 mM $CaCl_2$ and 2 mM $MgCl_2$, and was digested with 40 µg of RNase A per ml and 10 µg of DNase I per ml at 37° C. for 30 min. The reaction was stopped by the addition of EDTA and EGTA to a final concentration of 50 mM each. Virus particles were lysed by the addition of Sarkosyl to 0.5%, and the samples were digested with 1 mg of proteinase K per ml at 50° C. for 1 h to 2 h. After phenol and chloroform extraction, the viral DNA was precipitated with ethanol. The DNAs isolated from virus-infected cells or virions were digested with XhoI and PstI, and then analyzed by Southern hybridization.

Southern Hybridization

The XhoI and PstI-digested DNAs were separated on 1.5% agarose gel and then transferred to Gene Screen Plus hybridization transfer membrane (Perkin Elmer Life Science) by high salt capillary transfer method according to the instructions of manufacturer. The 280 bp DNA fragment corresponding to nucleotides (nt) 560 and 839 was amplified by PCR with primers BAV-P10 and LZP41, labelled with $^{32}$P-dCTP by using Random Primers DNA labelling system (Invitrogen), and was used as a probe in Southern hybridization. The blots were prehybridized in ULTRAhyb ultrasensitive hybridization buffer (Ambion® RNA) at 42° C. for 30 min, and then $^{32}$P-labeled probes were added. Hybridization was performed at 42° C. overnight. After extensively washing with 0.1×SSC and 0.1% SDS, the blots were exposed to X-ray film (Kodak) without an intensifying screen. The bands in autoradiograms were scanned and their relative intensities were determined and analysed by Computing Densitometer using Alphamager program. The data presented for packaging efficiency based on coinfection experiments represent the averages of three independent experiments.

Example 2

Bovine Adenovirus Encapsidation Sequence

Analysis of BAV-left end Genomic Sequence

The cis-acting packaging domains of HAV-5 were identified to be located at the left end of the viral genome. Due to the similarity of genome organization between HAV-5 and BAV-3, to search the packaging domain of BAV-3, the left end region of BAV-3 genome was reviewed, especially between the left ITR and the start ATG codon of E1A open reading frame (ORF) (FIGS. 1A-1B) (SEQ ID NQ:1). According to the consensus bipartite structure of the dominant cis-acting packaging elements, 5'-TTTGN$_8$CG-3'(SEQ ID NO:2), and/or AT-rich character described for HAV-5 (Schmid et al. (1997, J. Virol. 71:3375-3384), 20 AT-rich units between nucleotides (nt) about 224 and about 560 were found. However, none of them show a perfect homology with 5'-TTTGN$_8$CG-3'(SEQ ID NO:2) sequences. To determine which of these AT-rich elements can mediate in cis the packaging of BAV-3 genome, deletion mutations were introduced into this region on the viral genome, and then the virus mutants were analyzed for packaging efficiency.

Isolation and Analysis of Virus Mutants

Among current methods for generating adenovirus-based mutants, the *E. coli* BJ5183 recombination system is the most simple and efficient (Chartier et al. 1996, Supra). This system was employed to construct and isolate BAV-3 mutants containing deletion mutations in the region of interest. Deletions in BAV-3 genome were initially constructed in a recombinant transfer plasmid by deleting DNA sequences between two PCR products through insertion of two PCR products into BamHI/PstI site of plasmid pLtRtHind.Mod (FIG. 2A) in a three way ligation. The deletions were then rebuilt into intact viral genome by homologous recombination between wild-type BAV-3 genomic DNA and Hind III-linearized recombinant transfer plasmids in *E. coli* BJ5183 cells. The resulting full length plasmids containing the whole genome of BAV-3 with deletion mutations in the desired region were digested with Pac I and then transfected into VIDO R2 cells to rescue the virus mutants containing deletions (FIG. 2B) The mutant BAV-3 was characterized by PCR with primers LZP41 and PLB5 (FIG. 3) and DNA sequence analysis.

The proteins encoded by adenovirus early region 1 (E1) are required for activation of transcription of other early genes and virus replication (Jones et al. (1979, *Proc. Natl. Acad. Sci.* USA Vol. 76:3665-3669); Berk et al. (1979, *Cell*. Vol. 17:935-944); Shenk et al. (1991, *Adv. Cancer Res*. Vol. 57:47-85); Zhou et al. (2001, *Virology* Vol. 288:264-274)). All of the deletion mutations described herein are located between nt about 224 and about 560, which is the location of transcriptional control region of BAV-3 E1 transcription units. The mutations in E1 transcriptional control region alter the expression of early genes including E1A, E1B, E2A, E3, and E4, and subsequently affect the viral growth. VIDO R2 cells (Reddy et al. 1999, Supra) were derived from fetal bovine retina cells (FBRC) by transfection of E1A and E1B genes of HAV-5. VIDO R2 cells could support the replication and growth of a BAV-3 mutant with deletions of E3 and part of E1A (BAV3ΔE1AE3). Therefore, to minimize the effects of altered expression of viral early genes on the growth of BAV-3 mutants, VIDO R2 cells were chosen.

To compare the packaging efficiency of the virus mutants, the methods described previously were used (Grable et al. 1990, Supra; Grable et al. 1992, Supra). Briefly, at first, the virus mutants were used in single infections in VIDOR2 cells, and the infectious virus yield obtained at 2 days after infection was determined by a plaque assay. Secondly, to exclude completely the effects of altered early gene expression, which is independent of viral packaging, coinfection experiments in which VIDO R2 cells were coinfected with a mutant and wild type virus were performed. The coinfecting wild type virus provides normal levels of the viral early and late gene products to complement the mutant with impaired gene expression due to deletion mutations. At 2 days after infection, one-half of the infected cells were used to prepare nuclear high molecular weight DNA, and the other half of the cells were used to prepare viral DNA from virion particles. The coinfecting input mutant and wild-type viral DNAs were distinguished by restriction endonuclease digestion followed by Southern hybridization. By comparing the relative amounts of mutant and wild-type viral DNA present in the nucleus of infected cells with the relative amounts of each viral DNA present in intact virions, the packaging efficiency of virus mutants could be accurately measured, independent of other effects resulted from early and late gene expression. The results shown herein demonstrate that at least part of BAV-3 packaging domains is located between about nt 224 and about nt 541.

Analysis of Mutant Viruses with Internal Deletions

In the first set of mutant viruses analyzed, the BAV-3 genomic DNA sequences between nt 224 and 560 were deleted part by part. The data obtained with these mutants in viral infections are shown in FIG. 4. All the mutant viruses grew as well as the wild type virus did when they were examined in plaque assay on VIDO R2 cells in single infection experiment. In addition, these mutants could replicate efficiently when total nuclear DNA was examined by Southern blot analysis in coinfection experiments. When virion DNA was analyzed, the deletions of sequences between nt 224 and 311; nt 311 and 382; nt 383 and 468; and nt 467 and 541, resulted in an approximate 2 to 4 fold decrease in packaging efficiency in coinfection experiments. In the same experiment, deletions of sequences between nt 537 and 552; and nt 553 and 560, did not result in detectable change in packaging efficiency. These data showed that the sequences between about nt 224 and about nt 541 may contain some domains necessary for packaging viral DNA into virions. However, the data could not rule out the possibility that the sequences between about nt 537 and about nt 560 contain the functional packaging domain. In human adenovirus, the cis-acting packaging domains are functionally redundant and show an important hierarchy. Some of them are dominant and strong for packaging ability, others are weak (Schmid et al. 1997, Supra). If the interval between nt 537 and 560 in BAV-3 contain very weak packaging domain, it would be hard to detect the changes in packaging efficiency in coinfection when this interval was deleted alone with the other potential strong packaging domains intact. To further characterize the genomic region between about nt 224 and 560, other two sets of BAV-3 mutants were constructed and analyzed.

Analysis of Mutant Viruses with Progressive Deletions

The second set of mutant viruses analyzed contain unidirectional deletions which progress from a common site at nt 224 towards the downstream border of the packaging domain. The data obtained with these mutants in viral infections are shown in FIG. 5A. Virus mutant (Bav3-224/382) containing a deletion that extends from nt 224 to 382 showed a 4 fold decrease in viral yield in single infection when analyzed with plaque assay on VIDO R2 cells. In coinfection experiment, the packaging efficiency of this virus was reduced 10 fold when compared with wild-type virus. The deletion of an additional 87 nt (Bav3-224/468) beyond the deletion endpoint in Bav3-224/382 resulted in a 30 fold decrease in virus yields in single infection. However, Bav3-224/468 displayed a reproducible increase in packaging efficiency in coinfection experiment when compared with Bav3-224/382.

The deletion of an additional 74 nt (Bav3-224/541) beyond the downstream endpoint of deletion in Bav3-224/468 resulted in dramatic decrease (about 70 fold) in virus yield in single infection, and an additional decrease in packaging efficiency in coinfection experiments when compared with Bav3-224/382. The mutant virus (Bav3-224/552) carrying an additional deletion between nt 541 and 552 on the background of Bav3-224/541 showed a 135 fold reduction in viral yield in single infection, but a similar packaging efficiency with that of Bav3-224/382 in coinfection. Bav3-224/560, containing the largest deletion (between nt 224 and 560) in this report displayed a similar phenotype with that of Bav3-224/552 in both single infection and coinfection experiments.

Another set of mutant viruses contains unidirectional deletions that progress from a common site at nt 560 towards the upstream border of the packaging domain. The data obtained with these mutants in viral infections are shown in FIGS. 6A-6B. Mutant virus (Bav3-537/560), carrying deletion of sequences between nt 537 and 560, grew as well as the wild-type virus did in both single infection and coinfection experiments. The additional deletion of sequences between nt 467 and 537 (Bav3-467/560) beyond the deletion endpoints of Bav3-537/560 resulted in the wild-type viral yield in single infection and a 3-fold reduction in packaging efficiency in coinfection. The virus Bav3-383/560 and Bav3-311/560, which contain deletions of sequences between nt 383 and 560, and nt 311 and 560, respectively, showed the same phenotype in viral yield in single infection as well as in packaging efficiency in coinfection when compared with that of Bav3-467/560. The above results suggested that the sequences between nt 224 and 541 are critical for BAV-3 DNA packaging, and that the sequences between nt 541 and 560 appear to have no packaging function. In addition, the different sequences between nt 224 and 541 have different importance in viral packaging process.

Analysis of Mutant Viruses Carrying Double Deletions

To further evaluate the sequences between nt 224 and 541, we constructed and analyzed three virus mutants containing double deletions (FIGS. 7A-7B). The first mutant Bav3-224/311:383/541 contains two deletions between nt 224 and 311, and between nt 384 and 541, respectively, with the sequences between nt 311 and 383 intact. The second mutant virus contains deletions of sequences between nt 224 and 311, and between nt 467 and 541, respectively, leaving the sequences between nt 311 and 467 intact. The third mutant contains sequences between nt 382 and 467 intact, with the deletions of sequences between nt 224 and 382, and between nt 467 and 541. Of three mutant viruses, the second mutant displayed the highest virus yields in single infection and the highest packaging efficiency in coinfection. The results suggested that the sequences between nt 311 and 383 have a similar importance with the sequences between nt 382 and 467 for viral packaging.

The above analysis demonstrates that the BAV-3 sequences between about nt 224 and about 541 contain cis-acting packaging elements. Without being bound by theory, the data shown herein suggest that the cis-acting packaging domain of BAV-3 is composed of redundant functional elements with different importance for viral packaging.

Results

As described herein, the cis-acting packaging signal of BAV-3 is identified. On the basis of analysis of BAV3 genomic DNA sequences and its comparison with that of human adenovirus, 20 AT-rich elements were found located between the left ITR and start ATG codon of E1 A gene on the BAV-3 genome, but none of them showed a perfect homology with the consensus packaging motif (5'-TTTGN$_8$CG-3') (SEQ ID NO:2) of HAV5. However, deletions in this region resulted in reduction in packaging efficiency in coinfection experiments. To determine the upstream and downstream borders of the packaging domain, the additional deletion mutations were rebuilt in the BAV3 genome sequentially. The mutant virus (Bav3-224/560) containing the largest deletion between nt 224 and 560 (FIG. 5A) in this report remained viable in VIIDO R2 cells, but the packaging ability had been reduced dramatically. This suggests that there should be other packaging domains located beyond this region. Left ITR, right end of BAV3 genome, or ORF of E1 A gene are all the possible locations for other potential packaging domain.

A number of mutant viruses displayed a very complex phenotype, which showed an apparent contradiction between the results obtained in single infection and those obtained in coinfection experiments. First, some of mutants exhibited packaging defects in coinfections, however, they grew as well as the wild-type virus did in single infection. To determine the virus yields in single infection, we performed the plaque assay on VIDO R2 cells. Among the biological assays for quantification of the adenovirus, plaque assay is widely used. Detection of the viable virions in this assay involves infection of a cell in a cultured monolayer by a virion suspended in the medium above the cells followed by virion replication and spread of infection to nearby cells sufficient to form a visible plaque in the cell monolayer (Mittereder et al. (1996, *J. Virol.* Vol. 70:7498-7509)). This process depends on the functionality of both virus and the cell target under the same conditions. For a specific virus, the abilities to produce infectious progeny and form visible plaque on permissive cells determine the accuracy of the result obtained with plaque assay. For some mutant viruses such as Bav3-224/311, Bav3-312/382, Bav3-383/468, Bav3-

467/541, about 2 to 4 fold reduction in packaging efficiency in coinfection when compared with wild-type virus was detected. However, in single infection, no difference in viral yields was observed between mutant and wild type virus. Without being bound by theory, the explanation for this phenomenon could be that BAV-3 produced a great number of very small plaques that could not be recognized under light microscopy.

Second, some mutants exhibited only about 10 to 25 fold reduction in packaging efficiency in coinfection, but they displayed about thirty to more than one hundred fold reduction in viral yield in single infection. In HAV-5, the cis-acting packaging domain overlaps two distinct enhancer elements (Hearing et al. 1983, Supra; Hearing et al. 1986, Supra). Enhancer element I specifically regulates the E1A transcription, but enhancer element II enhances transcription from each of the viral early transcription units. The defects in viral yields with enhancer element I or II mutants can be efficiently complemented in trans in 293 cells that constitutively express the viral E1A and E1B gene products (Graham et al. (1977, J. Gen. Virol. Jul. 36(1):59-74)) or in a mixed infection with wild-type viruses in which the wild-type viruses provide early proteins required for efficient viral replication. In the case of BAV-3, a transcriptional control region for E1 genes has been functionally identified between left ITR and ATG codon of E1A gene, in which all the mutants in this report contain the deletion mutations. The results suggested that the packaging defects in mutants in coinfections account for only a portion of the defect observed in virus yields in single infection. The deletion mutations introduced into viral genome impaired the additional other functions required for normal viral replication as well as the packaging ability. The dramatic reduction in virus yield in single infection could come from the combined effects of these known and unknown impaired functions.

Third, the deletion of sequences-between about nt 383 and about 468 in mutant Bav3-383/468 resulted in about 2 fold reduction in packaging efficiency in coinfection, indicating that this region contains cis-acting packaging elements. Unexpectedly, on the background of Bav3-224/382, an additional deletion of sequences between about nt 382 and about 468 resulted in an increase instead of corresponding decrease in packaging efficiency when compared with Bav3-224/382 in coinfection although the viral yield had been further reduced dramatically. The results provide further evidence to the possibility that there would be functional packaging domain(s) located beyond the region of about nt 224 to about 560. Despite the packaging domain of human adenovirus showing a positional flexibility, it must be located within 600 bp of the genomic terminus for its proper function (Hammarskjoeld et al. (1980, Cell. Vol. 20:787-795); Hearing et al. (1987, J. Virol. Vol. 61:2555-2558)). As proposed by Schmid et al. 1998, Supra this implied that the left ITR maybe involved in the packaging process of adenovirus. The deletions may change the structure of the left end genome of BAV3, and then relocate some sequences, for instance, that in ORF of E1A gene, closer to the left ITR to come into function to complement the missing of original packaging domains.

Bovine adenoviruses are usually divided into subgroup I and II on the basis of the differences in their biological and serological distinctiveness (Bartha et al. (1969, Acta Vet. Acad. Sci. Hung. Vol. 19:319-321)). The representatives of subgroup I include the BAV type 1 (BAV-1),BAV-2, -3, and -9. The members of subgroup II include BAV-4, -5, -6, -7, -8, and -11. Aside from BAV-3, the complete genomic sequences of BAV-2 (GenBank accession number AF252854) and BAV-4 (strain THT/62, GenBank accession number AF036092) are available at present. The common character of sequences of left end genome of these BAVs is that there are 15 to 26 AT-rich units located between the left ITR and ATG codon of E1A gene. Additional BAV encapsidation sequences, such as for example, BAV-2 and BAV-4 encapsidation sequences can be identified based on sequence identity and/or location with respect to BAV-3 using the methods disclosed herein.

Example 3

Materials and Methods for Identification of E1 Transcriptional Control Regions

Viruses and Cells

The mutant and wild-type BAV-3 (strain WBR-1) (Darbyshire et al. (1965, J. Comp. Patho. Vol. 75:327-330)) were cultivated in Madin-Darby bovine kidney cells (MDBK) and VIDO R2 cells (Reddy et al. (1999, J. Virol. Vol. 73:9137-9144)). VIDO R2 is a transformed fetal bovine retina cell (FBRC) line expressing the E1A and E1B proteins of human adenovirus type 5(HAV-5) under the control of mouse phosphoglycerate kinase gene promoter. The cells were grown and maintained in monolayer in Eagle's minimum essential medium (MEM) supplemented with 10% heat-inactivated fetal bovine serum (FBS) and antibiotics. The viral titres were determined by plaque assay on VIDO R2 cells.

Construction and Propagation of Viral Mutants.

Construction and propagation of BAV-3 mutants are described herein. Briefly, deletion mutations in BAV-3 E1A 5'-flanking sequences between the end of left inverted terminal repeat (ITR) and the start ATG codon of E1A gene were initially constructed in a plasmid pLtRtHind.Mod by virtue of PCR method. Plasmid pLtRtHind.Mod contains 1.6 Kb left end fragment (nt 1 to 1653) and 1.2 Kb right end fragment (nt 33235 to 34446) of BAV-3 genome. DNA sequences located between two PCR products were deleted through insertion of two PCR products into BanHI/PstI site of pLtRtHind.Mod in a three-way ligation. Deletion mutations were then rebuilt into intact viral genome using the E. coli BJ5183 homologous recombination system (Chartier et al. 1996, Supra) to create the deletion mutation-containing full-length plasmids. The exact endpoints of each deletion were determined by nucleotide sequence analysis. Virus mutants were isolated by transfection of the resulting full-length plasmids into VIDO R2 cells using Lipfectin methods according to the instructions of manufacturer (Gibco BRL) after removal of vector backbone by PacI digestion. Mutant viruses were plaque-purified and characterized by PCR and restriction analysis. Virus stock was prepared by growing virus on VIDO R2 cells, titrated by plaque assay, and then preserved in −80° C.

DNA Probes $^{32}$P-dCTP-labeled DNA probes used in Northern and Southern hybridizations were generated by using Random primers DNA labeling system according to the instructions of manufacturer (Invitrogen). BAV-3 fragments used for preparation of probes were summarized in Table II.

TABLE II

Probes in Northern and Southern hybridizations.

| Probes | Nucleotide position[a] |
|---|---|
| E1A[b] | 560-1156 |
| E1B[c] | 1398-1651 |
| E2A[d] | 21283-22576 |
| E3[e] | 27273-27959 |
| E4[f] | 33232-33905 |
| Southern blot[g] | 828-1651 |

[a]Numbers indicate the nucleotide position (nt) relative to the left terminus of wild-type BAV-3 genome (GenBank accession No. AF030154). BAV-3 nucleotide sequences are indicated in boldface type.
[b]0.59 Kb DNA fragment was released from recombinant transfer plasmid pBAVL12.1 digested with XhoI and EcoRI.
[c]0.25 Kb AscI/HindIII fragment released from plasmid pLtRtHind.Mod (Xing et al., 2003) containing the left end (nt 1-1653) of BAV-3 genome.
[d]1.3 Kb DNA fragment was generated by PCR using primers dbp1416 (5'-GCGTCGACTTAAAACAAAGAGTCAT-3' (SEQ ID NO: 18), sense, nt 21283-21300) and dbp125 (5'-CGGGATCCGCAGCGGTGACTTAAC-3' (SEQ ID NO: 19), antisense, nt 22576-22560).
[e]0.68 Kb HpaI fragment released from recombinant plasmid PUC18 containing BamHI D fragment (nt 26319-29338) of BAV-3 genome.
[f]0.67 Kb ScaI/HindIII fragment released from pLtRtHind.Mod.
[g]0.82 Kb DNA fragment was released from pLtRtHind.Mod digested with PstI and HindIII.

PCR

The wild-type BAV-3 genomic DNAs were used as templates in PCR amplifications. The following conditions were used for PCR in a total volume of 50 µl: 0.5 µg of template DNA, 1×PCR buffer [10 mM KCl, 10 mM $(NH_4)_2SO_4$, 20 mM Tris-Cl (pH 8.75), 2 m $MgSO_4$, 0.1% Triton®X-100, 0.1 mg/ml BSA] (Stratagene), 0.4 mM dNTPs, 10 pmol of each primer, 2.0 U of cloned pfu DNA polymerase (Stratagene). The cycling conditions were: 94° C. for 2 min to denature the DNA, followed by 35 cycles consisting of 94° C. for 40 s, 50° C. for 40 72° C. for 40 s, and finally, extention at 72° C. for 2 min.

RNA Preparation and Northern Blot.

To prepare RNAs, MDBK cells were infected with virus at multiplicity of infection (MOI) of 40 plaque-forming unit (PFU) per cell for 2 h at 37° C. MEM containing 10% heat-inactivated fetal bovine serum (FBS) and 125 µg/ml AraC was then added. Infected cells were harvested at 7 h after infection and the total RNA was isolated with TRIzol reagent (Gibco BRL) according to the manufacturer's instructions.

For Northern blot analysis, 20 µg total RNAs were separated in denaturing 1% agarose-2.2 M formaldehyde gels by electrophoresis for 3 h, and then were blotted onto the Gene Screen Plus hybridization transfer membrane (Perkin Elmer Life Science Inc.) according to the manufacturer's instruction. The membranes were baked for 2 h at 80° C. in a vacuum oven and then soaked in hybridization buffer [ULTRAhyb ultrasensitive hybridization solution (Ambion RNA company)] for 0.5 h at 42° C. Northern hybridization was performed with hybridization buffer containing $^{32}P$-labeled DNA probes. After hybridization at 42° C. overnight, the membranes were washed twice with 2×SSC and 0.1% SDS at room temperature, and then they were washed twice with 0.1×SSC and 0.1% SDS at 50° C. for 30 min. Membranes were dried and then exposed to X-ray film (Kodak). The RNA bands on the autoradiograms were quantitated with computing densitometer using Alphamager program.

DNA Preparation and Southern Blot

To prepare DNA, MDBK or VIDO R2 cells were infected with wild-type or mutant virus at a MOI of 5 PFU per cell for 2 h at 37° C. The infected cells were harvested at 9, 17, and 25 h after infection, and then resuspended in extraction buffer (10 mM Tris-Cl, 0.1M EDTA, 20 µg RNase per ml, 0.5% SDS, pH8.0) containing proteinase K at the concentration of 100 µg per ml. After incubation at 50° C. for at least 2 h, phenol and chloroform extractions were performed (Sambrook et al., 1989). DNAs were precipitated by ethanol and dissolved in TE buffer (10 mM Tris-Cl, 1 mM EDTA, pH 8.0). DNA was digested with EcoRI and then loaded into 1% agarose gel. Southern hybridization was performed with a standard procedure (Sambrook et al. 1989, Supra). The relative intensities of DNA bands on the autoradiograms were measured with computer-assistant Alphamager program.

Viral Growth Curves

To determine the growth kinetics of virus mutants, VIDO R2 and MDBK cells were infected with wild-type or mutant viruses at a MOI of 5 PFU per cell for 2 h at 37° C. After washing with phosphate-buffered saline (PBS), MEM containing 10% FBS was added. Infected cells were harvested at indicated time points after infection. Viral progeny was released into MEM by treating the infected cells with freezing and thawing at −80° C. and 37° C. for three times. The titers of infectious viral progeny were determined by plaque assay on VIDO R2 cells and expressed as plaque-forming unit (PFU) per ml.

Example 4

Bovine Adenovirus E1 Transcriptional Control Regions

Construction and Propagation of Viral Mutants

Deletion mutations in the BAV-3 E1A 5'-flanking sequences were initially constructed in a transfer plasmid (pLtRtHind.Mod) containing a 1.6 kb left end fragment and a 1.2 kb right end fragment of BAV-3 genome with the aid of PCR by deleting DNA sequences located between two PCR products. The exact site of each deletion was determined by nucleotide sequences analysis. A select group of mutations were introduced into intact viral genome by homologous recombination between HindIII-linearized deletion mutation-containing transfer plasmids and the wild-type BAV-3 genomic DNA in E. coli BJ5183 cells (Chartier et al. 1996, Supra), and are diagrammed in FIG. 8. The resulting full-length plasmids containing BAV-3 genome with the deletions in the desired region were digested with PacI and subsequently transfected into VIDO R2 cells to rescue BAV-3 mutants. Virus mutants were characterized by PCR and restriction analysis, and propagated in VIDO R2 cells.

The mutations cover a 337 base pair (bp) region from the end of BAV-3 left ITR through most of the 5'-noncoding region of the E1A mRNAs. To analyze this region more thoroughly, two new virus mutants designated as Bav36 and Bav58 were constructed for this study. Other virus mutants studied include Bav12 (Bav3-224/311), Bav34 (Bav3-311/382), Bav56 (Bav3-383/468), Bav78 (Bav3-467/541), Bav912 (Bav3-537/560), and Bav14 (Bav3-224/382) in this study.

To verify that each of the mutant stocks was titrated accurately and that the viral input is the same in the experiments, MDBK cells were infected with the virus mutants, and viral DNA present in the nucleus at 6 h after infection was isolated and analyzed by Southern hybridization. Each of the mutant viruses displayed comparable levels of nuclear DNA at early times after infection.

E1A 5'-flanking sequences contain regulatory region (designated as Region I) for E1A transcription.

Figures 9A, 9B, 9C, 9D, 9E, 9F:
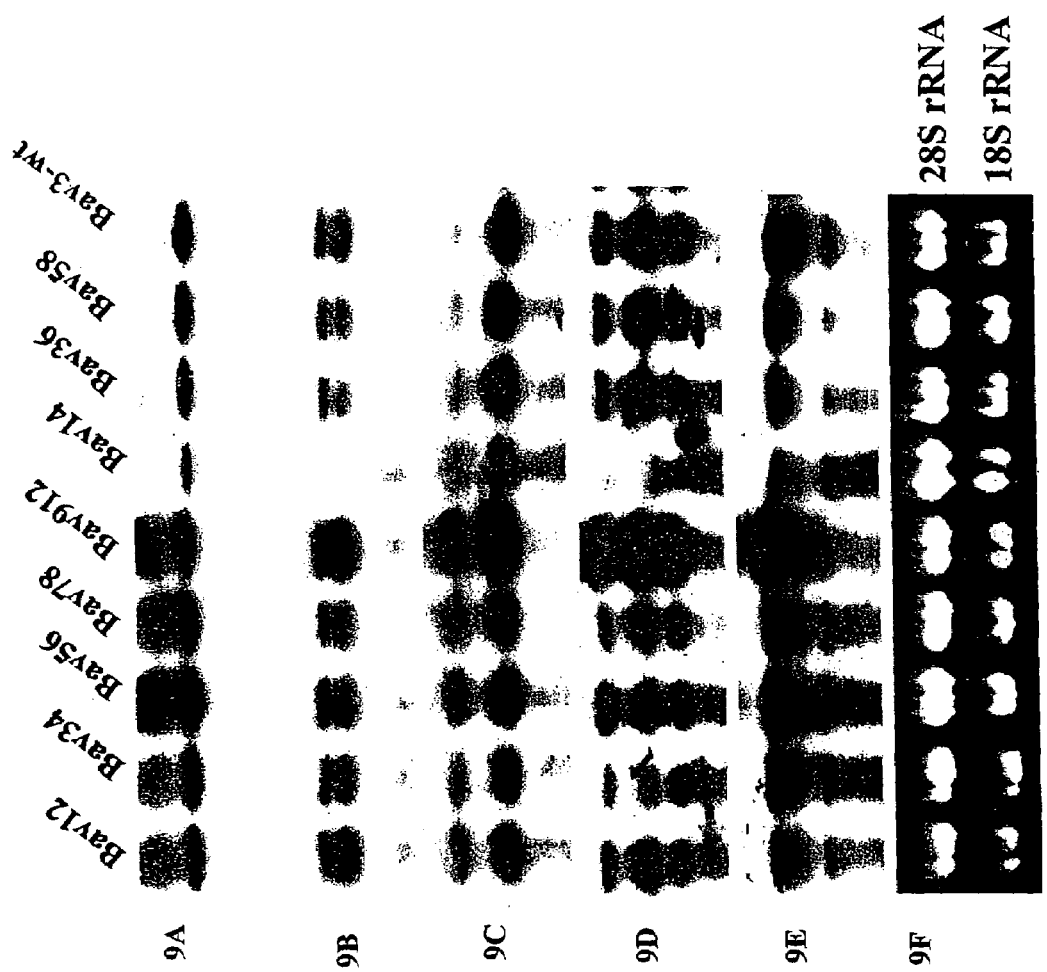

To test the effects of the deletion mutations diagrammed in FIG. 8 on the E1A transcription, MDBK cells were infected with wild-type or mutant viruses at a MOI of 40 PFU per cell, and the cytoplasmic RNA was isolated at early times (7 h) after infection. The steady-state levels of E1A mRNAs produced early in infection were determined by Northern blot analysis using a uniformly $^{32}$P-labeled E1A-specific DNA probe. The results are shown in FIG. 9A. Wild-type BAV-3 is included as a control throughout this study. The virus mutants Bav12, Bav34, Bav56, Bav78, and Bav912 produced E1A mRNAs as nearly efficiently as the wild-type BAV-3 did. Bav14, lacking the sequences between nucleotide position (nt) 224 and 382, displayed the largest reduction (about 3 fold) in the level of E1A mRNAs compared to that of wild-type BAV-3. Bav36 and Bav58 showed a modest reduction. The transcription start site of E1A mRNA is located between nt 296 and 298 (Reddy et al. 1998, *J. Virol.* Vol. 72:1394-1402)), and deleted in both Bav12 and Bav14. However, the former did not show reduction in E1A transcription. The results suggested that the reduction in E1A transcription in Bav14 did not result from the removal of the transcription start site, and that the regulatory element might be located in the conjunction of two deletions in Bav12 (between nt 224 and 311)and Bav34 (between nt 311 and 382), or might be functionally redundant.

The cis-acting packaging domain of BAV-3 is located between about nt 224 and about 540 in the E1A 5'-flanking region. The deletions in this region decreased the ability of virus to package genomic DNA into virions. This defect could indirectly affect the transcription by reducing production of infectious viral progeny that was used as template for transcription. To isolate the total RNA, virus infection was performed in the presence of AraC at a concentration of 125 μg/ml at which the replication of viral DNA was effectively inhibited. Additionally, the RNA was isolated at early times (7 h) after infection. These rule out the possibility that reduction in E1A transcription was due to the packaging defect. The fact that the deleted sequences in Bav12, Bav34, Bav56, and Bav78 also contain the cis-acting packaging domains but the E1A mRNA transcription had not changed, provided further evidence that the E1A 5'-flanking region did contain transcriptional control elements.

Deletion in Bav14 (between nt 224 and 382) partially overlaps with that in Bav36 (between nt 311 and 468). The former displayed a reduction more than the latter in E1A transcription. This result suggested that the sequences between nt 224 and 311 could play a more important role in the transcription regulation than the region between nt 382 and 468.

A functionally independent region (designated as Region II) directly controls the E1B transcription.

The E1A transcription unit of Bav-3 lies between 0.8 and 10.5 mu. It overlaps with the E1B unit that is located between 4.2 and 10.5 mu (Reddy et al. 1999, Supra). To test if the regulatory sequences in the 5'-flanking region of E1A can modulate the E1B mRNA transcription, the RNA was analyzed by Northern hybridization using $^{32}$P-labeled E1B probes (Table II). The largest decrease (about 10 fold) in E1B mRNA accumulation is evident in Bav14-infected cells. Bav36 and Bav58 also displayed a lower level of E1B mRNAs compared to that of wild-type virus. Bav912 transcribed E1A mRNAs as efficiently as the wild-type BAV-3 did. However, the steady-state level of E1B mRNA is higher than that of wild-type virus (FIG. 9B). It appears that the E1A 5'-flanking region contains regulatory element directly responsible for E1B transcription unit.

Adenovirus early region 2 (E2)contains E2A (DNA binding protein, DBP) and E2B (DNA polymerase, and preterminal protein). The proteins encoded by E2 genes are directly involved in viral DNA synthesis (Russell (2000, *J. Gen. Virol.* Vol. 81:2573-2604); Reddy et al. (1998, *J. Virol.* Vol. 72:1394-1402)). To investigate the E2A gene transcription, Northern blot was performed with the $^{32}$P-labeled DBP gene as probes. The results were shown in FIG. 9C. Bav14 displayed a dramatic decrease in E2A mRNA accumulation. Bav36 showed a modest decrease in E2A transcription. In contrast, Bav912, which displayed a higher level of E1B mRNA, showed a much greater increase in E2A mRNA transcription.

BAV-3 early region 3 (E3)is located between the genes coding for pVIII and fiber proteins (Reddy et al. 1998, Supra). The TATA box of E3 gene promoter is at nt 26154. This region is transcribed in the same direction and located on the same DNA strand of BAV-3 genome as the E1 region. To analyze the transcription of E3 gene, the RNA was tested with a $^{32}$P-labeled E3 probe (Table II). As shown in FIG. 9D, the results were similar to that of E2A. Bav912 showed increased transcription efficiency. The reduction in levels of E3 mRNAs was evident with Bav14 and Bav36.

The early region 4 (E4) of BAV-3 lies near the right end of the genome (nt 30932 to 33950)(Reddy et al. 1998, Supra; Baxi et al. 1999, Supra). The promoter activity of E4 region was examined with Northern blot analysis. The results are shown in FIG. 9E. The reduced E4 transcription was detected in Bav14 and Bav36-infected cells. Bav912 displayed an enhancement in E4 transcription compared to wild-type BAV-3.

Effects of Deletion of Regulatory Region I and II on Viral Replication.

The DNA replication of adenovirus is controlled by the expression of viral early genes (Russell, (2000, *J. Gen. Virol.* Vol. 81:2573-2604); Reddy et al. 1998, Supra). To investigate the influences of altered early gene transcription on the replication of BAV-3 in infected cells, the infectious viral progeny production and viral genomic DNA accumulation were examined on both VIDO R2 and MDBK cells which are widely used in BAV-3 study. VIDO R2 cells, which derived from fetal bovine retina cells (FBRC) transformed by HAV-5 E1A and E1B genes (Reddy et al. 1999, Supra), could complement the BAV-3 mutant defective for E1A gene expression. Both cells were infected with wild-type or mutant viruses at a MOI of 5 PFU per cell. At 12, 24, 36, and 48 h after infection, infected cells were collected and the viral particles were released by three cycles of freezing and thawing. The titres of virus lysate were determined by plaque assay on VIDO R2 cells. Data obtained in this experiment are shown in FIGS. 10A-10B. Mutant viruses Bav12, Bav34, Bav56, and Bav78, produced a nearly phenotypically wild-type viruses on VIDO R2 cells (FIG. 10A). Bav14 carried the deletion of sequences between nt 224 and 382 and produced a defective virus which grew to a level 3 fold below the wild-type level on VIDO R2 cells at 48 h postinfection. Bav36, carrying a deletion of sequences between nt 311 and 468, which contains a 72 bp sequences between nt 311 and 382 overlapping with the deleted sequences in Bav14 (between nt 224 and 382), produced viruses that were slightly defective for growing on VIDO R2 cells (levels within twofold below the wild-type level). Bav912 carrying a deletion between nt 537 and 560, produced a slightly higher titres. The mutant viruses displayed the similar growth properties on MDBK cells (FIG. 10B)

with that on VIDO R2 cells. Both wild-type and mutant viruses displayed a more production of infectious viral progeny on MDBK cells than on VIDO R2 cells. We noticed that although the HAV-5 E1 gene products constitutively expressed in VIDO R2 cells complemented the mutant BAV-3 defective for E1A expression, mutant virus Bav14, which had the most dramatic reduction in E1A transcription, showed the largest lag in growth on VIDO R2 cells as well as on MDBK cells. The packaging domains of BAV-3 are located between about nt 224 and about 541. Deletion of these sequences decreased the packaging efficiency of mutant viruses below the wild-type level. Except Bav912, all of the virus mutants carry the deletion of the cis-acting packaging domains. The reduced packaging efficiency could also result in the defective growth of virus. To minimize the effects of defect in packaging efficiency on the viral growth, the viral DNA accumulation was examined on both VIDO R2 and MDBK cells. The cells were infected with wild-type or mutant viruses at a MOI of 5 pfu per cell as described above, and were harvested at 9, 17, and 25 h after infection. Total DNA was isolated and digested with EcoRI. Fractionated DNAs on 1% agarose gel were then analyzed by Southern hybridization. The results of a representative DNA accumulation experiment are shown in FIGS. 11A-11B. In both VIDO R2 cells (FIG. 11A) and MDBK cells (FIG. 11B), Bav14 (carrying deletion of region I) and Bav912 (carrying deletion of region II) showed slightly decreased and increased rates of DNA accumulation, respectively, when compared with wild-type virus. In addition, both wild-type and mutant BAV-3 replicated more efficiently in MDBK cells than in VIDO R2 cells. This is in good agreement with the results of viral growth curve on both cell lines.

Results

The Northern blot analysis of a series of virus mutants containing deletions in the BAV-3 E1A 5'-flanking sequences between the left ITR and the start ATG codon of E1A defines two functionally separate transcriptional control regions for viral early genes. Region I is mainly located between about nt 224 and about nt 382. Deletion of this region dramatically decreased the transcription of all tested early genes including E1A, E1B, E2A, E3, and E4. However, the deletion of half this region in Bav12 and Bav34, did not lead to reduction in E1A transcription. The slight reduction in E1A gene transcription in Bav36, which contains deletion of sequences between about nt 311 and about nt 468, overlapping with the deleted sequences (between about nt 311 and about nt 382)in Bav34, demonstrated that sequences between about nt 382 and about 468 are also necessary for E1A gene transcription.

On the basis of experimental results, to further define the structure of E1A transcriptional control region, the left end genomic sequences of BAV-3 with two software programs. The program I (Neural network promoter prediction, fruitflv.org/seq tools/promoter (Reese, et al. (1995, The Seventh International Genome Sequencing and Analysis Conference, Hilton Head Island, South Carolina); Reese, et al. (1996, Biocomputing: Proceedings of the 1996 Pacific Symposium, edited by Lawrence Hunter and Terri E. Klein, World Scientific Publishing Co., Singapore, 1996, Jan. 2-7)) was used to search potential eukaryotic promoter. The program II (Hctata: Hamming-Clustering method for TATA signal prediction in eukaryotic genes. In: Tools for prediction and analysis of protein-coding gene structure. 125.itba.mi.cnr.it/~webgene/wwwHC tata (Milanesi et al. (1995, Proceedings of the Third International Symposium on Bioinformatics, World Scientific Publishing, Singapore, 461-466); Milanesi et al. (1996, Comput. Applic. Biosci. Vol. 12:399-404); Milanesi et al. (1998, Guide to Human Genome Computing (2nd Edition, ed. M.J. Bishop) Academic Press, Cambridge, 215-256); Milanesi et al. (1999, Bioformatics Vol. 15:612-621) was used to predict the potential TAT box, the core component of TATA box-containing eukaryotic promoter (Hampsey et al. (1998, Microbiol. Mol. Biol. Vol. 62:465-503)). The results are diagrammed in FIG. 12. Program 1 suggests the E1 A gene is under the control of a TATA-less promoter that is probably located in the ITR between about nt 94 and about nt 211. The region between about nt 94 and 211 contains GC-rich sequences, which may be SP1 binding sites (Hatfield et al. (1993, J. Virol. Vol. 67:3931-3939); Kadonaga et al. (1987, Cell. Vol. 51:1079-1090)). It has been reported that the deletion of 72 base pair (bp) sequences between about nt 89 and about nt 162, overlapping most sequences of potential promoter predicted by program I, did not seem to have any effect on the kinetics of viral replication compared to wild-type BAV-3 (van Olphen, (2002, Intervirology Vol. 45:188-192)). Without being bound by theory, the results indirectly suggest that GC-rich sequences between about nt 94 and about nt 211 could not be the major promoter region E1A. The program II also suggests that the E1 A gene promoter is located in an ITR, but it could contain a TATA box with the sequences 'TATGA' between about nt 68 and about nt 72. Additionally, the CAAT element of eukaryotic protein-coding gene promoter was found between about nt 46 and 49, upstream of potential TATA box (Reddy et al. (1998, Supra; Reddy et al. 1999b, Supra). Based on the experimental results and promoter prediction, we conclude that the region I, the regulatory control region, rather than the core promoter region.

The deletion of Region I reduced the transcription of all tested early genes including E1B, E2A, E3, and E4. In HAV, E1A transcriptional control region contains an enhancer element II which enhances in cis all of the early gene transcription on the viral genome (Hearing et al. 1983, Supra; Hearing et al. 1986, Supra). In addition, the E1 gene products are required for activation of other early gene promoters (Berk et al. (1979, Cell. Vol. 17:935-944); Jones et al. (1979, Proc. Natl. Acad. Sci. USA Vol. 76:3665-3669); Grand et al. (1987, Biochem. J. Vol. 241:25-38)). However, in the case of BAV-3, it could not be determined if the decreased transcription of E1B, E2A, E3, and E4 is due to the cis-acting effects of Region I deletion, or due to the trans-acting effects of decreased E1A transcription.

The second transcriptional control region (region II) disclosed herein is located between about nt 537 and about nt 560 relative to the left terminus of BAV-3 genome. Deletion of Region II (Bav912) has no effects on the accumulation of E1A mRNAs early after infection (7 h), but directly increased the E1B mRNA level. In addition, the enhancement of transcription of E2A, E3, and E4 was evident with mutant Bav912. However, by analysis of virus mutants constructed, it is not known if the enhanced transcription of E2A, E3, and E4 is cis-acting or trans-acting effects.

In the left 11% of the HAV genome, there are three transcription units, E1A, E1B, and pIX. Each of unit has its own promoter and poly (A) signal and poly(A) site (Babiss et al. (1991, J. Virol. Vol. 65:598-605); Bos et al. (1983, EMBO J. Vol. 2:73-76); Maat et al. (1980, Gene. Vol. 10:27-38)). In BAV-3, the transcripts of E1A, E1B, and pIX are 3'-coterminal (Reddy et al. 1998, Supra; Reddy et al. 1999b, Supra; Zheng et al. 1999, Supra). The transcriptional unit of pIX is transcribed form an independent promoter and encodes a structural component of the adenoviral capsid. The result that the deletion of region I in Bav14 reduced simultaneously the steady-state levels of E1A and E1B raises a possibility that E1A and E1B maybe share some common sequences as the transcriptional control elements.

The invention claimed is:

1. An isolated bovine adenovirus sequence, wherein said sequence consists of the sequence between nucleotide (nt) 224 and nt 541 of the sequence as shown in SEQ ID NO:1, or a portion of said sequence, wherein said sequence, or portion thereof, is capable of encapsidating an adenovirus genome.

2. A recombinant vector comprising the isolated bovine adenovirus sequence of claim 1.

3. The recombinant vector of claim 2 wherein said vector is an adenovirus vector.

4. The recombinant adenovirus vector according to claim 3 wherein said vector is a bovine adenovirus vector.

5. The recombinant adenovirus vector according to claim 3 wherein said bovine adenovirus sequence is heterologous to said adenovirus vector.

6. The recombinant adenovirus vector according to claim 5 wherein said adenovirus vector further comprises human adenoviral sequences, porcine adenoviral sequences, or canine adenovirus sequences.

7. The recombinant adenovirus vector according to claim 3 wherein said adenovirus vector is replication-competent.

8. The recombinant adenovirus vector according to claim 3 wherein said adenovirus vector is replication-defective.

9. The recombinant adenovirus vector according to claim 3 wherein said vector further comprises at least one nucleic acid sequence encoding a heterologous protein.

10. The recombinant adenovirus vector according to claim 9 wherein said vector further comprises at least two inverted terminal repeat (ITR) sequence.

11. The recombinant adenovirus vector according to claim 3 wherein said adenovirus vector comprises a bovine adenovirus sequence(s) essential for encapsidation, wherein said sequence is between nt 224 and nt 541 of the sequence as shown in SEQ ID NO: 1, or a portion of said sequence, wherein said sequence, or portion thereof, is capable of encapsidating an adenovirus genome, and a nucleic acid sequence encoding a heterologous protein, wherein said adenovirus vector is deleted in part or all of one or more nucleic acid sequences encoding adenovirus proteins necessary for replication and is replication-defective.

12. The recombinant adenovirus vector according to claim 11, wherein said adenovirus vector further comprises human adenovirus sequences, bovine adenovirus sequences, porcine adenovirus sequences, and/or canine adenovirus sequences.

13. The recombinant adenovirus vector according to claim 9 or 11 wherein said heterologous protein encodes an immunogenic polypeptide.

14. The recombinant adenovirus vector according to claim 9 or 11 wherein said heterologous protein encodes an antigen of a pathogen.

15. The recombinant adenovirus vector according to claim 14 wherein said pathogen is selected from the group consisting of a human pathogen, a bovine pathogen, a porcine pathogen, and a canine pathogen.

16. A host cell comprising the adenovirus vector according to claim 3.

17. The host cell according to claim 16 which is a mammalian cell.

18. The host cell according to claim 16 which is a bovine cell.

19. The host cell according to claim 17 which is a human cell.

20. A recombinant adenoviral particle comprising the adenoviral vector according to claim 3.

21. A composition comprising the adenoviral vector according to claim 3.

22. A composition comprising the adenoviral particle of claim 20.

23. The composition according to claim 21 further comprising a pharmaceutically acceptable excipient.

24. The composition according to claim 22 further comprising a pharmaceutically acceptable excipient.

25. A composition capable of inducing an immune response in a mammalian subject, said composition comprising an adenovirus vector of claim 13 and a pharmaceutically acceptable excipient.

26. A method for eliciting an immune response in a mammalian subject comprising administering a composition of claim 25 to the mammalian subject.

27. A method of preparing an adenovirus comprising, culturing a cell under conditions suitable for production of adenovirus, wherein said cell comprises a recombinant adenovirus vector which comprises an isolated bovine adenovirus sequence(s) of claim 1 wherein said adenovirus vector is deleted in part or all of one or more adenoviral proteins necessary for replication and is cultured in the presence of a helper virus that comprises nucleic acid encoding one or more adenovirus proteins necessary for replication of said adenovirus; and optionally recovering said adenovirus.

28. The method according to claim 27 wherein said adenovirus comprises a mammalian ITR sequence.

29. The method of claim 27 wherein said adenovirus further comprises a nucleic acid sequence encoding a heterologous protein.

30. The method of claim 29 wherein the heterologous protein is an immunogenic compound or an antigen of a pathogen.

31. A vaccine for protecting a mammalian host against infection comprising the recombinant adenovirus vector of claim 13 and a pharmaceutically acceptable excipient.

32. The recombinant adenovirus vector of claim 6 wherein said adenovirus vector further comprises human adenoviral sequences.

33. The recombinant adenovirus vector according to claim 3 wherein said adenovirus vector comprises a bovine adenovirus sequence(s) essential for encapsidation, wherein said sequence consists of the sequence between nt 224 and nt 541 of the sequence as shown in SEQ ID NO: 1, or a portion of said sequence, wherein said sequence, or portion thereof, is capable of encapsidating an adenovirus genome, and a nucleic acid sequence encoding a heterologous protein, wherein said adenovirus vector is deleted in part or all of one or more nucleic acid sequences encoding non-essential adenovirus proteins.

34. The recombinant adenovirus vector according to claim 33, wherein said adenovirus vector further comprises human adenovirus sequences, bovine adenovirus sequences, porcine adenovirus sequences, and/or canine adenovirus sequences.

35. The recombinant adenovirus vector according to claim 33, wherein said adenovirus vector further comprises human adenovirus sequences.

36. The recombinant adenovirus vector according to claim 33 wherein said heterologous protein encodes an immunogenic polypeptide.

37. The recombinant adenovirus vector according to claim 33 wherein said heterologous protein encodes an antigen of a pathogen.

38. The recombinant adenovirus vector according to claim 37 wherein said pathogen is selected from the group consisting of a human pathogen, a bovine pathogen, a porcine pathogen, and a canine pathogen.

39. The bovine adenovirus sequence of claim 1 wherein said sequence, or portion thereof, is between nt 224 and nt 540 of the sequence as shown in SEQ ID NO:1.

40. The bovine adenovirus sequence of claim 1 wherein said sequence, or portion thereof, is selected from the group consisting of a sequence between nt 224 to nt 382; a sequence between nt 224 to nt 311; a sequence between nt 311 to nt 382; a sequence between nt 383 to nt 468; a sequence between nt 467 to nt 541; a sequence between nt 311 to nt 383; a sequence between nt 382 to nt 467; and a sequence between nt 384 to nt 541 of the sequence as shown in SEQ ID NO:1.

41. The bovine adenovirus vector of claim 2 wherein said sequence, or portion thereof, is between nt 224 and nt 540 of the sequence as shown in SEQ ID NO:1.

42. The bovine adenovirus vector of claim 2 wherein said sequence, or portion thereof, is selected from the group consisting of a sequence between nt 224 to nt 382; a sequence between nt 224 to nt 311; a sequence between nt 311 to nt 382; a sequence between nt 383 to nt 468; a sequence between nt 467 to nt 541; a sequence between nt 311 to nt 383; a sequence between nt 382 to nt 467; and a sequence between nt 384 to nt 541 of the sequence as shown in SEQ ID NO: 1.

* * * * *

SEQUENCE LISTING

<160> NUMBER OF SEQ ID NOS: 19

<210> SEQ ID NO 1
<211> LENGTH: 660
<212> TYPE: DNA
<213> ORGANISM: Bovine adenovirus

<400> SEQUENCE: 1

| catcatcaat | aatctacagt | acactgatgg | cagcggtcca | actgccaatc | atttttgcca | 60 |
| cgtcatttat | gacgcaacga | cggcgagcgt | ggcgtgctga | cgtaactgtg | gggcggagcg | 120 |
| cgtcgcggag | gcggcggcgc | tgggcggggc | tgagggcggc | gggggcggcg | cgcggggcgg | 180 |
| cgcgcgggggc | ggggcgaggg | gcggagttcc | gcacccgcta | cgtcattttc | agacattttt | 240 |
| tagcaaattt | gcgccttttg | caagcatttt | tctcacattt | caggtattta | gagggcggat | 300 |
| ttttggtgtt | cgtacttccg | tgtcacatag | ttcactgtca | atcttcatta | cggcttagac | 360 |
| aaattttcgg | cgtcttttcc | gggtttatgt | ccccggtcac | ctttatgact | gtgtgaaaca | 420 |
| cacctgccca | ttgtttaccc | ttggtcagtt | ttttcgtctc | ctagggtggg | aacatcaaga | 480 |
| acaaatttgc | cgagtaattg | tgcacctttt | tccgcgttag | gactgcgttt | cacacgtaga | 540 |
| cagacttttt | ctcattttct | cacactccgt | cgtccgcttc | agagctctgc | gtcttcgctg | 600 |
| ccaccatgaa | gtacctggtc | ctcgttctca | acgacggcat | gagtcgaatt | gaaaaagctc | 660 |

<210> SEQ ID NO 2
<211> LENGTH: 14
<212> TYPE: DNA
<213> ORGANISM: Human adenovirus
<220> FEATURE:
<221> NAME/KEY: misc_feature
<222> LOCATION: 5, 6, 7, 8, 9, 10, 11, 12
<223> OTHER INFORMATION: n = A,T,C or G

<400> SEQUENCE: 2
tttgnnnnnn nncg        14

<210> SEQ ID NO 3
<211> LENGTH: 18
<212> TYPE: DNA
<213> ORGANISM: Artificial Sequence
<220> FEATURE:
<223> OTHER INFORMATION: Synthetic Construct

<400> SEQUENCE: 3
cgtcttcaag gatccgaa        18

<210> SEQ ID NO 4
<211> LENGTH: 18
<212> TYPE: DNA
<213> ORGANISM: Artificial Sequence
<220> FEATURE:
<223> OTHER INFORMATION: Synthetic Construct

<400> SEQUENCE: 4
atactgctgc agcagcga        18

<210> SEQ ID NO 5
<211> LENGTH: 27

-continued

```
<212> TYPE: DNA
<213> ORGANISM: Artificial Sequence
<220> FEATURE:
<223> OTHER INFORMATION: Synthetic Construct

<400> SEQUENCE: 5
ccgctcgagg acgtagcggg tgcggaa                                       27

<210> SEQ ID NO 6
<211> LENGTH: 27
<212> TYPE: DNA
<213> ORGANISM: Artificial Sequence
<220> FEATURE:
<223> OTHER INFORMATION: Synthetic Construct

<400> SEQUENCE: 6
ccgctcgagc gtacttccgt gtcacat                                       27

<210> SEQ ID NO 7
<211> LENGTH: 27
<212> TYPE: DNA
<213> ORGANISM: Artificial Sequence
<220> FEATURE:
<223> OTHER INFORMATION: Synthetic Construct

<400> SEQUENCE: 7
ccgctcgaga acaccaaaaa tccgccc                                       27

<210> SEQ ID NO 8
<211> LENGTH: 27
<212> TYPE: DNA
<213> ORGANISM: Artificial Sequence
<220> FEATURE:
<223> OTHER INFORMATION: Synthetic Construct

<400> SEQUENCE: 8
ccgctcgagg tttatgtccc cggtcac                                       27

<210> SEQ ID NO 9
<211> LENGTH: 27
<212> TYPE: DNA
<213> ORGANISM: Artificial Sequence
<220> FEATURE:
<223> OTHER INFORMATION: Synthetic Construct

<400> SEQUENCE: 9
ccgctcgagc ccggaaaaga cgccgaa                                       27

<210> SEQ ID NO 10
<211> LENGTH: 27
<212> TYPE: DNA
<213> ORGANISM: Artificial Sequence
<220> FEATURE:
<223> OTHER INFORMATION: Synthetic Construct

<400> SEQUENCE: 10
ccgctcgagg gaacatcaag aacaaat                                       27

<210> SEQ ID NO 11
<211> LENGTH: 27
<212> TYPE: DNA
<213> ORGANISM: Artificial Sequence
<220> FEATURE:
<223> OTHER INFORMATION: Synthetic Construct

<400> SEQUENCE: 11
```

-continued ccgctcgaga ccctaggaga cgaaaaa                                                  27

<210> SEQ ID NO 12
<211> LENGTH: 27
<212> TYPE: DNA
<213> ORGANISM: Artificial Sequence
<220> FEATURE:
<223> OTHER INFORMATION: Synthetic Construct

<400> SEQUENCE: 12
ccgctcgagc agactttttc tcatttt                                                  27

<210> SEQ ID NO 13
<211> LENGTH: 28
<212> TYPE: DNA
<213> ORGANISM: Artificial Sequence
<220> FEATURE:
<223> OTHER INFORMATION: Synthetic Construct

<400> SEQUENCE: 13
ccgctcgaga cgtgtgaaac gcagtcct                                                 28

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14
ccgctcgagt cattttctca cactccgt                                                 28

<210> SEQ ID NO 15
<211> LENGTH: 28
<212> TYPE: DNA
<213> ORGANISM: Artificial Sequence
<220> FEATURE:
<223> OTHER INFORMATION: Synthetic Construct

<400> SEQUENCE: 15
cggctcgaga aaagtctgt ctacgtgt                                                  28

<210> SEQ ID NO 16
<211> LENGTH: 28
<212> TYPE: DNA
<213> ORGANISM: Artificial Sequence
<220> FEATURE:
<223> OTHER INFORMATION: Synthetic Construct

<400> SEQUENCE: 16
ccgctcgagt cacactccgt cgtccgct                                                 28

<210> SEQ ID NO 17
<211> LENGTH: 27
<212> TYPE: DNA
<213> ORGANISM: Artificial Sequence
<220> FEATURE:
<223> OTHER INFORMATION: Synthetic Construct

<400> SEQUENCE: 17
ccgcaattga gttccgcacc cgctacg                                                  27

<210> SEQ ID NO 18
<211> LENGTH: 25
<212> TYPE: DNA
<213> ORGANISM: Artificial Sequence

```
-continued

<220> FEATURE:
<223> OTHER INFORMATION: Synthetic Construct

<400> SEQUENCE: 18
gcgtcgactt aaaacaaaga gtcat                                              25

<210> SEQ ID NO 19
<211> LENGTH: 24
<212> TYPE: DNA
<213> ORGANISM: Artificial Sequence
<220> FEATURE:
<223> OTHER INFORMATION: Synthetic Construct

<400> SEQUENCE: 19
cgggatccgc agcggtgact taac                                               24
```